US008758591B2

(12) United States Patent
Adeloju

(10) Patent No.: US 8,758,591 B2
(45) Date of Patent: Jun. 24, 2014

(54) ELECTROCHEMICAL NANOCOMPOSITE BIOSENSOR SYSTEM

(75) Inventor: Samuel Bodunrin Olufemi Adeloju, Beaconsfield (AU)

(73) Assignee: Sam Adeloju, Beaconsfield, Victoria (AU)

(*) Notice: Subject to any disclaimer, the term of this patent is extended or adjusted under 35 U.S.C. 154(b) by 761 days.

(21) Appl. No.: 12/747,706

(22) PCT Filed: Dec. 12, 2008

(86) PCT No.: PCT/AU2008/001830
§ 371 (c)(1),
(2), (4) Date: Sep. 22, 2010

(87) PCT Pub. No.: WO2009/073927
PCT Pub. Date: Jun. 18, 2009

(65) Prior Publication Data
US 2011/0042225 A1 Feb. 24, 2011

(30) Foreign Application Priority Data

Dec. 13, 2007 (AU) ................. 2007906759

(51) Int. Cl.
*G01N 27/327* (2006.01)
(52) U.S. Cl.
USPC ............. 205/777.5; 204/403.01; 204/403.14; 205/792
(58) Field of Classification Search
USPC ............. 204/403.01–403.15; 205/777.5, 792
See application file for complete search history.

(56) References Cited

U.S. PATENT DOCUMENTS

2004/0182719 A1 9/2004 Purvis et al.
2006/0289307 A1 12/2006 Yu et al.
2007/0029195 A1 2/2007 Li et al.

FOREIGN PATENT DOCUMENTS

JP     2007-127620     5/2007

OTHER PUBLICATIONS

Vidal et al. "In Situ Preparation of Overoxidized PPy/o-PPD Bilayer Biosensors for the Determination of Glucose and Cholesterol in Serum", Eurosensors XII, Proceedings of the 12th European Conference on Solid-State Transducers and the 9th UK Conference on Sensors and Their Applications, Southhampton, UK, Sep. 13-16, 1998 (1998), vol. 1, pp. 525-528.*
Adeloju et al. "Fabrication of ultra-thin polypyrrole-glucose oxidase film from supporting electrolyte-free monomer solution for potentiometric biosensing of glucose," Biosensors & Bioelectronics 16 (2001), pp. 133-139.*
Slide presentation by Samuel Adeloju presented at the International Congress of Nanotechnology in San Francisco on Nov. 2, 2005, 22 slides.*
Njagi et al. "Stable enzyme biosensors based on chemically synthesized Au-polypyrrole nanocomposites," Biosensors and Bioelectronics 23 (2997) 168-175.*

(Continued)

*Primary Examiner* — Alex Noguerola
(74) *Attorney, Agent, or Firm* — Nixon Peabody LLP; Jeffrey L. Costellia

(57) ABSTRACT

The present invention relates to an electrode useful in electrochemical nanobiosensors for determining the presence or concentration of analytes in aqueous samples. In particular, the electrode comprises a biocatalyst or other bioreceptor entrapped in a conducting polymeric film deposited on a conducting material and a non-conducting or conducting coating. In particular embodiments, the conducting polymeric layer also comprises metallic nanoparticles. Electrochemical nanobiosensors containing the electrode, methods of making the electrode or sensor and methods of detecting analytes are other aspects of the invention.

18 Claims, 41 Drawing Sheets

(56) References Cited

OTHER PUBLICATIONS

Habermüller et al. "An Oxygen-Insensitive Reagentless Glucose Biosensor Based on Osmium-Complex Modified Polypyrrole," Electroanalysis 2000, 12, No. 17 pp. 1383-1389.*

Vidal et al., "In situ preparation of overoxidized PPy / oPPD bilayer biosensors for the determination of glucose and cholesterol in serum", Sensors and Actuators, 1999, vol. 57, pp. 219-226.

Sharpe, "It's a Bug's Life: Biosensors for environmental Monitoring", Journal of Environmental Monitoring, 2003, vol. 5, pp. 109N-113N.

International Search Report for PCT/AU2008/001830 dated Feb. 23, 2009.

International Preliminary Report on Patentability for PCT/AU2008/001830 dated Jun. 15, 2010.

Besombes et al., "Improvement of poly(amphiphilic pyrrole) enzyme electrodes via the incorporation of synthetic laponite-clay-nanoparticles", Talanta, vol. 44, 1997, pp. 2209-2215.

Extended European Search Report, European Patent Office, European Patent Application No. 08858482.6, mailed Mar. 18, 2014.

* cited by examiner a)

b)

Combined probe

Pin connector

ELECTROCHEMICAL NANOCOMPOSITE BIOSENSOR SYSTEM

The present invention relates to an electrode useful in electrochemical nanobiosensors for determining the presence or concentration of analytes in aqueous samples. In particular, the electrode comprises a biocatalyst or other bioreceptor entrapped in a conducting polymeric film deposited on a conducting material and a non-conducting or conducting coating. In particular embodiments, the conducting polymeric layer also comprises metallic nanoparticles. Electrochemical nanobiosensors containing the electrode, methods of making the electrode or sensor and methods of detecting analytes are other aspects of the invention.

Electrochemical nanobiosensors that include biocatalysts such as enzymes have been developed for the detection of analytes in biological, environmental and industrial samples. These electrochemical sensors rely on the immobilisation of an enzyme or other bioreceptor layer on an electrode surface, and monitor changes occurring at the electrode that result from the biocatalytic or bioreceptor reaction. An example of such an electrochemical biosensor is a glucose electrochemical sensor used to detect the amount of glucose in biological samples such as blood.

Some biocatalyst containing electrochemical sensors have also been developed to monitor environmental toxins such as phenolic compounds. However, the proper functioning of these enzyme electrodes is highly dependent on the means of immobilising the enzyme and the amount of enzyme immobilised. Enzyme containing electrodes also encounter difficulties with the long term stability, particularly the stability of the biocatalyst or the biocatalytic layer, the presence of multiple electroactive species in complex biological, environmental or food samples and the fouling or degradation of the electrode during use.

The present invention is based on the discovery that ultrathin (nanometer thick) polymeric films entrapping at least one biocatalyst or other bioreceptor can be used in electrodes to provide particularly sensitive detection of organic molecules or inorganic ions, that incorporation of metallic nanoparticles in at least some instances improves sensitivity and that a protective porous thin coating may improve long term stability, suppress or eliminate interference from other electroactive species and/or reduce fouling or degradation of the electrode.

In one aspect of the present invention, there is provided an electrode for use in an electrochemical sensor, comprising
 i) a conducting substrate;
 ii) a conducting polymeric film disposed on the conducting substrate, and in which at least one biocatalyst or other bioreceptor has been immobilised, the thickness of the polymeric film being in the range of 20 nm to 170 nm; and
 iii) a porous coating disposed on at least a portion of the polymeric film.

This electrode is useful as a working electrode in an electrochemical sensor and may be used together with a reference electrode to provide potentiometric detection of an analyte or may be used together with a reference electrode and an auxiliary or counter electrode to provide amperometric detection of an analyte.

The conducting substrate can be any conducting or semiconducting substance in any form. Examples of suitable forms include wires, rods, discs, foils, wafers or chips, or may be a coating deposited on a non-conducting substrate by any known deposition process. Suitable conducting substances include platinum, gold, silver, copper, aluminium, iridium, palladium, rhodium, silicon, zinc, iron, steel, brass, carbon and the like. In preferred embodiments, the conducting substrate is platinum, gold, glassy carbon or copper.

The conducting polymeric film may be any polymeric film capable of conducting electrons and entrapping a biocatalyst or other bioreceptor. The polymeric film may be prepared from water soluble or non-water soluble monomers. In preferred embodiments the polymeric film is formed from water soluble monomers. Preferred conducting polymeric films include polypyrrole (PPy), polyaniline and polythiophene.

The biocatalyst or other bioreceptor may be any biocatalyst or other bioreceptor or combination of biocatalysts or other bioreceptors suitable for detecting a desired analyte.

Since the biocatalyst or other bioreceptor is selective for a particular analyte, it is selected on the basis of the analyte to be detected. For example, if the analyte to be detected is glucose, the biocatalyst or other bioreceptor entrapped in the conducting polymeric film is glucose oxidase (GOx). An exemplary list of biocatalysts or other bioreceptors selective for particular analytes is given in Table 1.

TABLE 1

| Bioreceptor | Analyte |
|---|---|
| Acetylcholine esterase and choline oxidase | organophosphate insecticides |
| alcohol dehydrogenase | alcohol |
| ascorbic acid oxidase | ascorbic acid |
| asparagus peroxidase | fluoride |
| cholesterol oxidase | cholesterol |
| cholesterol dehydrogenase | cholesterol |
| cholesterol esterase | cholesterol ester |
| choline oxidase | choline |
| DNA | hybridization, organic and inorganic toxins |
| formaldehyde dehydrogenase | formaldehyde |
| formate dehydrogenase | formate |
| fructose dehydrogenase | fructose |
| glucose oxidase (GOx) | glucose |
| glutamate dehydrogenase or decarboxylase | glutamate |
| horseradish peroxidase | hydrogen peroxide |
| lactate dehydrogenase or oxidase | lactate |
| lactose dehydrogenase | lactose |
| lipase | fats |
| NADH dehydrogenase | NADH |
| nitrate reductase (NaR) | nitrate ions |
| nitrite reductase | nitrite ions |
| oxalate oxidase | oxalate |
| pectin esterase | pectin |
| penicillinase | penicillin |
| polyphenol oxidase | dopamine |
| purine nucleoside phosphorylase (PNP) and xanthine oxidase (XOD) | Phosphate ions |
| pyruvate decarboxylase | pyruvate |
| rhodanase and sulfite oxidase | cyanide |
| sucrose dehydrogenase | sucrose |
| sulfite oxidase (SOx) | sulfite ions |
| tyrosinase | phenols, catechol |
| urease | urea |
| xanthine oxidase | hypoxanthine |

In some cases the sensitivity of the electrode can be improved by the use of more than one biocatalyst or other bioreceptor. The use of a two biocatalyst or bioreceptor system in which the biocatalysts or bioreceptors work in tandem may provide a greater number of electroactive species that can be detected at the electrode for each molecule of analyte. This may lower the detection limit of the electrode. An example of a two biocatalyst or bioreceptor system is provided by the use of PNP and XOD in the detection of phosphate. The use of these two biocatalysts produces three electroactive molecules, two molecules of $H_2O_2$ and one molecule of uric acid per molecule of phosphate detected.

The biocatalyst or other bioreceptor may be immobilised in the polymeric film by being covalently, ionically or coordinatively bound to the polymeric film and/or may be entrapped in the polymeric film. In preferred embodiments, the biocatalyst or other bioreceptor is entrapped in the polymeric film.

Immobilisation of the biocatalyst or other bioreceptor in the polymeric film prevents or reduces the biocatalyst or other bioreceptor diffusing away from the electrode surface for a given period of time in which the electrode is in use. The term "non-leachable biocatalyst or bioreceptor" refers to a biocatalyst or other bioreceptor that does not substantially diffuse away from the electrode surface. Immobilisation may make the biocatalyst or other bioreceptor temporarily non-leachable or permanently non-leachable. In some cases the biocatalyst or other bioreceptor slowly leaches from the electrode over time or after a given period, the non-leachable biocatalyst or other bioreceptor becomes leachable. The leaching of biocatalyst or other bioreceptor from the polymeric film reduces the sensitivity of the electrode.

The thickness of the conducting polymeric film is in the range of about 20 nm to about 170 nm, preferably in the range of 30 nm to 170 nm, 30 nm to 160 nm, 30 nm to 150 nm, 30 nm to 140 nm, 30 nm to 130 nm, 30 nm to 120 nm, 30 nm to 110 nm, 30 nm to 100 nm, 30 nm to 90 nm or 30 nm to 80 nm. The optimal thickness of the polymeric film may depend on the conditions of application such as types and concentrations of biocatalyst or other bioreceptor, monomers, electrolytes, metallic nanoparticles, the applied current density during the electropolymerisation deposition and the duration of the electropolymerisation deposition. The thickness of the conducting polymeric film and its mode of application may influence the sensitivity of the electrode. For example, optimal sensitivity of a phosphate electrode may be obtained for a 135 nm PPy-PNP—XOD polymeric film formed at an applied current density of 0.5 $mA/cm^2$ for a polymerisation period of 120 seconds.

Optionally the polymeric film may comprise other components such as a co-factor, redox mediator and/or metallic nanoparticles.

A co-factor may be required for biocatalyst or other bioreceptor activity and may also be included in the polymeric film together with the biocatalyst or other bioreceptor. A co-factor is an organic or inorganic atom or molecule that is required by a biocatalyst or other bioreceptor to achieve full activity. Co-factors include, but are not limited to, metal ions such as zinc, cobalt, iron and magnesium, metal clusters such as iron-sulfur clusters and organic compounds such as NAD/NADH, flavin, thiamine and heme. Whether a co-factor is required and the type of co-factor required will depend on the nature of the biocatalyst or other bioreceptor immobilised in the polymeric film. A person skilled in the art would be able to determine whether a co-factor is required and the type of co-factor required for a given biocatalyst or other bioreceptor.

A redox mediator is a compound that carries electrons between the analyte and the working electrode, either directly or indirectly in cooperation with other agents. A suitable redox mediator used in conjunction with oxidoreductase enzymes is potassium ferricyanide ($K_4Fe(CN)_6$). Other redox mediators are known to those skilled in the art and include, but are not limited to, azure A, bromophenol blue, bromophenol red, ferrocene, methylviolgen, Prussian blue, safranine O and thionin acetate. In some cases, where a co-factor such as NADH is required, this can be replaced by using a redox mediator to achieve a more sensitive and cheaper alternative. For example, the need for NADH for the biosensing of nitrate with nitrate reductase can be replaced with the use of a mediator such as azure A, bromophenol blue, bromophenol red, methylviolgen, safranine O and thionin acetate.

Metallic nanoparticles are also an optional component of the conducting polymeric film. The presence of nanoparticles increases the surface area of the polymeric film and thereby increases sensitivity and robustness of the electrode. The metallic nanoparticles are normally incorporated in the polymeric film from 0.00025% to 1%. especially 0.0005% to 1%, or from 0.00025% to 0.5%. Suitable metallic nanoparticles include those made of gold (Au), silver (Ag), platinum (Pt), alumina ($Al_2O_3$), zinc oxide (ZnO) and silica ($SiO_2$). The nanoparticles have dimensions generally in the range of 1 to 20 nm, especially 5 nm to 20 nm. The presence of metallic nanoparticles in the conducting polymeric film or on the biosensor, can be confirmed by scanning electron microscopy (SEM) and transmission electron microscopy (TEM).

While in some embodiments the nanoparticles and/or redox mediator and optionally a co-factor are incorporated into the conducting polymeric film, in other embodiments it may be advantageous to incorporate the redox mediator and/or metallic nanoparticles and optionally a co-factor in a further conducting nanolayer between the conducting substrate and the conducting polymeric film. The conducting nanolayer may be another conducting polymeric layer that is prepared by electropolymerisation of a monomer solution containing the redox mediator and/or the metallic nanoparticles. Such a nanolayer may have a thickness in the order of 20 nm to 100 nm, especially 25 to 90 nm, 30 to 80 nm. 35 to 70 nm. 40 to 60 nm, more especially about 50 nm.

It may be advantageous to incorporate the metallic nanoparticles alone or together with a redox mediator and optionally a co-factor in a nanolayer between the conducting substrate and the conducting polymeric film to achieve satisfactory coverage, especially full coverage (100%), of the conducting substrate with the conducting polymeric film containing the biocatalyst or other bioreceptor. Satisfactory coverage of the conducting substrate is at least 30% coverage, especially 50% coverage, more especially at least 70% coverage. In particular embodiments, the coverage is at least 90% of the conducting substrate, especially full coverage 100%.

The conducting polymeric film containing the biocatalyst or other bioreceptor and other optional components such as redox mediators and/or co-factors, may be deposited on the nanolayer coated conducting substrate by electrochemical polymerisation as described herein.

In some embodiments, a co-factor, if required by the biocatalyst or other bioreceptor, may be incorporated in the nanolayer, in the conducting polymeric film with the biocatalyst or other bioreceptor, or in both the nanolayer and the conducting polymeric film. In particular embodiments, the co-factor is incorporated at least in the layer containing the biocatalyst or other bioreceptor.

The coating can be any porous conducting, non-conducting material or substantially non-conducting material that does not prevent the analyte being able to come into contact with the biocatalyst or other bioreceptor immobilised in the conducting polymeric film. In particular embodiments, the porous coating is non-conducting. Suitable non-conducting materials have no or poor conductivity, such as a conductivity of less than $10^{-8}$ S/cm, and result in the formation of an insulating or gel-type layer of about 5 to 50 nm in thickness. In particular embodiments, the non-conducting porous coating is poly-ortho-phenylenediamine (P-oPDA) or is formed from a mixture of bovine serum albumin and glutaraldehyde (BSA-GLA). In other embodiments, metallic nanoparticles may be incorporated into the porous coating and thereby make the coating conducting.

The porous coating is generally more than 5 nm thick. The thickness will depend on the means of depositing the coating. In some embodiments, such as those in which the coating is electrochemically deposited, the coating is in the range of about 5 nm to about 50 nm thick, especially 5 nm to 40 nm, 5 nm to 30 nm, 5 nm to 20 nm, especially about 10 nm.

The thickness of the porous coating may be variable. For example, a BSA-GLA coating may be applied by spreading a solution on the conducting polymeric film or by dipping the electrode in a solution of BSA-GLA. These methods provide a less consistent coverage and thickness of the coating compared to electrochemical deposition.

The porous coating is disposed on at least a portion of the conducting polymeric film. In some embodiments, the porous coating is disposed on all of the conducting polymeric film.

The porous coating prevents or reduces the leaching of the biocatalyst or other bioreceptor from the conducting polymeric film. This may extend the functional life of the electrode and allow consistent calibration for a longer period of time. The porous coating may also assist in reducing or preventing interference from electroactive species other than the analyte that may be present in a test sample allowing more accurate measurement of analyte. The porous coating may also assist in reducing or preventing fouling of the electrode. The term "fouling of the electrode" refers to blockage of the electrode surface by sample components that may affect the performance of the biosensor due to inaccessibility of the analyte to the biocatalyst or other bioreceptor and/or prevention of the diffusion of the biocatalytic product towards or away from the electrode.

In another aspect of the present invention, there is provided a method of making an electrode comprising:
  i) a conducting substrate;
  ii) a conducting polymeric film disposed on the conducting substrate, and in which at least one biocatalyst or other bioreceptor has been immobilised, the thickness of the polymeric film being in the range of 20 nm to 170 nm; and
  iii) a porous coating disposed on at least a portion of the polymeric film;
the method comprising:
  a) depositing a conducting polymeric film in which at least one biocatalyst or other bioreceptor is immobilised on a conducting substrate by electrochemical polymerisation of a composition comprising at least one monomer capable of forming the conducting polymeric film and the at least one biocatalyst; and
  b) depositing a porous coating on at least a portion of the conducting polymeric film.

In some embodiments, metallic nanoparticles are included in the composition and are thereby incorporated into the polymeric film.

Electrochemical polymerisation is a process in which a solution of monomer is oxidised or reduced to an activated form that polymerises to form a polymeric film directly on the electrode surface. In this process, the biocatalyst or other bioreceptor is entrapped in the polymeric film during polymerisation or the biocatalyst or other bioreceptor is chemically linked to at least some of the monomers in the composition. In some embodiments, the biocatalyst or other bioreceptor is entrapped in the polymeric film.

Electrochemical polymerisation may occur by galvanostatic (constant current), potentiostatic (constant potential) or potentiodynamic (varied potential) means. In particular embodiments, the electrochemical polymerisation occurs galvanostatically.

The amount of biocatalyst or other bioreceptor incorporated in the conducting polymeric film increases with film thickness. However, the sensitivity of the electrode to the analyte depends not only on film thickness but also on the conditions used during electropolymerisation, such as the duration of polymerisation, the applied current density, biocatalyst or other bioreceptor and monomer concentrations used during galvanostatic polymerisation. The composition may be stirred or may be left unstirred during polymerisation. Often the composition is not stirred. Optimisation of the conditions allows optimum sensitivity with a film thicknesses in the range of 20 to 170 nm.

In some embodiments, the composition of monomer and biocatalyst or other bioreceptor is an aqueous composition. The composition components, for example, monomer and biocatalyst or other bioreceptor concentration, solvent, pH or buffer concentration, salt concentration, co-factor concentration are preferably optimised to reduce or prevent denaturation of the biocatalyst or other bioreceptor before, during and after polymerisation and immobilisation.

The composition comprising the monomer and biocatalyst(s) or other bioreceptor(s) may optionally comprise other components such as redox mediators, metallic nanoparticles, biocatalyst substrates or co-factors and buffers. In some embodiments, the aqueous solution does not contain buffers other than those associated with the biocatalyst or other bioreceptors. Additional buffers need not be added. In some embodiments, a redox mediator such as potassium ferricyanide ($K_4Fe(CN)_6$) is included in the aqueous solution and incorporated into the polymeric film.

Metallic nanoparticles, such as gold, silver, platinum, zinc oxide, silica or alumina nanoparticles, may be suspended in the composition comprising the monomer and biocatalyst(s) or other bioreceptor(s) and are entrapped in the polymeric film during electrochemical polymerisation. In some embodiments the metallic nanoparticles are homogeneously suspended in the composition by stirring or using a dispersing agent. Suitable dispersing agents include, but are not limited to, alkanethiols, dodecanethiol, dodecylthioether, 11-mercapto-1-undecanol, poly(methacrylic acid), poly(N-isoproplyacrylamide), polyvinyl alcohol, polyvinyl pyrrolidine K-90, sodium citrate, sodium diphenylamine sulfonate, stearylamine and tannic acid.

In other embodiments, optional components may be incorporated after electrochemical polymerisation and preferably before coating the conducting polymeric film with the porous coating. Optional components may be incorporated into the polymeric film by diffusion, adsorption or by chemical interactions such as covalent bonding, crosslinking, ionic bonding or by coordination with metal ions in the polymeric film.

Alternatively, optional components such as metallic nanoparticles and/or redox mediators may be incorporated in a further conducting nanolayer between the conducting substrate and the polymeric conducting film. These optional components may be included in a conducting nanolayer by any suitable means including electrochemical polymerisation, physical or chemical adsorption or electroplatinisation. The conducting polymeric film is then deposited on the conducting nanolayer.

The optimisation of components in the composition and conditions used in preparing the electrode may be achieved by varying concentrations of monomer, biocatalyst or other bioreceptor, optional redox mediator, optional co-factor, optional metallic nanoparticles and non-conducting monomer, preparing electrodes and assessing biosensor response and sensitivity by potentiometric or amperometric detection as demonstrated in the Examples.

In some embodiments the concentration of components included 0.1-0.5M monomer such as pyrrole, 0.1-50 mM redox mediator such as ferricyanide and 0.00025 to 0.5% metallic nanoparticles. This composition is suitable for use with biocatalysts such as

| | |
|---|---|
| XOD | 6-12 U/mL and PNP 48-96 U/mL, |
| SOx | 2-12 U/mL, |
| nitrate reductase | 0.5-5 U/mL and 0.02-1 mM NADH. |

In some embodiments, the concentration of monomer such as oPDA for preparing a porous non-conducting coating, e.g. P-oPDA, is 20-50 mM.

The porous coating may be deposited by any suitable means, for example, by dip-coating, spin coating, electrochemical deposition and electrochemical polymerisation. The means of depositing the porous coating will depend on the nature of the coating. For example, a protein coating, such as bovine serum albumin polymerised with glutaraldehyde (BSA-GLA) may be most conveniently deposited by dip-coating, spin coating or surface deposition and drying. In another example, a solution of a suitable monomer that is able to be oxidised or reduced may be coated on the conducting polymeric film by electrochemical polymerisation. In the case where a non-conducting porous coating is required, the monomer and polymerisation conditions would be selected so that the resulting polymeric coating was non-conducting.

In some embodiments, porous coating is formed by electrochemical polymerisation of a composition of ortho-phenylenediamine (oPDA). The electrochemical polymerisation occurs directly onto the conducting polymeric film and its deposition may be assisted by the conductivity of the conducting polymeric film. The electrochemical polymerisation used is preferably potentiodynamic polymerisation based on cyclic voltammetry. The thickness and porosity of the coating may be controlled by the range of potential cycled, the number of cycles and the cycle rate. The thickness of the coating may be self limiting and the polymerisation reaction may stop when the monomer solution is sufficiently insulated from the conducting polymeric film by the formed coating. However, the number of cycles used affects the nature of the coating. Less than 4 scans (or cycles) reduce sensitivity of the electrode presumably by increasing the barrier between the analyte and the biocatalyst. However, with 4 scans (or cycles) or greater than 4 scans (or cycles), the sensitivity increased. Without wishing to be bound by theory, the improvement in sensitivity may be due to
  a) the containment and retention of biocatalyst in the conducting polymeric film by the poly-orthophenylenediamine (P-oPDA) coating enabling more catalytic products to reach the conducting substrate; and/or
  b) a change in the nature of the P-oPDA coating, such as a change in porosity, allowing more analyte to reach the biocatalyst in the conducting polymeric film.

The porous coating is deposited from a solution in which the coating components are soluble. For example, the coating components BSA-GLA may be deposited by dipping in an aqueous solution of BSA-GLA. In another embodiment, a monomer, such as oPDA, may be polymerised from an aqueous solution or an aqueous buffered solution. Suitable buffers include barbitone, phosphate ammonium chloride, EDTA, citrate and Tris buffers. Care must be taken to ensure that a buffer does not contain the analyte that is to be detected. For example, a phosphate buffer would generally be unsuitable for use in the preparation of a nanobiosensor to be used for detecting phosphate ions, without copious washing and testing of the biosensor against blank solutions.

Salts such as sodium and/or potassium chloride may also be present in the solution from which the porous coating is deposited.

It is also possible to include biocatalysts or other bioreceptors, co-factors, metallic nanoparticles and/or redox mediators in the porous coating. If metallic nanoparticles are incorporated into the porous coating, the porous coating will be a conducting porous coating.

Optionally, when the porous coating is BSA-GLA, biocatalysts or other bioreceptors, redox mediators, metallic nanoparticles and/or co-factors incorporated in the conducting polymeric film may also be included in the porous coating.

In another aspect of the present invention, there is provided an electrochemical sensor comprising
  a) a working electrode comprising
    i) a conducting substrate;
    ii) a conducting polymeric film disposed on the conducting substrate, and in which at least one biocatalyst or other bioreceptor has been immobilised, the thickness of the polymeric film being in the range of 20 nm to 170 nm; and
    iii) a porous coating disposed on at least a portion of the polymeric film.
  b) an auxiliary electrode and/or reference electrode; and
  c) a measurement device.

The electrochemical sensor may be used for potentiometric monitoring or if an auxiliary or counter electrode is included to form a three electrode sensor, amperometric monitoring may be used.

The reference electrode allows accurate measurement of potential at the working electrode to be made with respect to a fixed reference point. Any suitable reference electrode or pseudo-reference electrode may be used. Examples of suitable reference electrodes include silver/silver chloride, mercury/mercury chloride, calomel and platinum/hydrogen reference electrodes. Suitable pseudo-reference electrodes include platinum wire, carbon-fibre, glassy carbon or gold electrodes. In some embodiments, the reference electrode is a silver/silver chloride reference electrode.

The working electrode provides either a measurement of potential with respect to the reference electrode or a current measurement and therefore a measurement of the presence of or concentration of analyte in the test sample.

In the potentiometric mode, the working electrode and reference electrode are connected to an electronic measuring device that measures the difference in potential between the reference electrode and the working electrode, for example, a potentiostat or galvanostat or digital voltmeter, where a range of between −1 V and +1 V may be measured.

In the amperometric mode, the working, reference and auxiliary electrodes are connected to a potentiostat/galvanostat which applies the required potential while concurrently measuring the resulting current. The resulting current may vary from −100 µA to +100 µA. In some embodiments, a much lower current may be generated and this may be as low as −100 nA to +100 nA.

In some embodiments, the electronic measuring device may be connected to a computer or may include a computational device and software that converts the measurement from the measurement device into a signal that can be digitally displayed as a concentration of analyte in the test sample. A schematic diagram of an electrochemical sensor containing a working electrode and a reference electrode is shown in FIG. 1.

In some embodiments the electrochemical sensor further comprises an auxiliary or counter electrode to allow amperometric detection. In the three electrode sensor, the potential of the working electrode is fixed relative to the reference electrode as a function of time. The applied potential serves as a driving force for the electron transfer reaction of the electroactive species. The resulting current is a measure of the rate of the electron transfer reaction and is proportional to the concentration of analyte.

The auxiliary or counter electrode, if present, is also connected to the measurement device.

While it is possible that each electrode in the sensor may be configured separately as single electrodes that must be contacted with a test sample simultaneously but separately, it is preferred that each electrode is incorporated into a single combined electrode system (FIG. 2A). Specific examples of a combined electrode system are provided in FIGS. 2B and 2C. In a single combined electrode system, the working electrode and the reference electrode, and optionally the auxiliary or counter electrode are housed in a single unit.

The electrodes in the single combined electrode system may be configured in any suitable conformation, such as those shown in FIGS. 3A and 3B. In some embodiments, the single combined electrode system is configured so that the working electrode is extended in length in comparison to the reference electrode and optionally the auxiliary or counter electrode. This allows the working electrode to be prepared, for example, by the application of the conducting polymeric film and the porous coating, after assembly of the combined electrode. This configuration ensures that the reference and/or the auxiliary electrode is not fouled during preparation (or replacement) of the working electrode. In some embodiments of the single combined electrode system, the working electrode may be able to be separated from the reference electrode and optionally from the auxiliary or working electrode.

The housing of the combined single electrode may be made from any suitable material especially a non-reactive material. Examples of suitable housing materials are chlorotrifluoroethylene plastic, polyetheretherketon plastic, Teflon and glass.

The combined electrodes also include an electrolyte, such as potassium chloride. The electrolyte may be present in solution or gel form. For example, if solution free conditions are required, a KCl saturated gel may be used.

The electrochemical sensor is useful for the selective detection of analytes in biological, environmental, food and beverage samples, as well as in industrial samples.

In another aspect of the invention, there is provided a method for detecting an analyte in a sample comprising exposing the sample to an electrochemical sensor, the electrochemical sensor comprising an electrode comprising:
i) a conducting substrate;
ii) a conducting polymeric film disposed on the conducting substrate, and in which at least one biocatalyst or other bioreceptor has been immobilised, the thickness of the polymeric film being in the range of 20 nm to 170 nm; and
iii) a porous coating disposed on at least a portion of the polymeric film;
and observing the presence or absence of the analyte in the sample.

At least one biocatalyst is selective for the analyte to be detected, for example, as set out in Table 1 above. Furthermore, the electrode may be prepared as previously described and may include further components and nanolayers as previously described.

Suitable biological samples include blood, serum, urine, milk and other biological fluids. Suitable environmental samples include samples taken from water sources such as lakes, rivers, wells, sewers, storm water drains, sewage treatment plants, effluent outflow, water storage facilities, dams, swimming pools and salt water sources such as the sea. Suitable food or beverage samples include juices, drinking water, wine, beer and liquid or liquefied and solubilised food samples. Other samples that may be tested for an analyte include soil and sediments such as sediments found in lakes, rivers, stagnant water, sewage treatment plants, sewers and around effluent outflow. Soil and sediment samples may require treatment before analysis can be performed. For example, soil and sediment samples may need solubilisation or extraction and may require filtration.

In some embodiments of the method, the test samples are discrete samples obtained from different sites, patients, foods or drinks. For example, a water sample may be taken from a water source such as a river periodically, for example, once a week or once a month, and analysed immediately or stored for later analysis.

The electrochemical sensor is used to detect the presence or absence of an analyte. In preferred embodiments, when the presence of an analyte is detected, the concentration of the analyte is determined.

The detection limit for the analyte depends on the nature of the analyte and the biocatalyst(s) or other bioreceptor(s) used. If the analyte is present at a concentration below the detection limit, a combination of biocatalysts or other bioreceptors that work in tandem may be considered or a sample could be concentrated by taking a measured volume of sample and evaporating a portion of the liquid to provide a second measured volume, testing the evaporated sample to determine the concentration of analyte and calculating the concentration in the original volume. Similarly, if the concentration of the analyte is too high, a given volume of sample could be diluted to a second measured volume, after testing the sample, the concentration of analyte in the original sample volume may be calculated.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Monomer solution/condition: 0.1 M Py. 0.0005% AuNPs, 6 U/mL XOD, 48 U/mL XOD, 0.1 mM $K_4Fe(CN)_6$ and 0.6 mA/cm$^2$ current density while various polymerisation periods were used for polymerisation of the PPy-XOD-PNP—Fe$(CN)_6^{4-}$—AuNPs films.

Figure 30:
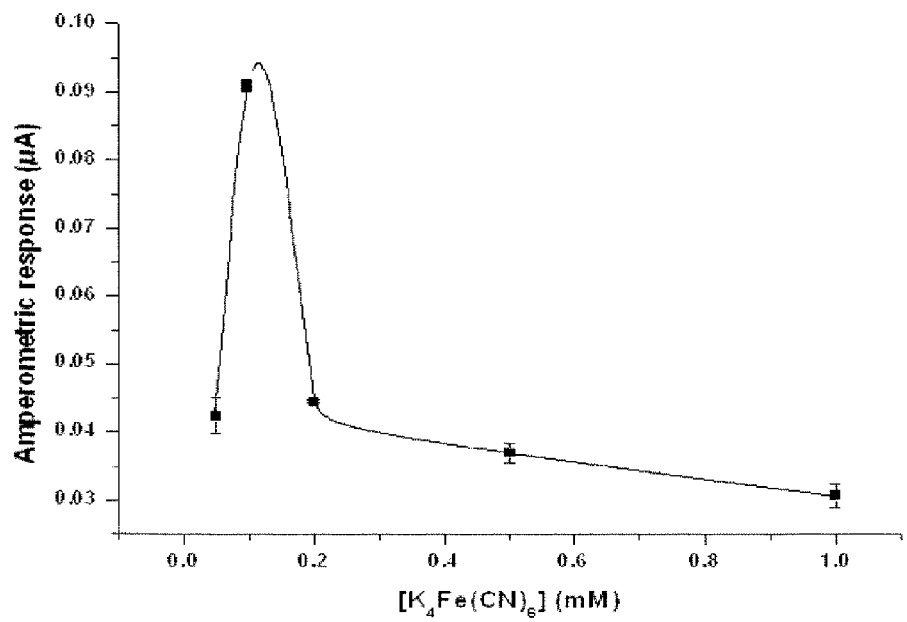

FIG. 30 is a graphical representation showing the effect of $K_4Fe(CN)_6$ concentration on the PPy-XOD-PNP—Fe$(CN)_6^{4-}$—AuNPs biosensor response on modified combined electrode-4. Monomer solution/condition: 0.5 M pyrrole, 48 U/mL PNP, 6 U/mL XOD, 0.0005% AuNPs, 0.6 mA/cm$^2$ current density and polymerisation period of 120 seconds while various concentrations of $K_4Fe(CN)_6$ were used.

Figure 31:
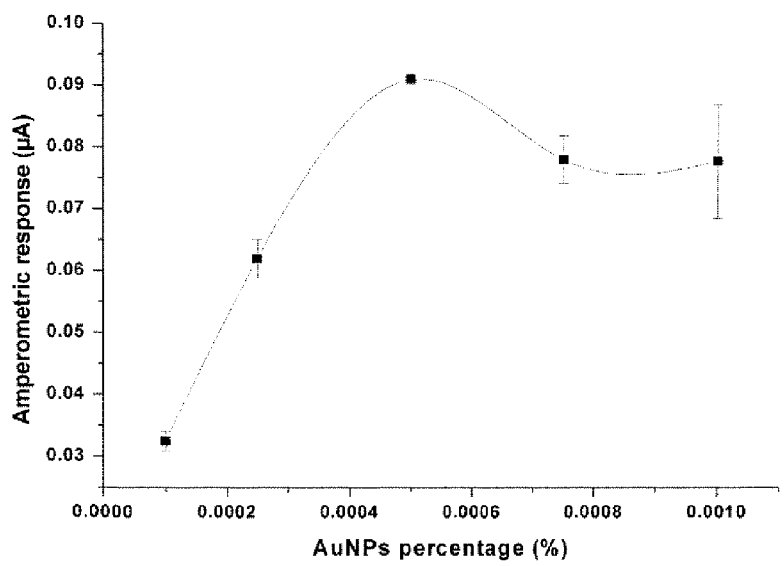

FIG. 31 is a graphical representation showing the effect of AuNPs concentration on the PPy-XOD-PNP—Fe$(CN)_6^{4-}$—AuNPs single layer biosensor response taken with combined electrode-4. Monomer solution/condition: 0.5 M pyrrole, 48 U/mL PNP, 6 U/mL XOD, 0.1 mM $K_4Fe(CN)_6$, 0.6 mA/cm$^2$ current density and polymerisation period of 120 seconds while various concentrations of AuNPs were used for optimisation studies.

Figure 32A:
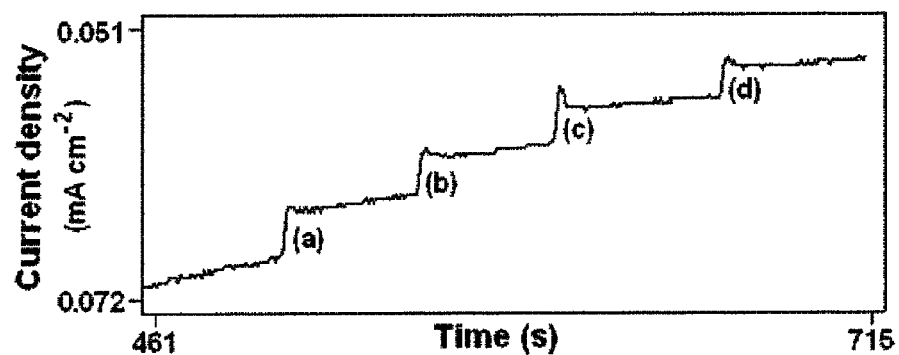

FIG. 32A shows the amperometric response obtained with PPy-XOD-PNP—Fe$(CN)_6^{4-}$—AuNPs biosensor on combined electrode-4 for (a) 454.5 µM, (b) 871.2 µM, (c) 1255.8 µM, (d) 1613 µM and (e) 1946.4 µM phosphate concentrations at −200 mV in a measurement solution containing 0.05 M each of NaCl and barbitone buffer and 10 mM of inosine solutions. Monomer solution/conditions for the growth of PPy-XOD-PNP—Fe$(CN)_6^{4-}$—AuNPs are as described for FIG. 29.

Figure 32B:
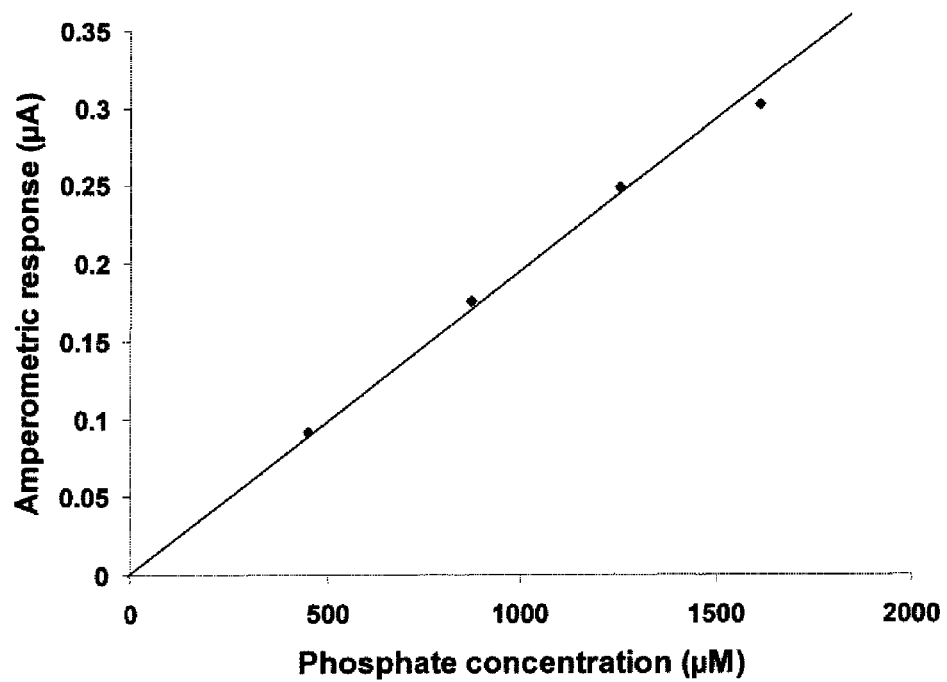

FIG. 32B is a graphical representation of a typical calibration curve obtained with PPy-XOD-PNP—Fe$(CN)_6^{4-}$—AuNPs biosensor on combined electrode-4. Phosphate measurements were taken at −200 mV in a measurement solution containing 0.05 M each of NaCl and barbitone buffer and 10 mM of inosine solutions. Monomer solution/conditions for the growth of PPy-XOD-PNP—Fe$(CN)_6^{4-}$—AuNPs are as described for FIG. 29.

Figure 33:
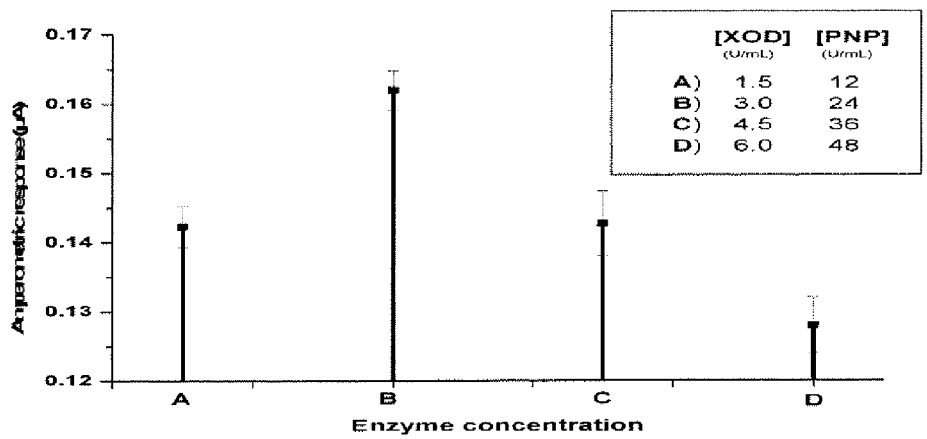

FIG. 33 is a graphical representation of the effect of enzyme concentration on the PPy-XOD-PNP—Fe$(CN)_6^{4-}$—AuNPs biosensor response using combined electrode-6. (A) 1.5 and 12, (B) 3.0 and 24, (C) 4.5 and 36, and (D) 6.0 and 48 U/mL of XOD and XOD. Monomer solution/condition: 0.1 M Py, 0.0005% AuNPs, 0.1 mM $K_4Fe(CN)_6$, a current density of 0.6 mA cm$^{-2}$ and a polymerisation period of 120 seconds.

Figure 34:
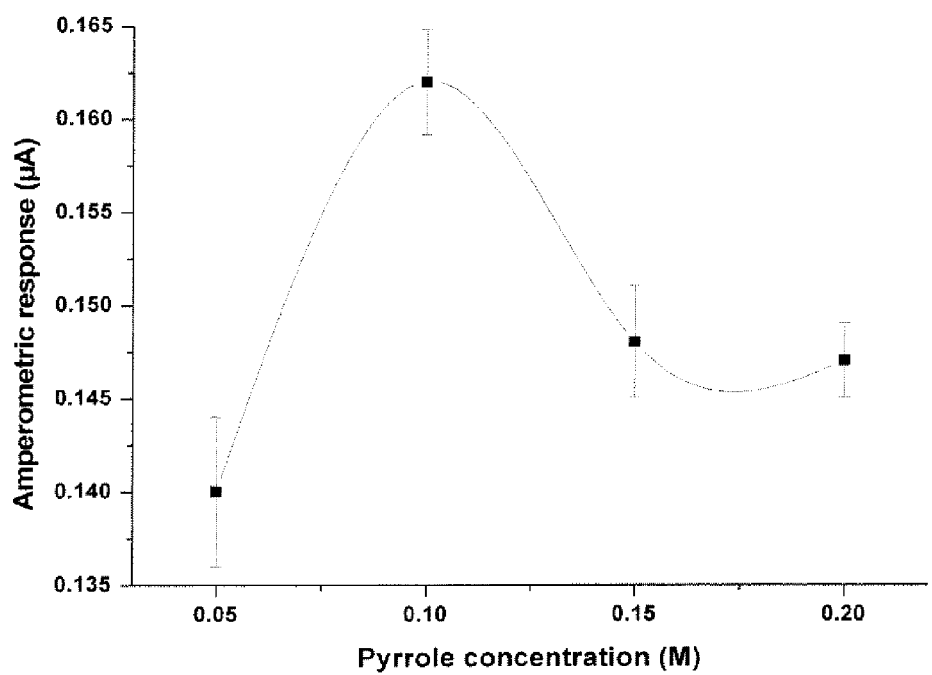

FIG. 34 is a graphical representation showing the effect of pyrrole concentration on the PPy-XOD-PNP—Fe$(CN)_6^{4-}$—AuNPs biosensor response using combined electrode-6. Monomer solution/condition: 3.0 U/mL XOD, 48 U/mL PNP. 0.0005% AuNPs, 0.1 mM $K_4Fe(CN)_6$, a current density of 0.6 mA cm$^{-2}$ and a polymerisation period of 120 seconds while various concentrations of pyrrole were used for polymerisation of the PPy-XOD-PNP—Fe$(CN)_6^{4-}$—AuNPs films.

Figure 35:
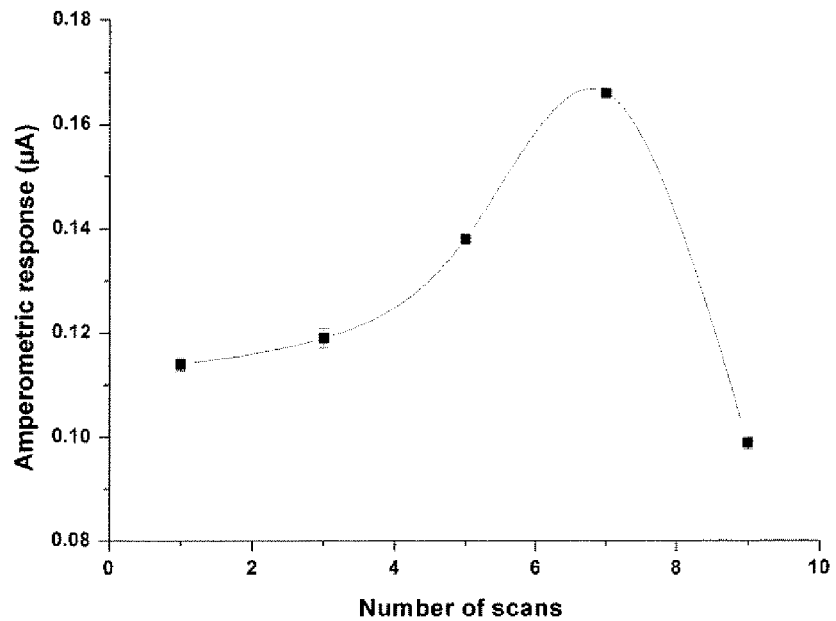

FIG. 35 is a graphical representation showing the effect of the number of scans for growth of P-oPDA on the PPy-XOD-PNP—Fe$(CN)_6^{4-}$—AuNPs/P-oPDA biosensor response using combined electrode-6 for 0.45 mM phosphate concentration in a measurement solution comprising 0.05 M each of NaCl and barbitone buffer and 10 mM of inosine solutions. Monomer solution/condition: 0.1 M Pyrrole, 3.0 U/mL XOD, 48 U/mL PNP, 0.0005% AuNPs, 0.1 mM $K_4Fe(CN)_6$, a current density of 0.6 mA cm$^{-2}$ and a polymerisation period of 120 seconds for polymerisation of the PPy-XOD-PNP—Fe$(CN)_6^{4-}$—AuNPs films. A 50 mM solution of oPDA containing 75 mM Barbitone buffer and 0.5 M KCl was cycled between 0-800 mV for electrochemical polymerisation of P-oPDA over PPy-XOD-PNP—Fe$(CN)_6^{4-}$—AuNPs layer at 100 mV/s for varying number of scans.

Figure 36:
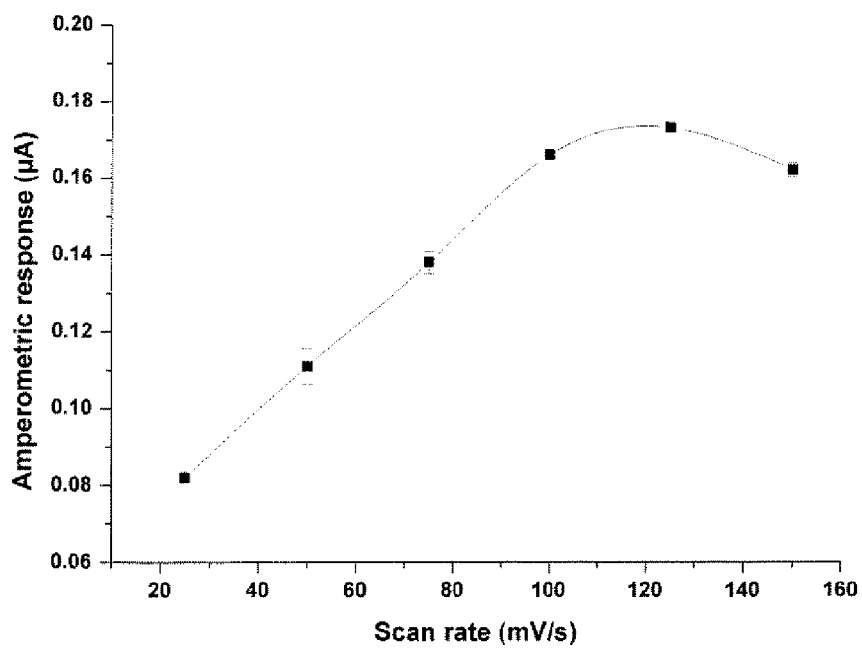

FIG. 36 is a graphical representation showing the effect of scan rate for growth of P-oPDA on the PPy-XOD-PNP—Fe$(CN)_6^{4-}$—AuNPs/P-oPDA biosensor response using combined electrode probe-6 for 0.45 mM phosphate concentration in a measurement solution comprising 0.05 M each of NaCl and barbitone buffer and 10 mM of inosine solutions. Monomer solution/condition: 0.1 M Pyrrole, 3.0 U/mL XOD, 48 U/mL PNP, 0.0005% AuNPs, 0.1 mM $K_4Fe(CN)_6$, a current density of 0.6 mA cm$^{-2}$ and a polymerisation period of 120 seconds for polymerisation of the PPy-XOD-PNP—Fe$(CN)_6^{4-}$—AuNPs films. A 50 mM solution of oPDA containing 75 mM Barbitone buffer and 0.5 M KCl was cycled between 0-800 mV for electrochemical polymerisation of P-oPDA over PPy-XOD-PNP—Fe$(CN)_6^{4-}$—AuNPs layer at various scan rates for 7 scans.

Figure 37:
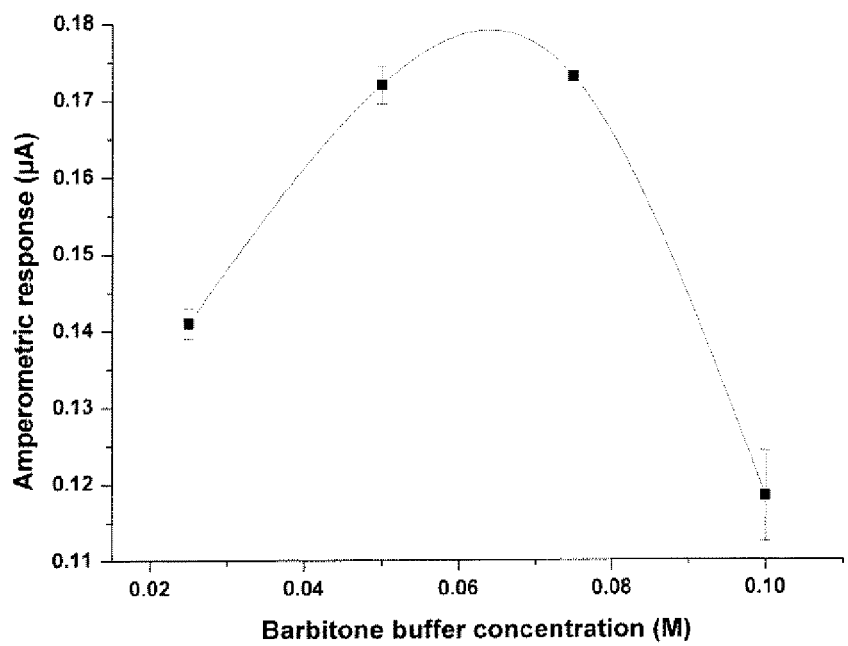

FIG. 37 is a graphical representation showing the effect of barbitone buffer concentration for growth of P-oPDA on the PPy-XOD-PNP—Fe$(CN)_6^{4-}$—AuNPs/P-oPDA biosensor response using combined electrode-6 for 0.45 mM phosphate concentration in a measurement solution comprising 0.05 M each of NaCl and barbitone buffer and 10 mM of inosine solutions. Monomer solution/condition: 0.1 M Pyrrole. 3.0 U/mL XOD, 48 U/mL PNP, 0.0005% AuNPs, 0.1 mM $K_4Fe(CN)_6$, a current density of 0.6 mA cm$^{-2}$ and a polymerisation period of 120 seconds for polymerisation of the PPy-XOD-PNP—Fe$(CN)_6^{4-}$—AuNPs films. A 50 mM solution of oPDA containing varying concentration of barbitone buffer and 0.5 M KCl was cycled between 0-800 mV for electrochemical polymerisation of P-o-PDA over PPy-XOD-PNP—Fe$(CN)_6^{4-}$—AuNPs layer at 125 mV/s for 7 scans.

Figure 38:
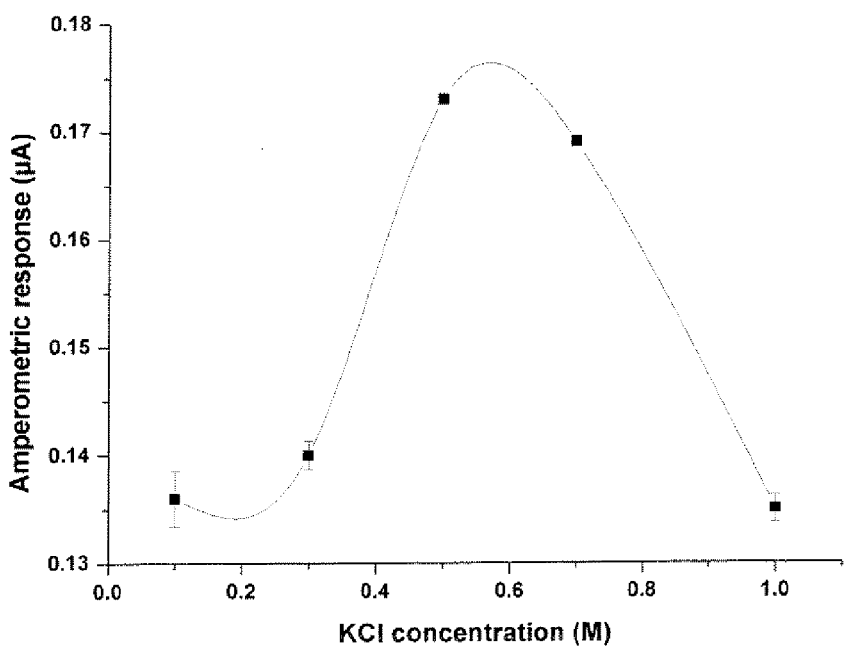

FIG. 38 is a graphical representation showing the effect of KCl concentration for growth of P-oPDA on the PPy-XOD-PNP—Fe$(CN)_6^{4-}$—AuNPs/P-oPDA biosensor response using combined electrode-6 for 0.45 mM phosphate concentration in a measurement solution comprising 0.05 M each of NaCl and barbitone buffer and 10 mM of inosine solutions. Monomer solution/condition: 0.1 M Pyrrole, 3.0 U/mL XOD, 48 U/mL PNP, 0.0005% AuNPs, 0.1 mM $K_4Fe(CN)_6$, a current density of 0.6 mA cm$^{-2}$ and a polymerisation period of 120 seconds for polymerisation of the PPy-XOD-PNP—Fe$(CN)_6^{4-}$—AuNPs films. A 50 mM solution of oPDA containing 0.075 M of barbitone buffer and varying concentrations of KCl were cycled between 0-800 mV for electrochemical polymerisation of P-oPDA over PPy-XOD-PNP—Fe$(CN)_6^{4-}$—AuNPs layer at 125 mV/s for 7 scans.

Figure 39:
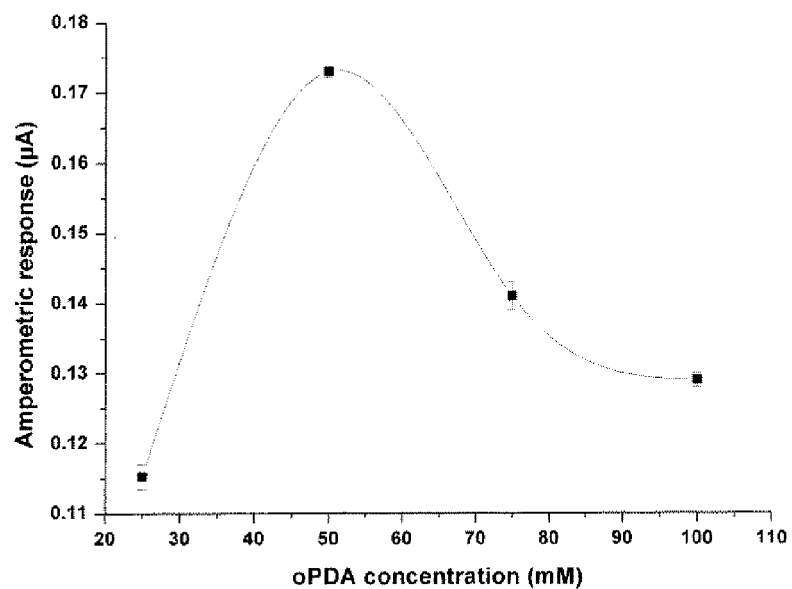

FIG. 39 is a graphical representation showing the effect of oPDA concentration for growth of P-oPDA layer on the PPy-XOD-PNP—Fe$(CN)_6^{4-}$—AuNPs/P-oPDA biosensor response using combined electrode-6 for 0.45 mM phosphate concentration in a measurement solution comprising 0.05 M each of NaCl and barbitone buffer and 10 mM of inosine solutions. Monomer solution/condition: 0.1 M Pyrrole, 3.0 U/mL XOD, 24 U/mL PNP, 0.0005% AuNPs, 0.1 mM $K_4Fe(CN)_6$, a current density of 0.6 mA cm$^{-2}$ and a polymerisation period of 120 seconds for polymerisation of the PPy-XOD-PNP—Fe$(CN)_6^{4-}$—AuNPs films. Various concentrations of oPDA were used in a polymerisation solution containing 0.075 M of barbitone buffer and 0.5 M of KCl and the potential was cycled between 0-800 mV for electrochemical polymerisation of P-oPDA over PPy-XOD-PNP-Fe$(CN)_6^{4-}$—AuNPs layer at 125 mV/s for 7 scans.

Figure 40:
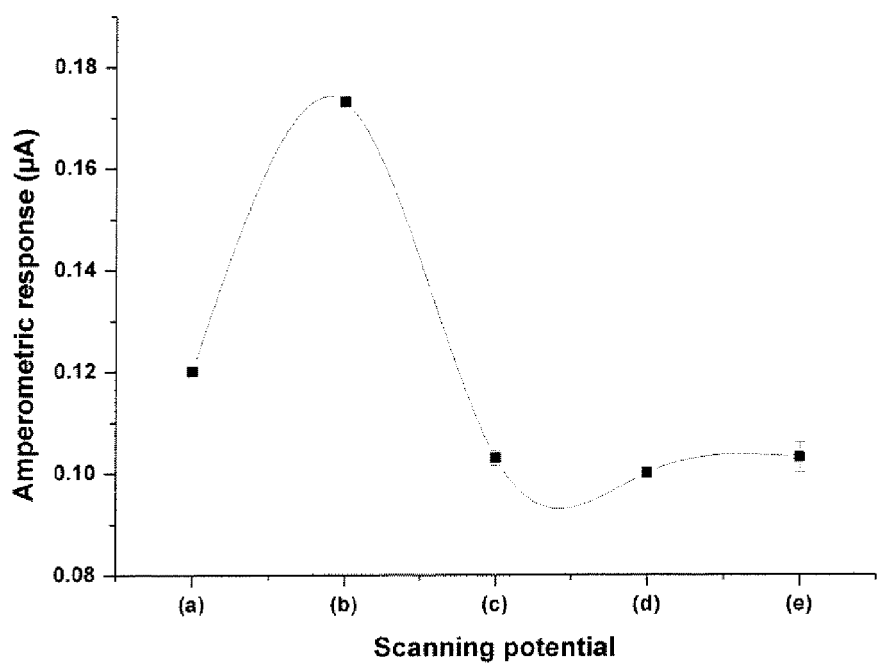

FIG. 40 is a graphical representation showing the effect of scanning potential for growth of P-oPDA layer on the PPy-XOD-PNP—Fe$(CN)_6^{4-}$—AuNPs/P-oPDA biosensor response using combined electrode probe-6 for 0.45 mM phosphate concentration in a measurement solution comprising 0.05 M each of NaCl and barbitone buffer and 10 mM of inosine solutions. A 50 mM solution of o-PDA containing 0.075 M of barbitone buffer and varying concentrations of KCl was cycled between (a) 0-1000, (b) 0-800, (c) 0-600, (d) 0-400 and (e) 0-200 mV for electrochemical polymerisation of P-oPDA over PPy-XOD-PNP—Fe(CN)$_6^{4-}$—AuNPs layer at 125 mV/s for 7 scans. Monomer solution/condition for 1$^{st}$ layer: 0.1 M Pyrrole, 3.0 U/mL XOD, 24 U/mL PNP. 0.0005% AuNPs, 0.1 mM K$_4$Fe(CN)$_6$, a current density of 0.6 mA cm$^{-2}$ and a polymerization period of 120 seconds for polymerisation of the PPy-XOD-PNP—Fe(CN)$_6^{4-}$—AuNPs films.

Figure 41A:
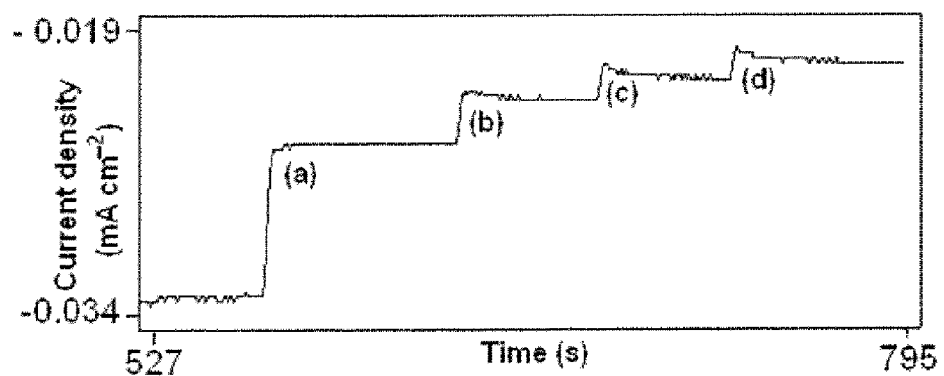

FIG. 41A shows the amperometric response obtained with PPy-XOD-PNP—Fe(CN)$_6^{4-}$—AuNPs/PoPDA biosensor on combined electrode probe-6 for (a) 454.5 µM, (b) 871.2 µM, (e) 1255.8 µM and (d) 1613 µM phosphate concentrations at −200 mV in a measurement solution containing 0.05 M each of NaCl and barbitone buffer and 10 mM of inosine solutions. Monomer solution/condition: 0.1 M Pyrrole, 3.0 U/mL XOD, 24 U/mL PNP, 0.0005% AuNPs, 0.1 mM K$_4$Fe(CN)$_6$, a current density of 0.6 mA cm$^{-2}$ and a polymerisation period of 120 seconds for polymerisation of the PPy-XOD-PNP—Fe(CN)$_6^{4-}$—AuNPs films. A 50 mM solution of oPDA containing 0.075 M of barbitone buffer and 0.5 M of KCl was cycled between 0-800 mV for electrochemical polymerisation of P-oPDA over PPy-XOD-PNP—Fe(CN)$_6^{4-}$—AuNPs layer at 125 mV/s for 7 scans.

Figure 41B:
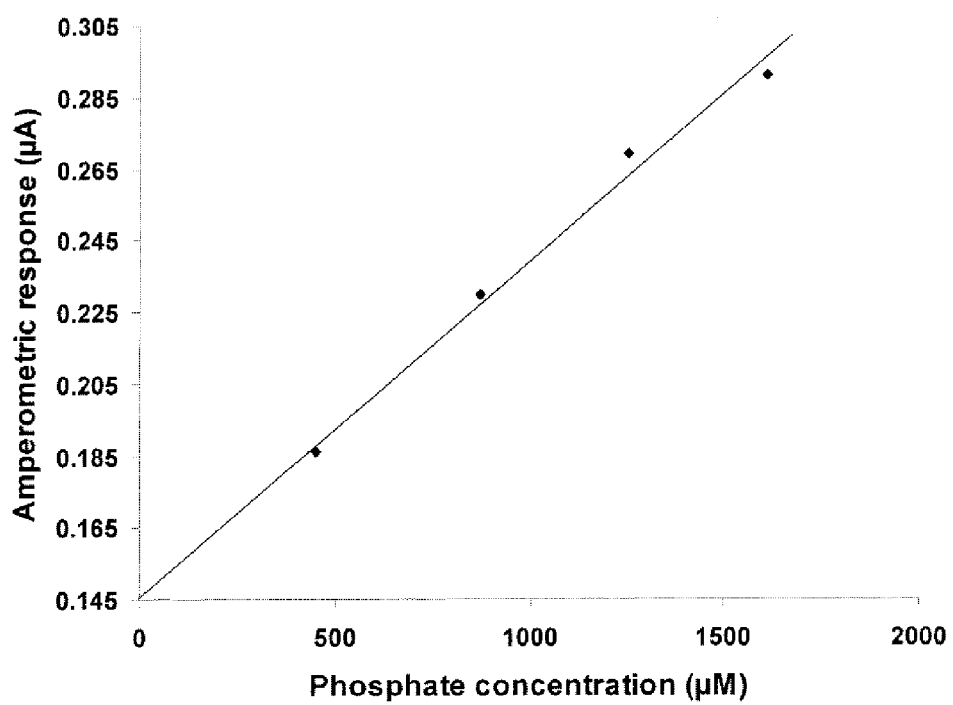

FIG. 41B is a graphical representation of a typical calibration curve obtained with with PPy-XOD-PNP—Fe(CN)$_6^{4-}$—AuNPs/P-oPDA biosensor on combined electrode probe-6 for increasing phosphate concentrations at −200 mV in a measurement solution containing 0.05 M each of NaCl and barbitone buffer and 10 mM of inosine solutions. Monomer solution/conditions for the growth of PPy-XOD-PNP—Fe(CN)$_6^{4-}$—AuNPs/P-oPDA are described in FIG. 41A.

Figure 42A:
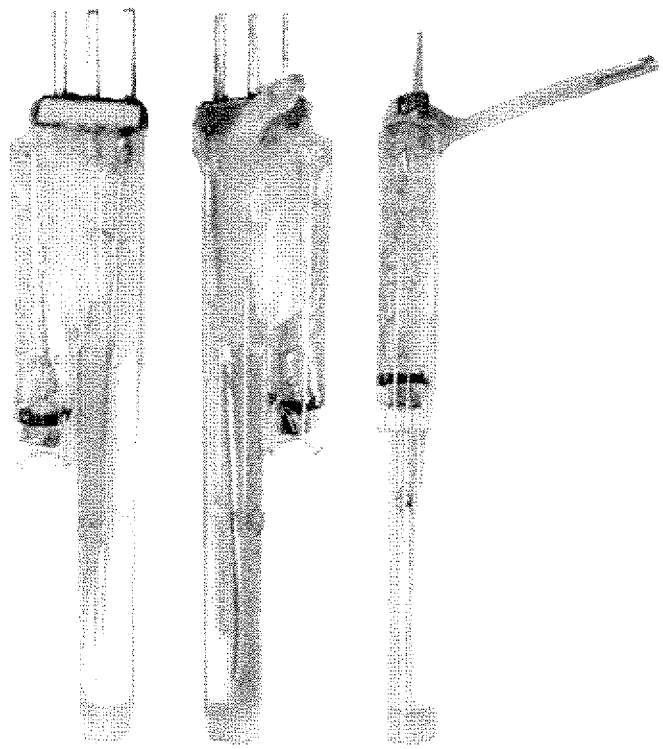
Figure 42B:
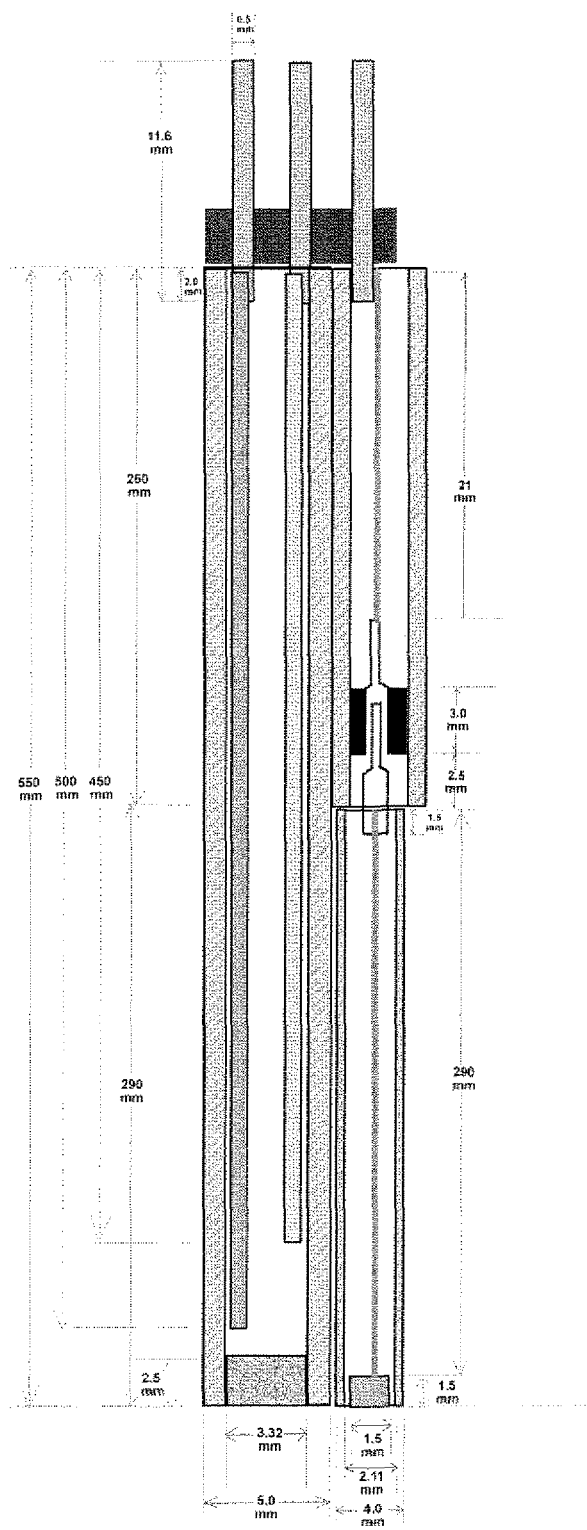
Figure 42C:
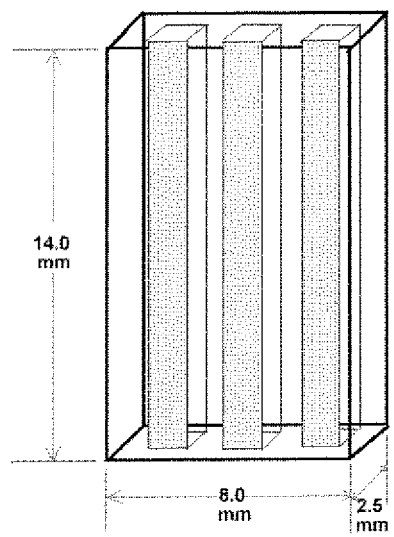
Figure 42D:
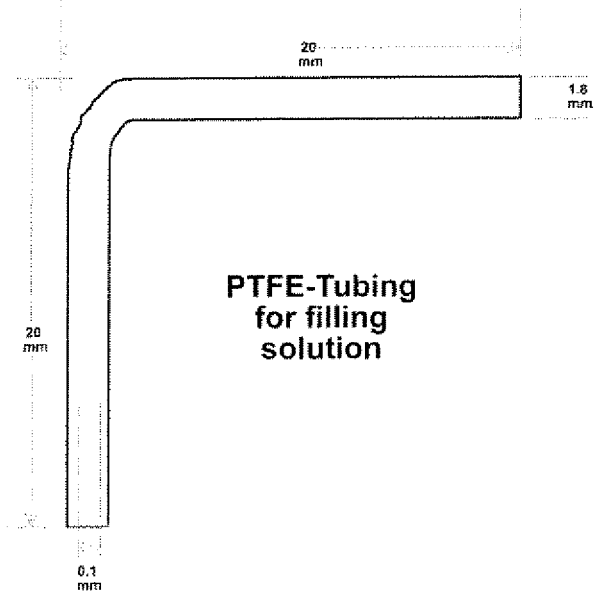

FIG. 42A is a photographic representation of different views of combined electrode-6. FIG. 42B is a schematic diagram of combined electrode-6. FIG. 42C is a schematic diagram of the pin connector and FIG. 42D is a schematic diagram of the PTFE tubing.

Figure 43:
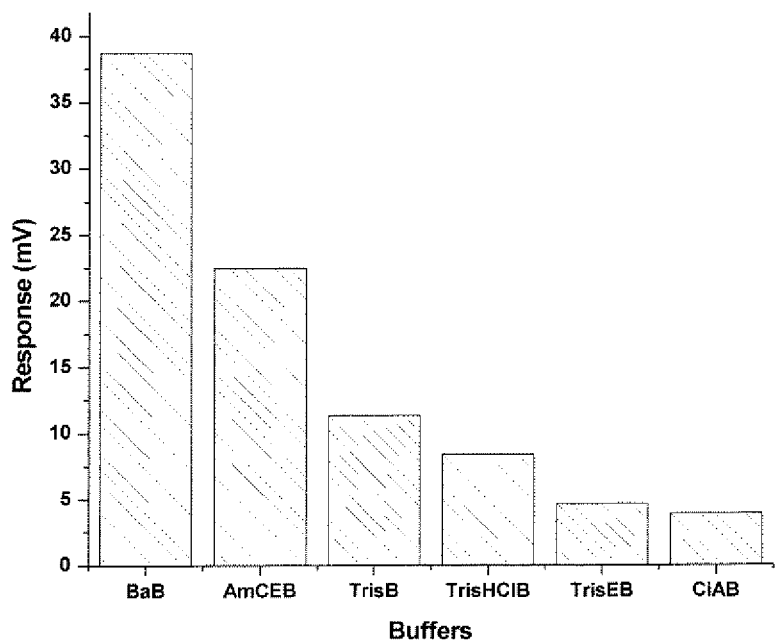

FIG. 43 is a graphical representation showing the effect of different buffers on potentiometric response obtained with PPy-XOD-PNP—Fe(CN)$_6^{4-}$—AuNPs/P-oPDA biosensor on combined electrode-6 for 0.45 mM phosphate concentration. BaB: Barbitone buffer; AmCEB: Ammonim chloride-EDTA buffer; TrisB: Tris buffer; TrisHClB: Tris-HCl buffer; TrisEB: Tris-EDTA buffer; CiAB: Citrate buffer; buffer concentrations: 0.05 M. Monomer solution/conditions 1$^{st}$ layer: 0.5 M Pyrrole, 2 U/mL XOD, 16 U/mL PNP, 0.00025% AuNPs, 0.2 mM K$_4$Fe(CN)$_6$, a current density of 0.8 mA cm$^{-2}$ and a polymerization period of 120 seconds. Monomer solution/conditions 2$^{nd}$ layer: 10 mM of oPDA were used in a polymerisation solution containing 0.05 M of each of above buffer and 0.5 M KCl and the potential was cycled between 0-800 mV for electrochemical polymerisation of P-oPDA over PPy-XOD-PNP—Fe(CN)$_6^{4-}$—AuNPs layer at 100 mV/s for 6 scans. Measurement conditions: 0.05 M each of NaCl and respective buffer and 10 mM of inosine with no current applied to the measurement solution at pH 7.0.

Figure 44:
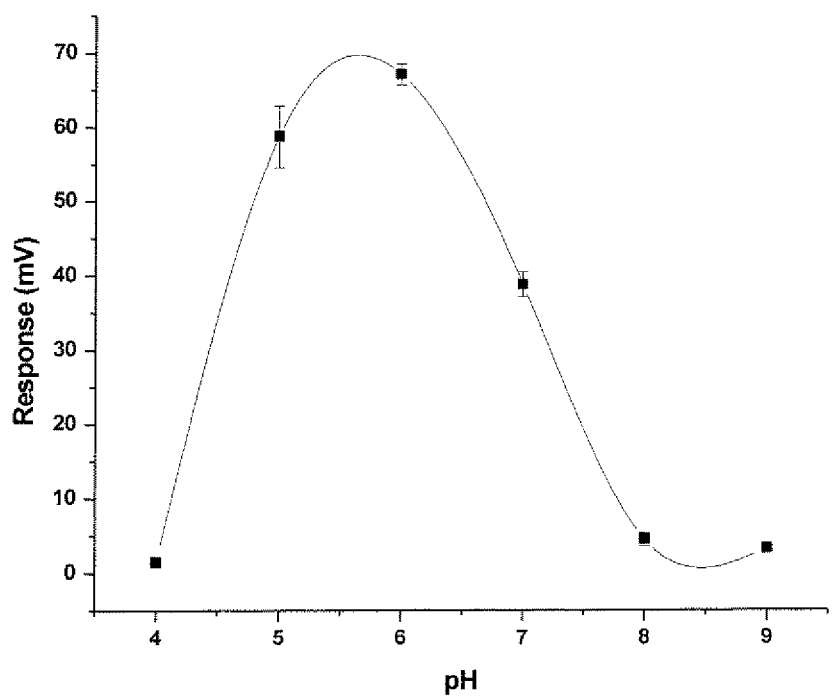

FIG. 44 is a graphical representation showing the effect of pH on potentiometric response obtained with PPy-XOD-PNP—Fe(CN)$_6^{4-}$—AuNPs/P-oPDA biosensor on combined electrode probe-6 for 0.45 mM phosphate concentration. Monomer solution/conditions 1$^{st}$ layer: 0.5 M Pyrrole, 2 U/mL XOD, 16 U mL PNP, 0.00025% AuNPs. 0.2 mM K$_4$Fe(CN)$_6$, a current density of 0.8 mA cm$^{-2}$ and a polymerisation period of 120 seconds. Monomer solution/conditions 2$^{nd}$ layer: 10 mM of oPDA were used in a polymerisation solution containing 0.05 M of barbitone buffer and 0.5 M KCl and the potential was cycled between 0-800 mV for electrochemical polymerisation of P-oPDA over PPy-XOD-PNP—Fe(CN)$_6^{4-}$—AuNPs layer at 100 mV/s for 6 scans. Measurement conditions: 0.05 M each of NaCl and barbitone buffer and 10 mM of inosine with no current applied to the measurement solution at different pH.

Figure 45A:
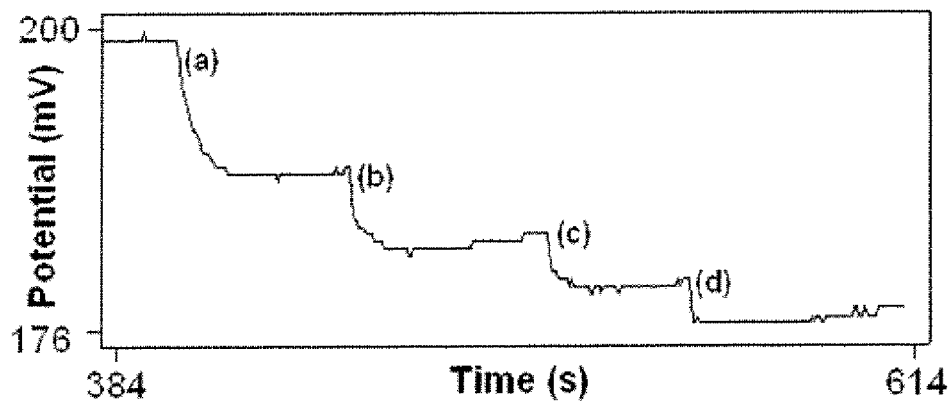

FIG. 45A shows the potentiometric response obtained with PPy-XOD-PNP—Fe(CN)$_6^{4-}$—AuNPs/P-oPDA biosensor on combined electrode probe-6 for (a) 45.4, (b) 87.2, (c) 125.7 and (d) 161.4 µM phosphate concentrations. Monomer solution/conditions 1$^{st}$ layer: 0.5 M Pyrrole, 2 U/mL XOD, 16 U/mL PNP, 0.00025% AuNPs. 0.2 mM K$_4$Fe(CN)$_6$, a current density of 0.8 mA cm$^{-2}$ and a polymerisation period of 120 seconds. Monomer solution/conditions 2$^{nd}$ layer: 10 mM of oPDA were used in a polymerisation solution containing 0.05 M of barbitone buffer and 0.5 M KCl and the potential was cycled between 0-800 mV for electrochemical polymerisation of P-oPDA over PPy-XOD-PNP—Fe(CN)$_6^{4-}$—AuNPs layer at 100 mV/s for 6 scans. Measurement conditions: 0.05 M each of NaCl and barbitone buffer and 10 mM of inosine with no current applied to the measurement solution at pH 6.0.

Figure 45B:
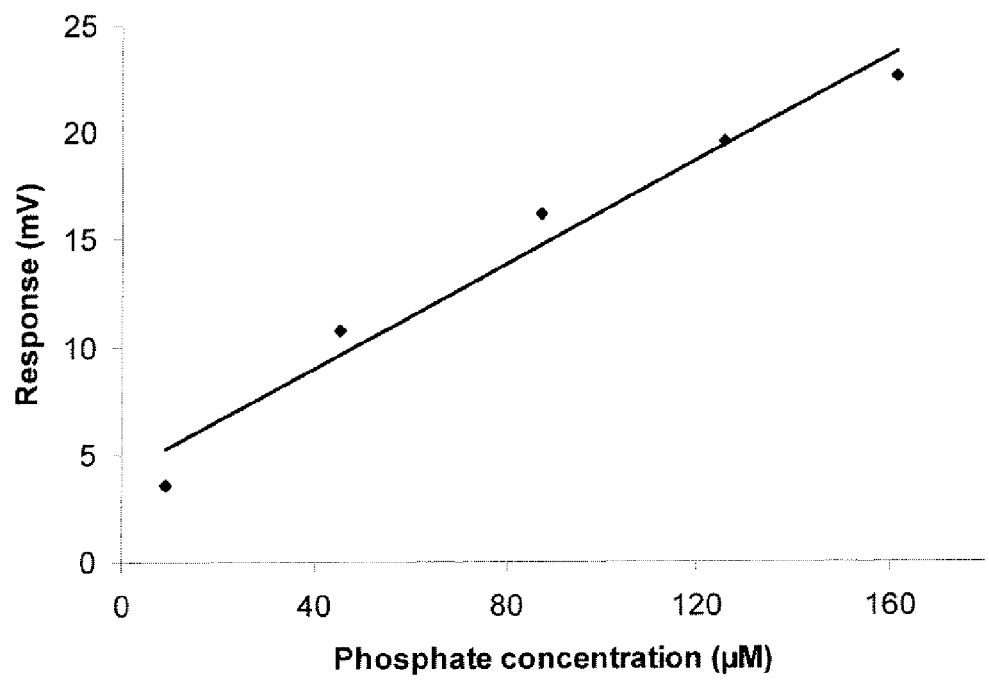

FIG. 45B is a graphical representation of a typical potentiometric calibration curve obtained with with PPy-XOD-PNP—Fe(CN)$_6^{4-}$—AuNPs/P-oPDA biosensor on combined electrode-6 for increasing phosphate concentrations. Monomer solution/conditions and measurement conditions are the same as mentioned for FIG. 45A.

Figure 45C:
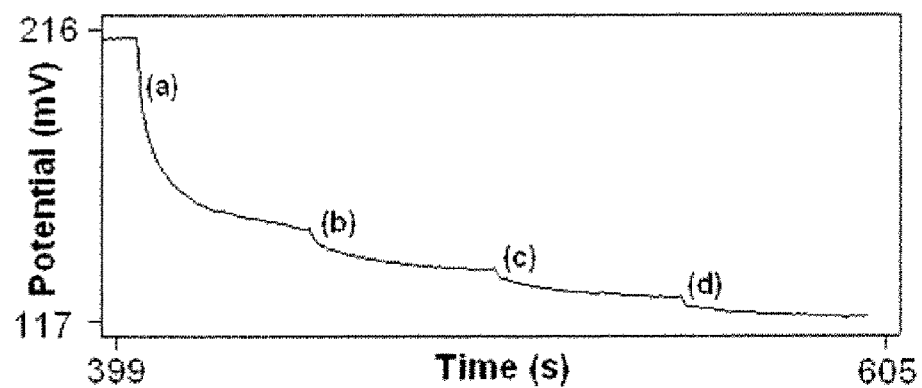

FIG. 45C shows the potentiometric response obtained with PPy-XOD-PNP—Fe(CN)$_6^{4-}$—AuNPs/P-oPDA biosensor on combined electrode-6 for (a) 454.5, (b) 871.2, (c) 1255.8 and (d) 1613 µM phosphate concentrations. Monomer solution/conditions and measurement conditions are the same as mentioned for FIG. 45A.

Figure 45D:
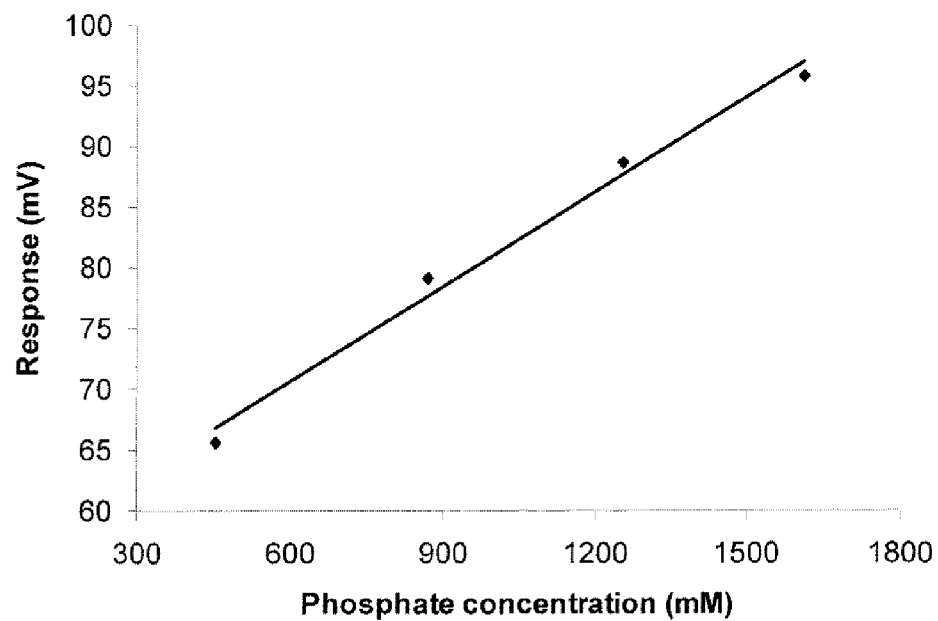

FIG. 45D is a graphical representation of a typical potentiometric calibration curve obtained with PPy-XOD-PNP—Fe(CN)$_6^{4-}$—AuNPs/P-oPDA biosensor on modified combined electrode probe-6 for increasing phosphate concentrations. Monomer solution/conditions and measurement conditions are the same as mentioned in FIG. 45A.

Figure 46:
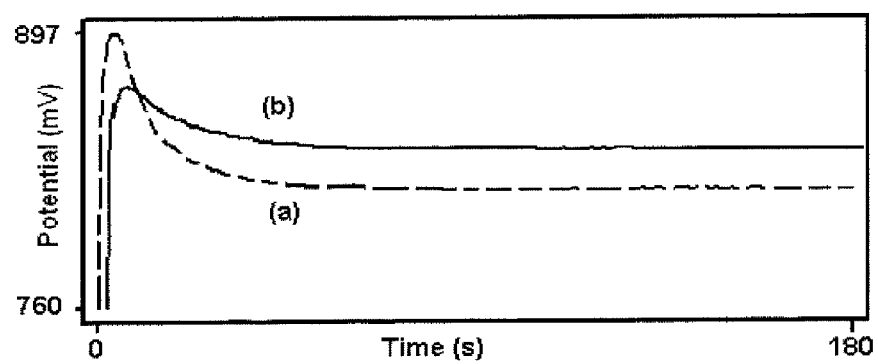

FIG. 46 shows chronopotentiograms for the galvanostatic growth of (a) combined PPy-AuNP—NaR—NADH, and (b) PPy-NaR—NADH films on combined electrode. Film formation conditions; NaR=0.5 U/mL. PPy=0.5 M, KCl=0.2 M, current density=0.5 mA cm$^{-2}$, polymerisation period 3 mins and NADH=0.4 mM.

Figure 47:
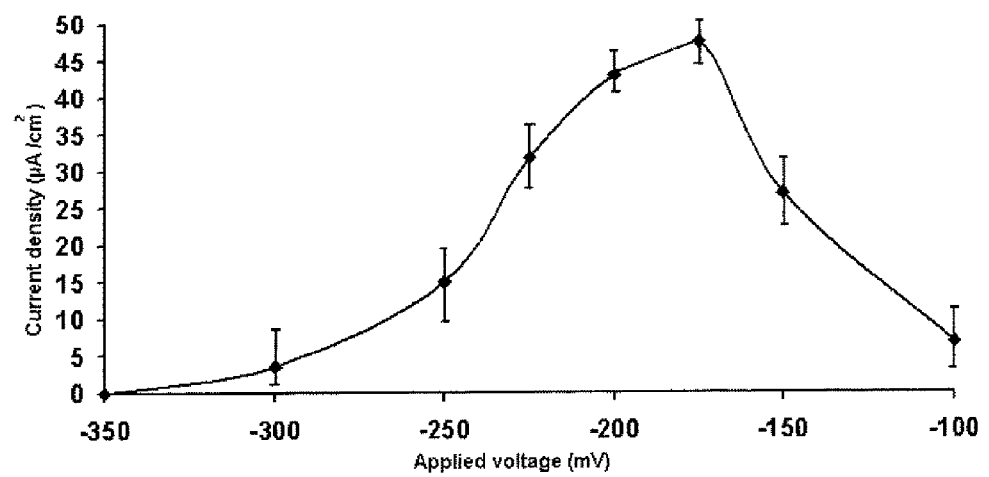

FIG. 47 is a graphical representation showing the optimization of measurement applied potential for amperometric determination of nitrate by PPy-NaR—NADH biosensor. Polymerisation conditions: PPy=0.3M, KCl=0.2 M, NaR=0.5 U. AuNP=0.0005% and NADH=0.4 mM. The nitrate response was measured in 0.1 M phosphate buffer of pH 7.3. [NO3-] was 500 µM.

Figure 48:
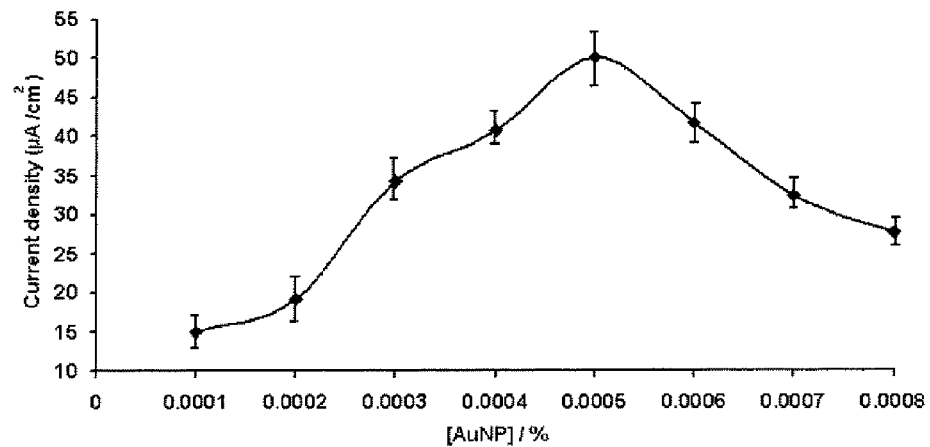

FIG. 48 is a graphical representation showing the influence of gold-nanoparticles concentration on the amperometric response for 500 µM of nitrate. The nitrate response was measured at −175 mV in 0.1 M phosphate buffer of pH 7.3. Other film formation conditions were same as in FIG. 47. [NO3-] was 500 µM.

Figure 49:
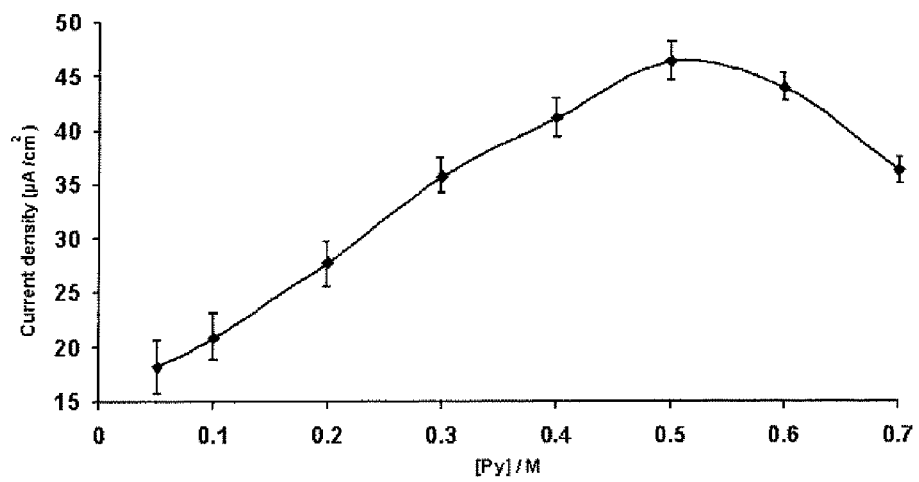

FIG. 49 is a graphical representation showing the optimization of pyrrole concentration for the formation of PPy-NaR—NADH film. Polymerisation conditions are same as expresses in FIG. 47 except various pyrrole concentrations were used for the growth of PPy-AuNP—NaR—NADH film. [NO3-] was 500 µM. Measurement Conditions as for FIG. 48.

Figure 50:
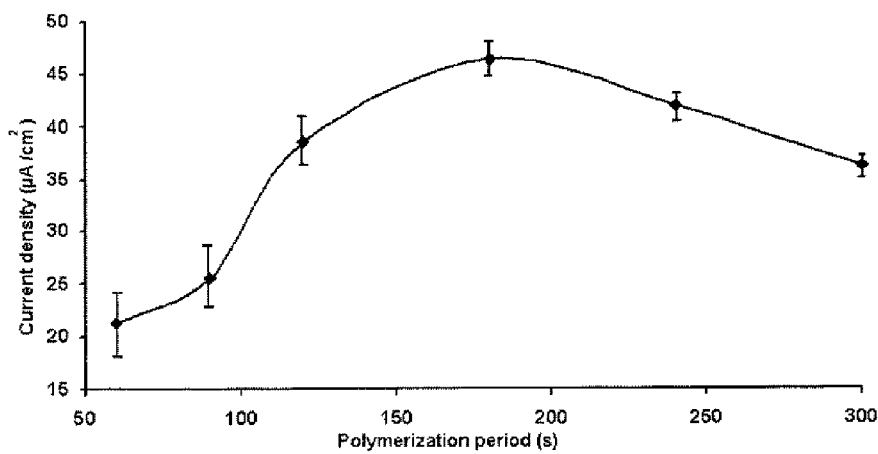

FIG. 50 is a graphical representation showing the influence of polymerisation period used for the growth of PPy-AuNP—NaR—NADH film on the amperometric response for nitrate. Polymerisation conditions are same as in FIG. 47, except various polymerisation periods for the growth of PPy-AuNP—NaR—NADH film. [NO3-] was 500 µM. Measurement Conditions as for FIG. 48.

Figure 51:
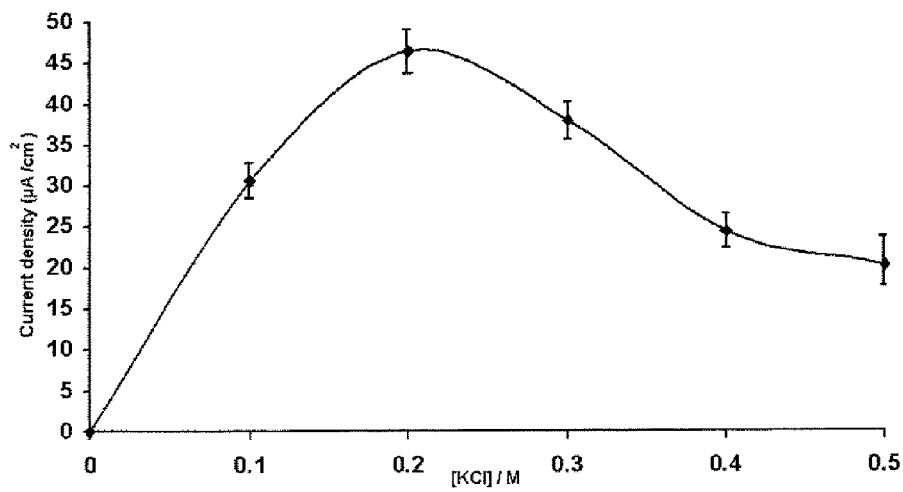

FIG. 51 is a graphical representation showing the effect of KCl concentration used for the growth of PPy-Au—NaR—NADH film on the amperometric response for nitrate. Polymerisation conditions are same as in FIG. 47 except, KCl concentration was varied for the growth of PPy-AuNP—NaR—NADH film. [NO3-] was 500 µM. Measurement Conditions as for FIG. 48.

Figure 52:
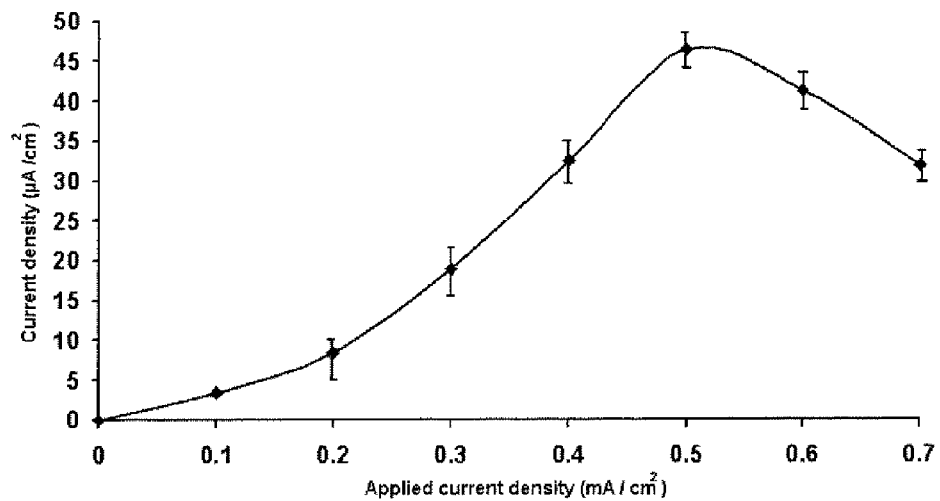

FIG. 52 is a graphical representation showing the effect of current density for the growth of PPy-AuNP—NaR—NADH film on the amperometric response for nitrate. Polymersation conditions are same as expressed in FIG. 47 except current density was varied for the growth of PPy-AuNP—NaR—NADH film. [NO3-] was 500 µM. Measurement Conditions as for FIG. 48.

Figure 53:
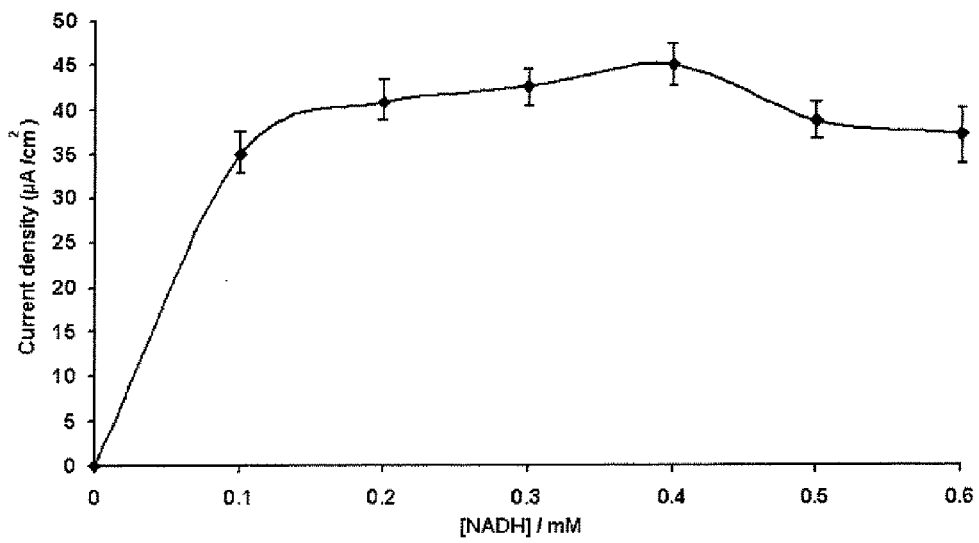

FIG. 53 is a graphical representation showing the influence of NADH concentration for the growth of PPy-AuNP—NaR—NADH film on the amperometric response for nitrate. Polymerisation conditions are same as expressed in FIG. 47 except NADH concentration was varied for the growth of PPy-AuNP—NaR—NADH film. [NO3-] was 500 µM. Measurement Conditions as for FIG. 48.

Figure 54:
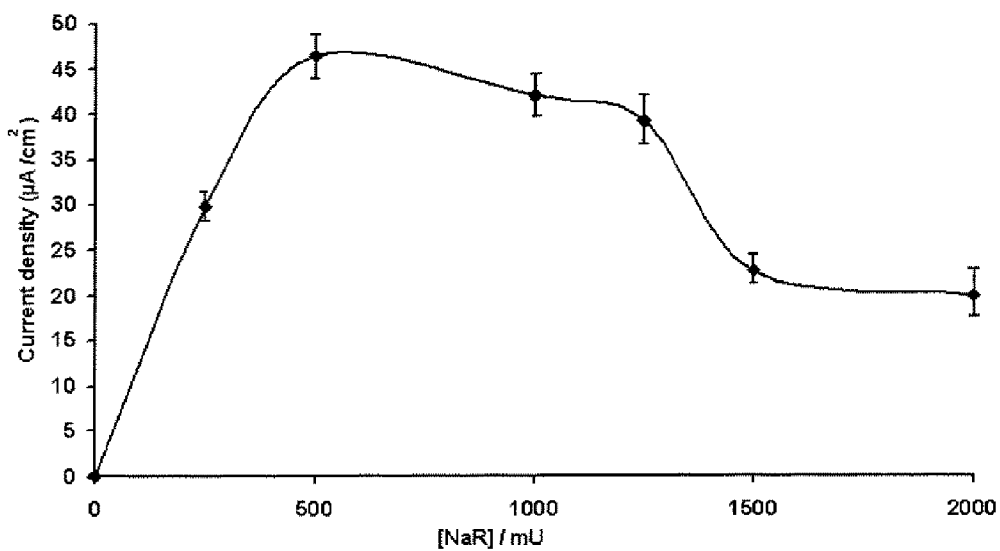

FIG. 54 is a graphical representation showing the influence of NaR concentration for the growth of PPy-AuNP—NaR—NADH film on the amperometric response for nitrate. Polymerisation conditions are same as expressed in FIG. 47 except NaR concentration was varied for the growth of PPy-AuNP—NaR—NADH film. [NO3-] was 500 µM. Measurement Conditions as for FIG. 48.

Figure 55:
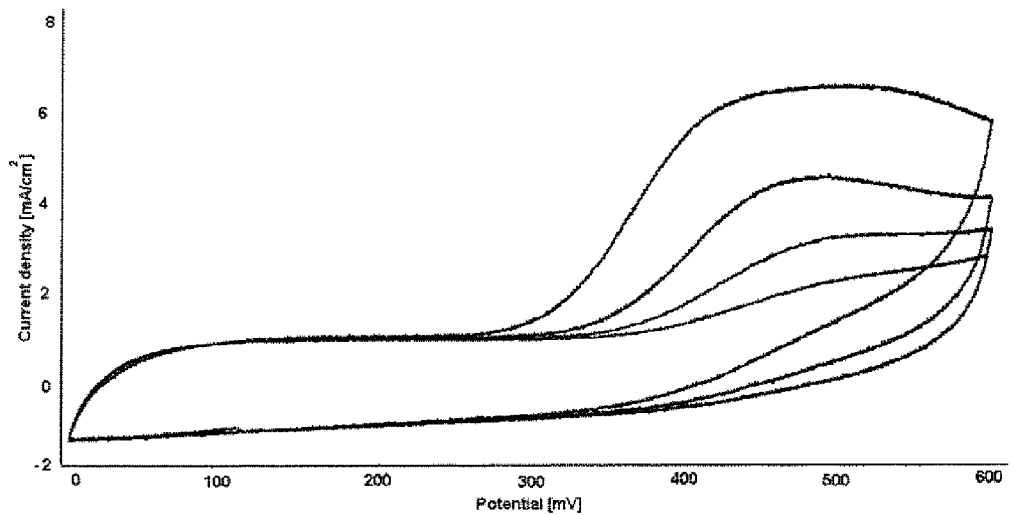

FIG. 55 shows a cyclic Voltammogram for the growth of P-oPDA film on the surface of PPy-AuNP—NaR—NADH electrode. Film formation conditions; oPDA=50 mM, KCl=0.3 M, Barbitone buffer 0.05 M.

Figure 56:
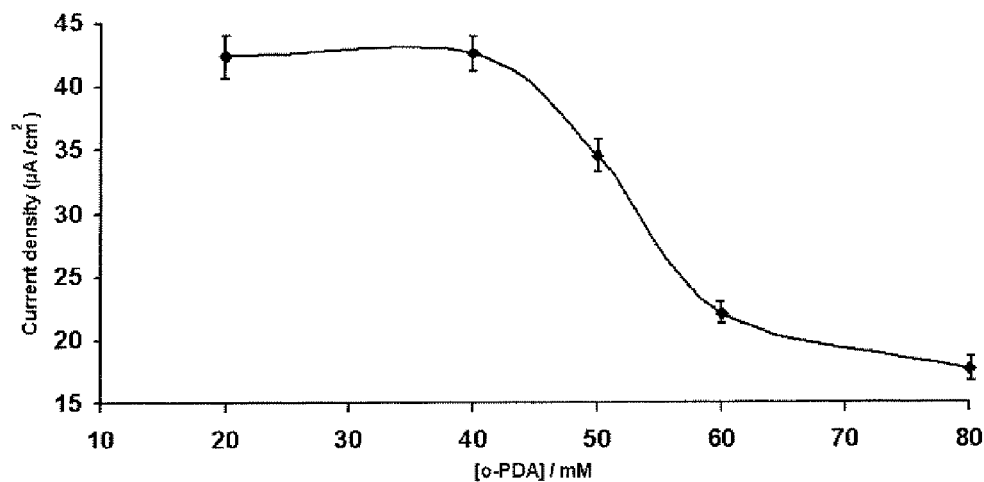

FIG. 56 is a graphical representation showing the optimization of oPDA concentration for the formation of outer P-oPDA layer on the PPy-AuNP—NaR—NADH electrode. Following polymerisation conditions were used: oPDA 50 mM, barbitone buffer 0.05 M and KCl 0.3 M. [NO3-] was 500 µM. Measurement Conditions as for FIG. 48.

Figure 57:
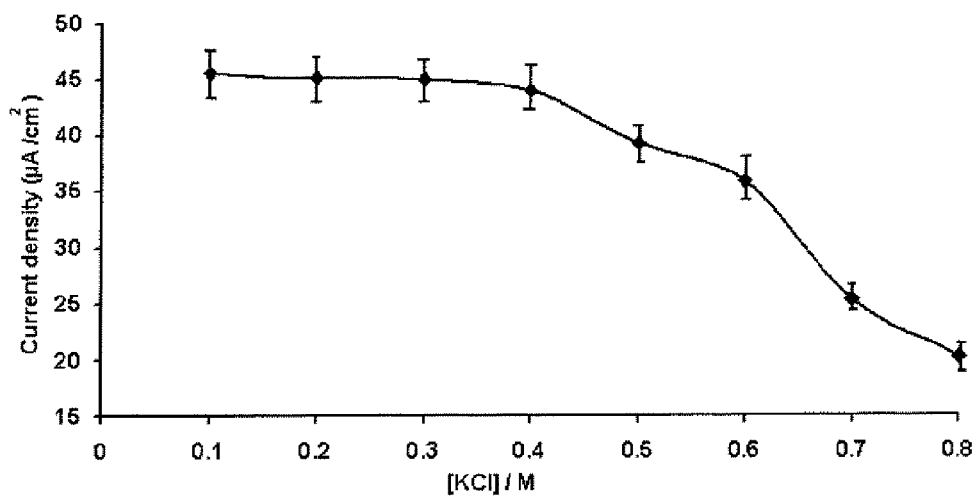

FIG. 57 is a graphical representation showing the optimization of KCl concentration for the formation of outer oPDA layer on the PPy-NaR—NADH electrode. Polymerisation conditions were the same as used in FIG. 56 except different KCl concentrations were used for P-oPDA layer. [NO3-] was 500 µM. Measurement Conditions as for FIG. 48.

Figure 58:
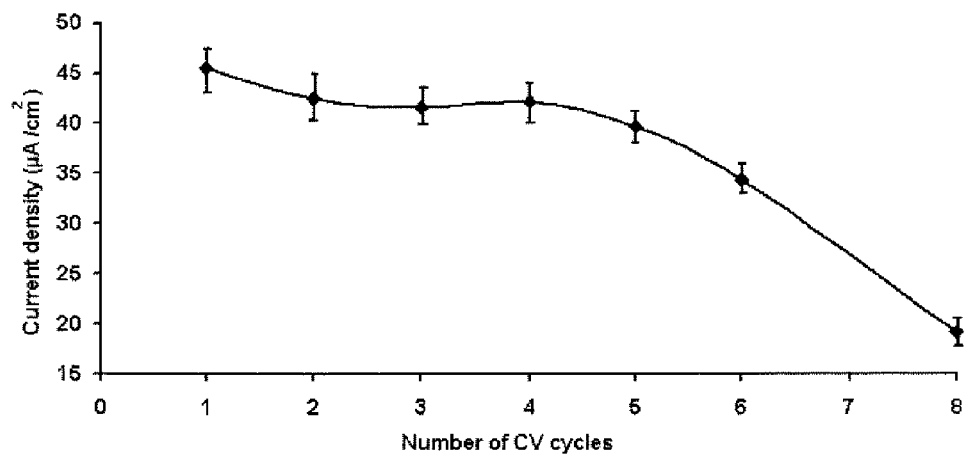

FIG. 58 is a graphical representation showing the influence of number of CV cycles for the growth of P-oPDA layer on the surface of PPy-AuNP—NaR—NADH electrode. Polymerisation conditions were same as shown in FIG. 56 except different number of cycles were used. [NO3-] was 500 µM. Measurement Conditions as for FIG. 48.

Figure 59:
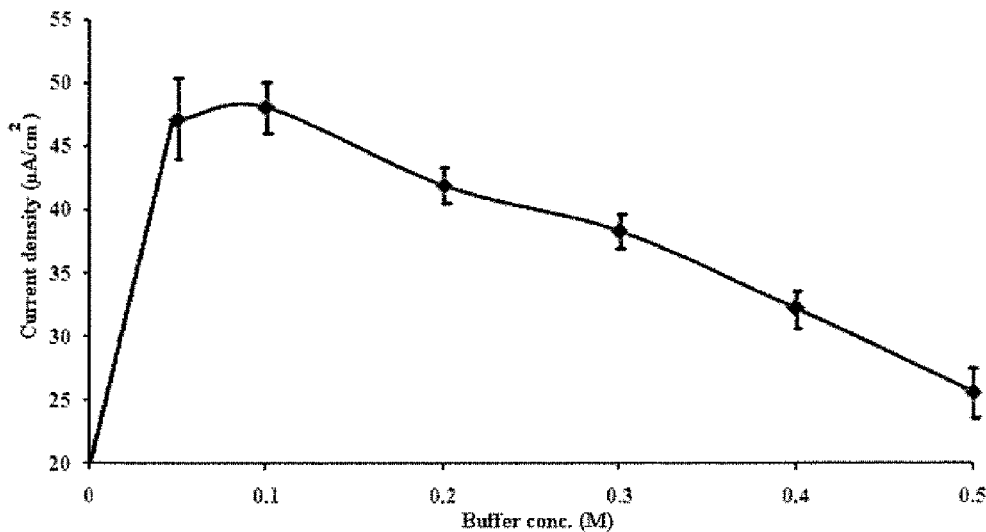

FIG. 59 is a graphical representation showing the influence of buffer concentration on the amperometric response for nitrate obtained with optimised PPy-AuNP—NaR—NADH/P-oPDA nitrate biosensor. Film formation condition; PPy=0.3M, AuNP=0.0005%, KCl=0.2 M, NaR=0.5 U and NADH=0.4 mM. The response for 500 µM of nitrate response was measured in 0.2 M phosphate buffer of pH 7.3, using other conditions given in FIG. 48.

Figure 60:
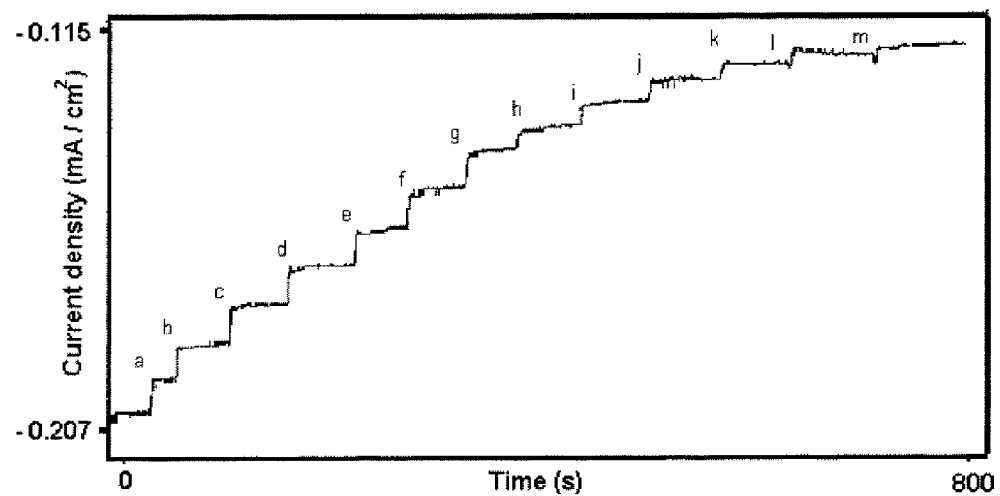

FIG. 60 shows the amperometric response obtained for nitrate at −200 mV. The response for successive additions of nitrate was observed in a solution containing 0.1M phosphate buffer of pH 7.3 (a) 119 (b) 227 (c) 326 (d) 416 (e) 500 (f) 577 (g) 648 (h) 714 (i) 776 (j) 833 (k) 887 (1) 938 (m) 985 µM nitrate.

Figure 61:
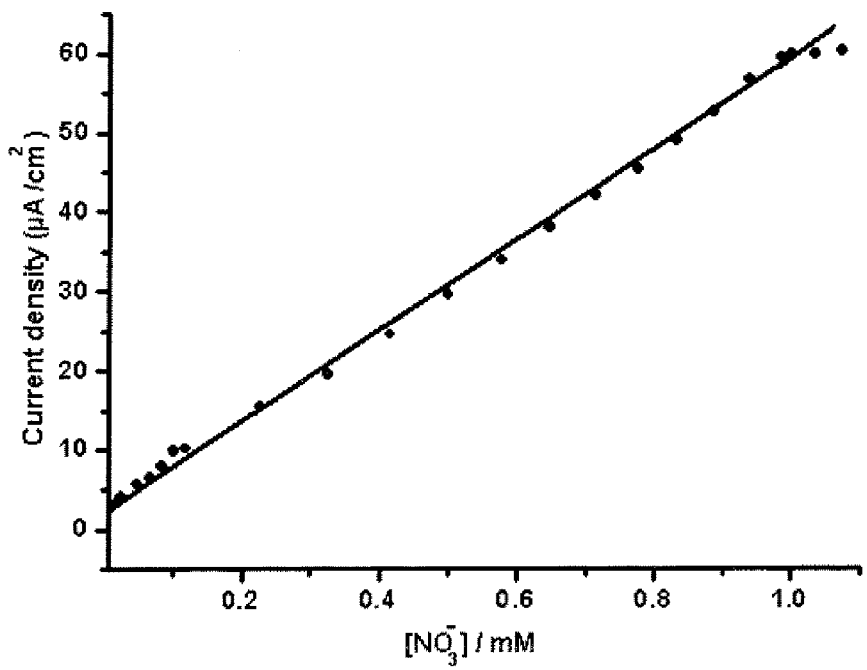

FIG. 61 is a graphical representation showing a typical calibration plot obtained for nitrate with the combined PPy-AuNPNaR—NADH/P-oPDA biosensor.

Figure 62:
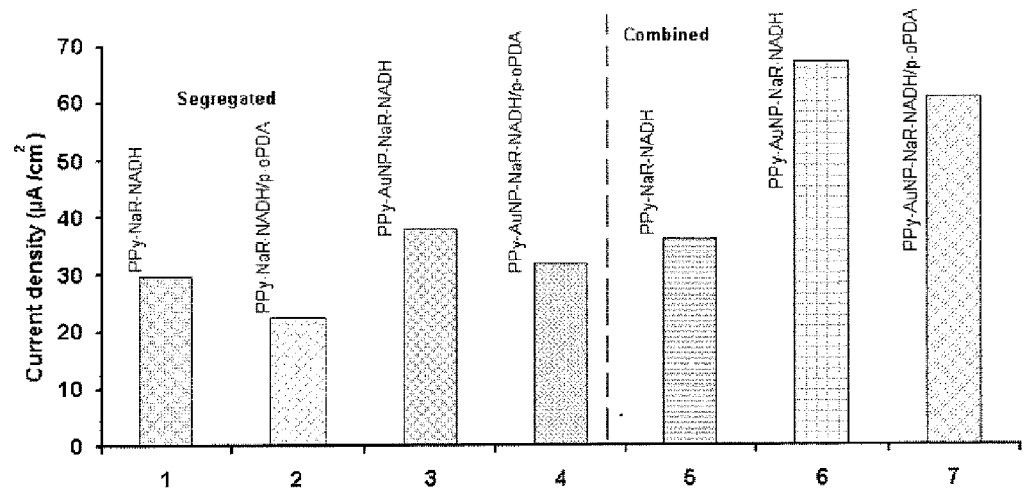

FIG. 62 shows a comparison of amperometric response for 500 µM of nitrate with all the biosensors fabricated to date.

Figure 63:
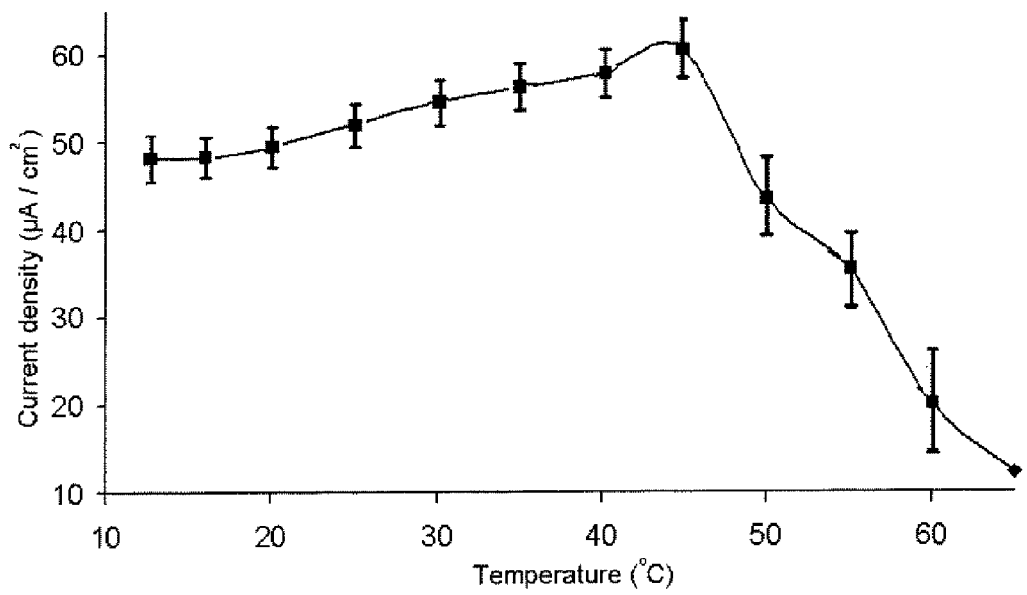

FIG. 63 is a graphical representation showing the influence of temperature on the nitrate response obtained with PPy-AuNP—NaR—NADH/P-oPDA biosensor. The experimental conditions were the same as FIG. 48.

The invention will now be described with reference to the following Examples which illustrate some preferred aspects of the present invention. However, it is to be understood that the particularity of the following description of the invention is not to supersede the generality of the preceding description of the invention.

EXAMPLES

All chemicals were of analytical grade. Pyrrole was supplied by Aldrich (USA) distilled under vacuum before use and stored in the refrigerator after covering it with aluminium foil to prevent UV degradation and oxygen by air oxygen. Ortho-phenylenediamine (oPDA) (Sigma, USA) was used without additional purification and had white plate like fine crystals. 0.15 M of oPDA stock solution was prepared on deairated distilled water and kept in the dark bottle under nitrogen atmosphere in the refrigerator. All solutions were prepared with Milli-Q water. PNP and XOD were obtained from Sigma Aldrich and not purified further.

Reagents and Standard Solutions

Xanthine oxidase (XOD) (EC.1.2.3.2.2 Grade 1) from buttermilk, purine nucleoside phosphorylase (PNP) (EC.2.4.2.1), inosine, potassium ferrocyanide and pyrrole were obtained from Sigma-Aldrich. All other chemicals were of analytical reagent grade, unless specified otherwise, and all compounds used in the examples were prepared without further purification. The pyrrole was distilled under vacuum at 130° C. prior to use, and this was stored in an aluminium foil covered sample bottle in the freezer to prevent UV degradation until required for use.

Barbitone buffer stock solution (0.5 M, pH 7.8) was prepared by neutralising 0.5 M barbituric acid with 0.1 M sodium hydroxide. This was stored at 4° C. and diluted when needed. A 0.1 M sodium chloride solution was prepared by dissolving an appropriate amount (1.2 g) of NaCl in Milli-Q water. The volume was then adjusted to 250 mL. A stock solution of 0.25 M $K_4Fe(CN)_6$ salt was prepared by dissolving 1.0060 g of the salt in Milli-Q water. The volume was then adjusted to 10 mL. The volumetric flask was then placed in an ultrasonic-bath until the remaining crystal of the salt dissolved and the solution was clear. Note that $K_4Fe(CN)_6$ can also undergo UV degradation. The solution was therefore stored in the dark until required. Stock solution of XOD was prepared by adding 100 µL of Milli-Q water to 100 units XOD bottle, while stock solution of PNP was also prepared by adding 200 µL of Milli-Q water to 200 unit PNP bottle. These enzyme stock solutions were stored in the refrigerator and freezer respectively, until required. Phosphate stock solution (0.5 M) was stored in the refrigerator and was diluted when necessary to give the required standard concentration.

Example 1

1.1 Phosphate Sensor Fabrication

Electrochemical deposition of a polypyrrole purine nucleoside phosphorylase—xanthine oxidase (PPy-PNP—XOD) film was performed with a three electrode cell, comprising an Ag/AgCl (3M KCl) reference electrode, a platinum wire auxiliary electrode and a platinum disk working electrode with a surface area of 12.6 mm². A potentiostat/galvanostat was employed for electropolymerisation of polypyrrole (PPy) film as well as for potentiometric measurements. Immobilisation of xanthine oxidase (XOD) and purine nucleoside phosphorylase (PNP) into PPy was carried out on a platinum electrode by galvanostatic polymerisation.

1.2 Electrochemical Characterisation

An increase in polymerisation potential was observed within the first fifteen seconds due to the activation of the polymerisation process. Polymerisation then commenced after this period and subsequently resulted in the deposition of a conductive PPy-PNP—XOD layer on the platinum electrode. As the film thickness continues to grow the potential stabilised and showed only slight decrease with the film growth which is consistent with the increase in conductivity. The amount of XOD and PNP incorporated into the PPy matrix increased with increasing film thickness.

The cyclic voltammograms obtained for the PPy-PNP—XOD composite film at a scan rate of 50 mV/s gave an oxidation peak and two distinct reduction peaks. The oxidation peak and the first reduction peak appeared at potentials that are expected of the characteristic oxidation/reduction couple for a PPy film. While the additional reduction peak was due to the incorporation of XOD and PNP into the polymer film.

1.3 Potentiometric Detection of Phosphate

Potentiometric measurements were performed (at zero current) in a two electrode cell. This mode of detection was used for initial investigations because of its quick response and ease of use.

The change in potential caused by the presence of phosphate is based on the reactions shown in Scheme 1. PNP reacts with ionosine in the presence of phosphate ions (Pi) to generate hypoxanthine which is then converted to uric acid via a two-step process catalysed by XOD. Consequently, two molecules of $H_2O_2$ are produced during this process. The XOD acts in these reactions as a biological amplifier, generating 3 molecules of electroactive species (2 molecules of peroxide and 1 molecule of uric acid) for 1 molecule of phosphate. The peroxide and uric acid generated results in a decrease in potential at the PPy-PNP—XOD electrode and the magnitude of the potential change is proportional to the concentration of phosphate present.

SCHEME 1

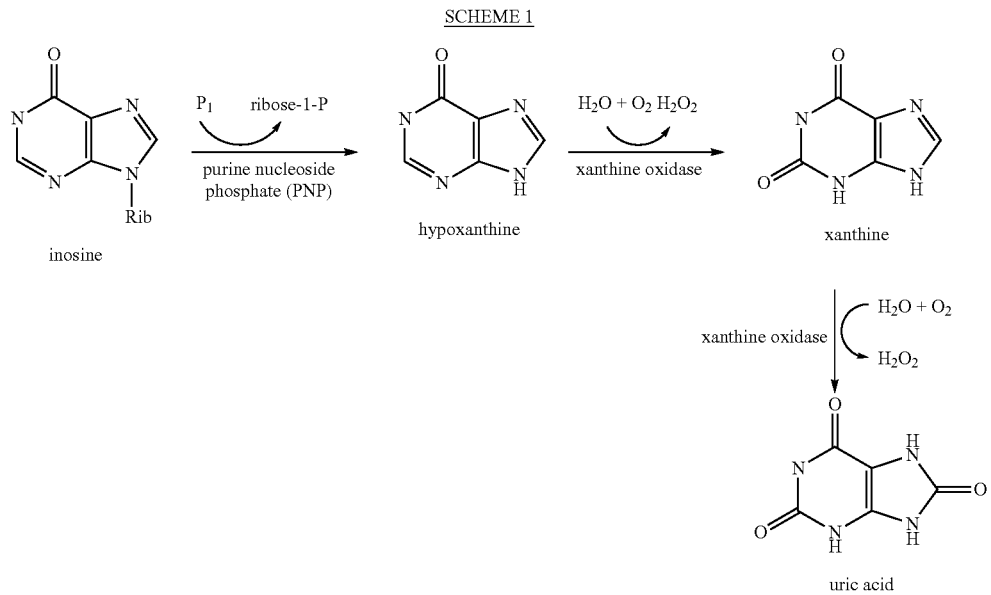

1.4 Optimisation of Polymerisation Conditions

To obtain reliable and sensitive response to phosphate with the PPy-PNP—XOD electrode, the influence of a number of parameters was investigated. A summary of the results obtained for the optimisation of the various parameters is given in Table 2.

TABLE 2

Optimised conditions for nanofabrication of PPy-XOD-PNP films for potentiometric detection

| Optimised Parameter | Optimised value |
| --- | --- |
| Pyrrole concentration | 0.5 M |
| XOD concentration | 6 U/mL |
| PNP concentration | 48 U/mL |
| $K_4Fe(CN)_6$ concentration | 50 mM |
| Current density | 0.5 mA/cm² |
| Polymerisation period | 120 seconds |

1.5 Optimisation of Film Thickness

Figure 4:
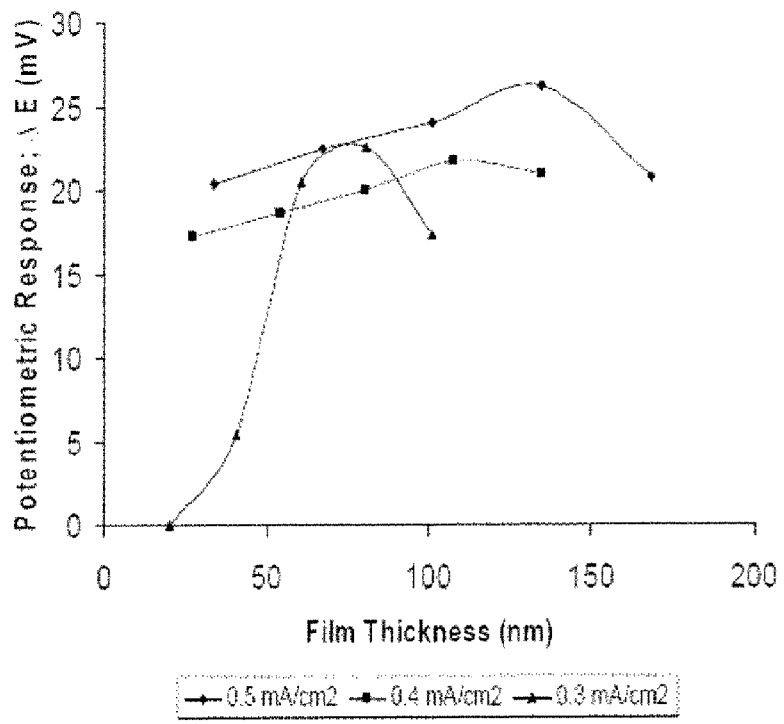
FIG. 4 is a graphical representation of the influence of PPy-PNP—XOD film thickness obtained at three different densities on phosphate (323 µM) potentiometric response. Measurement solution comprised of 0.05 M barbitone buffer, 10 mM inosine and 0.1 M NaCl. Polymerisation conditions: [Py] 0.5 M, [$K_4Fe(CN)_6$] 40 mM, [PNP] 48 U/mL, [XOD] 6 U/mL.

To establish the effect of increasing film thickness, within the nanometer range, PPy-PNP—XOD films 20 to 170 nm in thickness were prepared and phosphate sensitivity determined. FIG. 4 demonstrates that the nature of the film formed is dependent upon the applied current density used for the film formation. As can be seen from FIG. 4, the sensitivity of the phosphate response obtained for films formed with an applied current density of 0.3 mA/cm² increased with increasing film thickness up to 80 nm and decreased beyond that thickness. In contrast, the sensitivity of the phosphate response obtained for films formed with an applied current density of ≥0.4 mA/cm² only increased slightly with increasing film thickness up to 108 nm for 0.4 mA/cm² and 135 nm for 0.5 mA/cm². These observations suggest that the nature and morphology of the nanometer thick films may be influenced significantly by the applied current density. However, the sensitivity obtained at the optimum film thickness in each case is reasonably close, ranging from 20-25 mV for potentiometric measurement. Overall, the highest sensitivity was obtained with the 135 nm thick PPy-PNP—XOD film formed at an applied current density of 0.5 mA/cm² for a polymerisation period of 120 seconds. However, there was not much difference in the sensitivity obtained for films grown with an applied current density of 0.5 mA/cm², therefore a polymerisation period of 30-60 seconds was used. The PPy-PNP—XOD film thickness obtained for such short polymerisation period was within 30-70 nm.

1.6 Optimised Conditions for Nanofabrication

Figure 5:
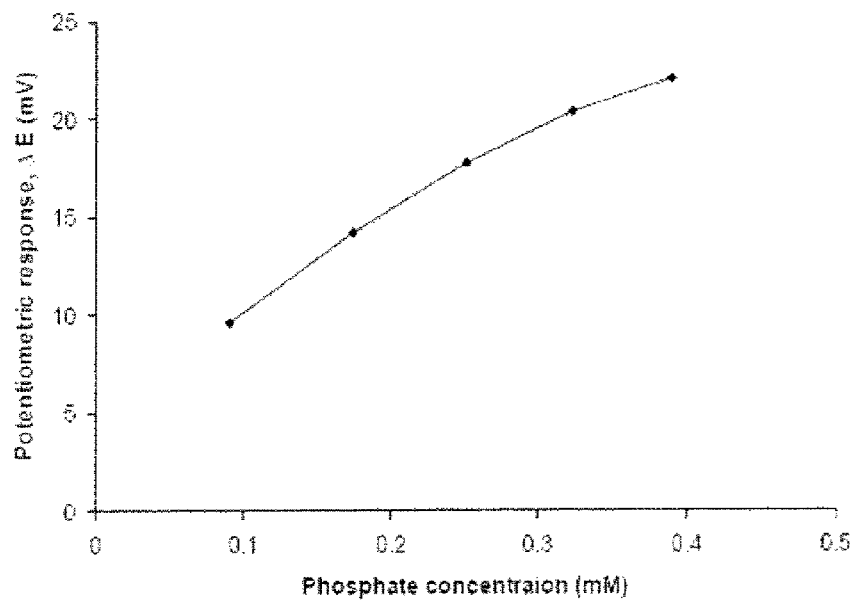
FIG. 5 is a graphical representation of the calibration curve obtained for phosphate with a 34 nm thick PPy-XOD-PNP film. Measurement solution comprised of 0.05 M barbitone buffer. 10 mM inosine and 0.1 M NaCl. Polymerisation conditions: [Py] 0.5 M, [K$_4$Fe(CN)$_6$] 40 mM, [PNP] 48 U/ml, [XOD] 6 U/ml, polymerisation period 30 seconds, current density 0.5 mA/cm$^2$.

The optimised conditions for nanofabrication of 30-70 nm thick PPy-PNP—XOD films were 0.5 M pyrrole, 40 mM $K_4Fe(CN)_6$, 48 U/mL PNP, 6 U/mL XOD, a current density of 0.5 mA/cm² and a polymerisation period of 30-60 seconds. The phosphate response increased with increasing concentration at a 34 nm PPy-PNP—XOD electrode. A calibration curve obtained at these optimised conditions is shown in FIG. 5.

Example 2

PPy-PNP—XOD/P-oPDA Bilayer 2.1 Formation of the PPy-PNP—XOD/P-oPDA Bilayer

A protective thin film of poly-orthophenylenediamine (P-oPDA) was formed on top of the PPy-PNP—XOD inner layer with a steady potential sweep at a constant scan rate. The electrode potential was cycled between 0 and 800 mV at scan rates of 30, 50, 75 and 100 mV/s for 2 to 20 scans. The monomer solution contained 50 mM, oPDA, 0.05 M barbitone buffer and 0.5 M KCl. The PPy-PNP—XOD inner layer was 67 nm thick and was formed by electropolymerisation from a solution containing 0.5 M Py, 40 mM $K_4Fe(CN)_6$, 48 U/mL PNP and 6 U/mL XOD at an applied current density of 0.5 mA cm² and a polymerisation period of 60 seconds. The P-oPDA film thickness increased with increasing number of scans, but decreased with increasing scan rate. The first anodic peak in the cyclic voltamagram is associated with oPDA oxidation, while the second peak was attributed to the polymerisation process. The rapid decline of the second anodic peak current, within the first four scans is indicative of the rapid formulation of the insulating P-oPDA film.

2.2 Optimisation of Polymerisation Parameters

Optimisation of the scan rate, number of scans, oPDA concentration and barbitone buffer concentration was undertaken to provide the optimum phosphate response with the PPy-PNP—XOD/P-oPDA bilayer electrode.

2.2.1 oPDA Concentration

Figure 6:
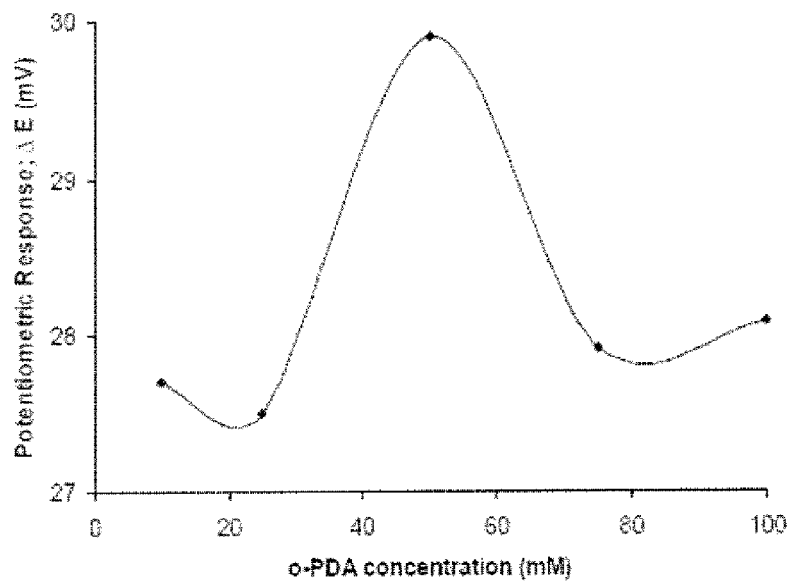
FIG. 6 is a graphical representation of the effect of oPDA concentration used for the growth of P-oPDA layer on the sensitivity of the PPy-PNP—XOD/P-oPDA sensor on phosphate response. Measurement solution contained 0.05 M barbitone buffer, 10 mM inosine, 0.1 M NaCl and 323 μM phosphate. Polymerisation conditions for PPy-XOD-PNP/P-oPDA sensor were the same as described in part 2.1 of Example 2, except that various oPDA concentrations were used for electrochemical polymerisation of P-oPDA over PPy-XOD-PNP layer at a scan rate of 50 mV/s.

FIG. 6 shows that the sensitivity of the phosphate response increased with increasing oPDA concentration up to 50 mM. Given that the overall potential change for a 10-fold increase in oPDA concentration from 10 to 100 mM was only about 2 mV, it appears that the monomer concentration did not have a significant effect on the sensitivity of the PPy-PNP—XOD/P-oPDA bilayer electrode. This is expected for an insulating layer, such as P-oPDA, because of its self-limiting growth.

2.2.2 Scan Rate

Figure 7:
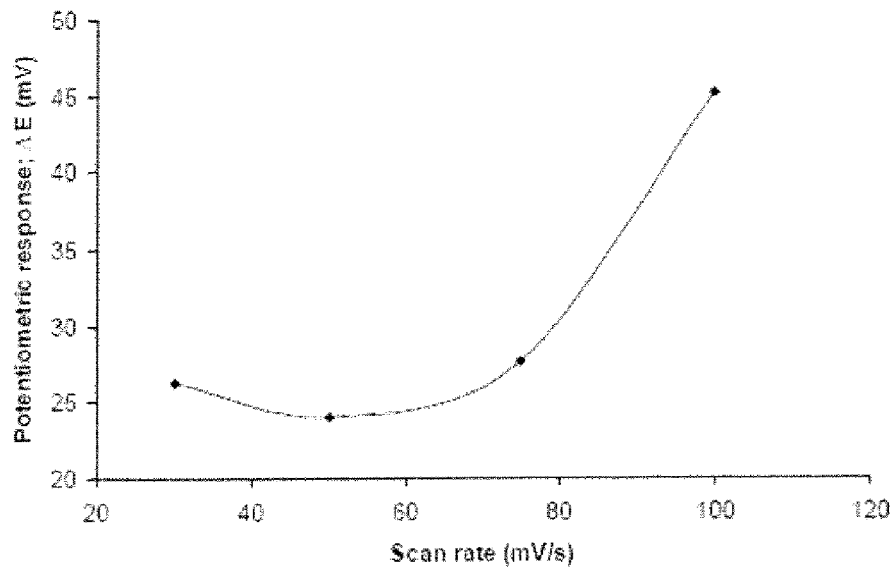
FIG. 7 is a graphical representation of the influence of the scan rate used for the potentiodynamic polymerisation of oPDA on the sensitivity of PPy-PNP—XOD/P-oPDA sensor to phosphate. Measurement solution contained 0.05 M barbitone buffer, 10 mM inosine, 0.1 M NaCl and 323 μM phosphate. Polymerisation conditions for PPy-PNP—XOD/P-oPDA sensor were as described in part 2.1 of Example 2, except that different scan rates were applied for electrochemical polymerisation of P-oPDA over the PPy-XOD-PNP layer.

The influence of scan rate on the nature of the electrochemically deposited P-oPDA outer layer and, hence, on the sensitivity of the PPy-PNP—XOD/P-oPDA bilayer electrode to phosphate is shown in FIG. 7. As the thickness of P-oPDA layer increases with decreasing scan rate, the sensitivity of the bilayer electrode to phosphate also decreased. An increase in film thickness increases the diffusion barrier between phosphate and the inner PPy-PNP—XOD layer, thus reducing sensitivity. It is also possible that the increased P-oPDA film thickness modifies the orientation of the active sites of the enzymes and, consequently reduces the sensitivity of the phosphate response. It can be seen from FIG. 7 that the optimum scan rate for the growth of the outer layer was 100 mV/s.

2.2.3 Inner PPy-PNP—XOD Film Thickness

The influence of the inner layer thickness on the sensitivity of phosphate response obtained with the bilayer electrode was investigated by using four different PPy-PNP—XOD films with thickness ranging from 34 to 67 nm. Even when the chosen film thicknesses were reasonably close (e.g. for 67 nm, 54 nm and 61 nm), there were considerable differences in the sensitivity obtained for the phosphate response. The observed differences appeared to be associated with the applied current density employed for the formation of the inner layer. The PPy-PNP—XOD inner layer, grown with an applied current density of 0.4 mA cm² to achieve a film thickness of 54 nm, gave the best sensitivity for the phosphate response. Even when the same current density is employed, the nature of the film still appeared to be influenced by the chosen polymerisation period and associated with the difference in film thickness. In this case, a thinner film (34 nm) gave a slightly better sensitivity for the phosphate response. However, even though the best sensitivity was obtained with the 54 nm film, full coverage of the platinum working electrode surface with the inner PPy-PNP—XOD layer was not accomplished. Similar observations were made for the 61 nm thick film formed with the applied current density of 0.3 mA cm². Therefore to ensure adequate surface coverage with the inner layer, the 67 nm thick PPy-PNP—XOD film formed at an applied current density of 0.5 mA cm² was employed in all subsequent bilayer electrodes. It was also observed that the P-oPDA layer formed on top of the PPy-PNP—XOD inner layer was relatively thinner. The growth of P-oPDA is self-limited by its non-conducting nature and it is known to form a uniform film thickness of about 10 nm [Vidal et al., Sensors and Actuators, B57, (1999) 219-226].

2.2.4 Scan Number for P-oPDA Growth

The sensitivity of the phosphate response is influenced by the number of scans employed for the potentiodynamic growth of the outer P-oPDA layer. The initial growth of the outer layer with 2-4 scans resulted in a slight decline in the sensitivity of the phosphate response due to the increased barrier caused by the more intact top layer. However, beyond 4 scans it appeared that the nature of the outer layer changed, resulting in an increased phosphate response with outer layers grown with up to 10 scans. Beyond this number of scans, the sensitivity of the phosphate response seems to stabilise. These observations suggest that the noted improvement in the phosphate response with the growth of the outer P-oPDA layer with >4 scans was due to:
 (a) the containment and retention of PNP and XOD in the inner layer by the outer P-oPDA layer, enabling more catalytic products to reach the platinum electrode; and/or
 (b) change in the nature of outer layer (e.g. change in porosity) formed with >4 scans, enabling more phosphate to reach the inner layer.

For the above reasons, the optimum number of scans chosen for the formation of the P-oPDA outer layer in all subsequent investigations was 10 at a scan rate of 100 mV/s.

Figure 8:
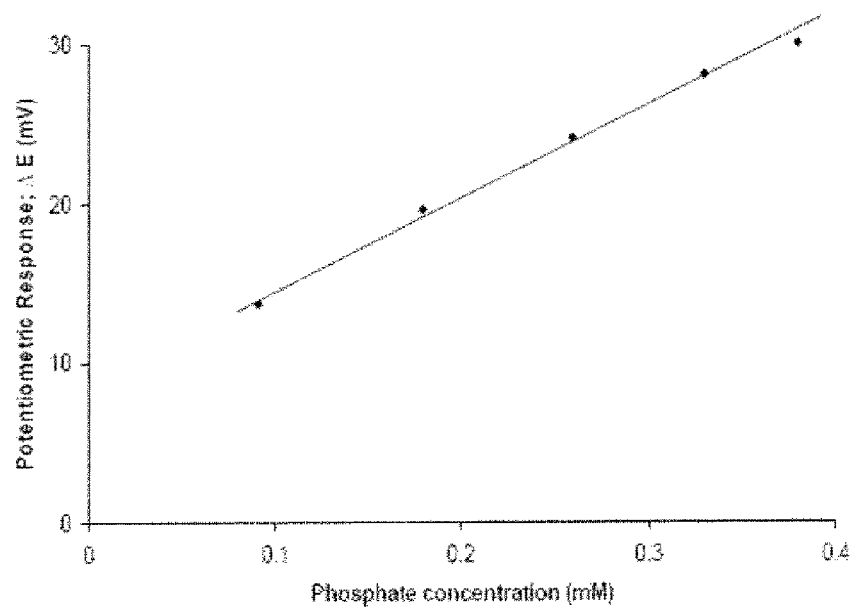
FIG. 8 is a graphical representation of a typical calibration curve obtained with a PPy-PNP—XOD/P-oPDA sensor. Measurement solution contained of 0.05 M barbitone buffer, 10 mM inosine and 0.1 M NaCl. Polymerisation conditions for PPy-PNP—XOD and P-oPDA were the same as described in part 2.1 of Example 2.

The optimised conditions established for fabrication of the bilayer electrode were 67 nm thick PPy-PNP—XOD inner layer and a 10 nm P-oPDA layer formed with 10 scans at 100 mV/s. The phosphate response increased with increasing phosphate concentration. Compared with the PPy-PNP—XOD layer alone, the measured potentials were substantially lower due to the presence of the non-conductive P-oPDA outer layer. However, the potential change caused by the addition of phosphate was greater with the bilayer electrode. FIG. 8 provides a calibration curve at varying concentrations of phosphate. As can be seen in FIG. 8 compared with FIG. 5, the sensitivity obtained for phosphate with the bilayer electrode was substantially higher than with the single layer electrode. Further optimisation to provide a detection limit of ≤1 µM may be realised with the bilayer electrode.

Example 3

PPy-PNP—XOD/BSA-GLA Bilayer

An electrode was prepared with a PPy-PNP—XOD polymeric film as outlined in Example 2. 1.3 µL of a mixture of 1.4-6.8% w/v bovine serum albumin BSA and 0.5-4.5% w/v glutaraldehyde (GLA) was spread over the PPy-PNP—XOD polymeric film. The outer layer was left to dry for 30 minutes allowing the coating to harden and gelatinise. The electrode was then washed under a stream of Milli-Q water to remove any loosely bound molecules. The measurement solution contained 0.05 M barbitone buffer, 10 mM inosine and 0.1 M NaCl.

Figure 9:
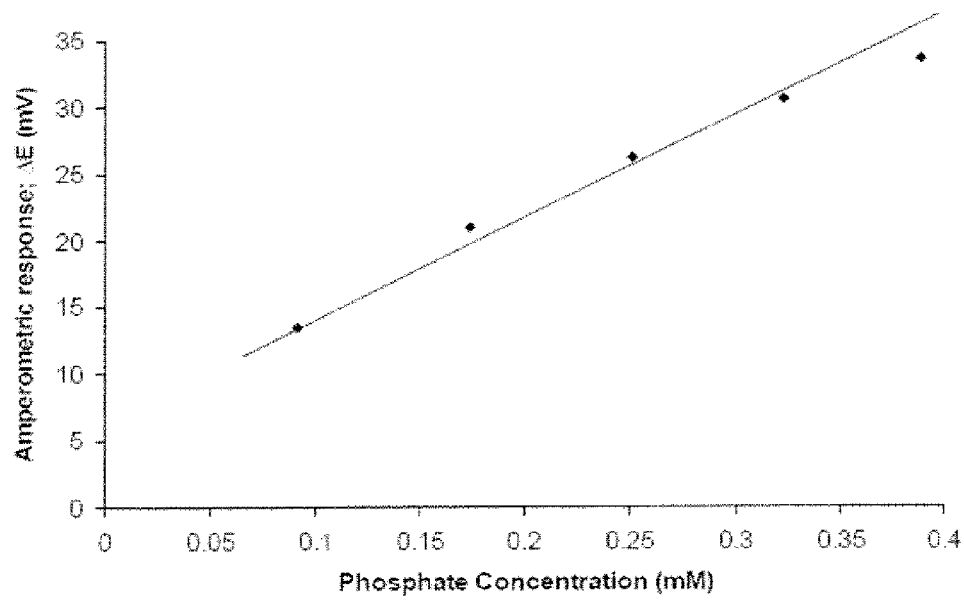
FIG. 9 is a graphical representation of the calibration curve obtained with a PPy-PNP—XOD/BSA-GLA bilayer sensor for phosphate. Measurement solution contained 0.05 M barbitone buffer. 10 mM inosine and 0.1 M NaCl. Conditions for formation of inner and outer layers were as described in part 2.1 of Example 2.

The PPy-PNP—XOD/BSA-GLA bilayer electrode gave sensitive responses to phosphate concentrations comparable to those obtained with PPy-PNP—XOD/P-oPDA bilayer electrodes. FIG. 9 provides the calibration curve for the PPy-PNP—XOD/BSA-GLA bilayer electrode showing phosphate response increased linearly with increasing phosphate concentration.

Example 4

PPy-GOx/P-oPDA Bilayer

Chemicals and Reagents

All chemicals were of analytical grade unless specified otherwise. Glucose oxidase (GOx) (344 units per mg of protein from *Aspergillus niger*), Peroxidase (240 purpurogallin units per mg solid form Horseredish) and o-Dianisidine dihydrochloride were obtained from Sigma (USA) and used as received. Pyrrole was supplied by Aldrich (USA) and was distilled before use. The distilled pyrrole was stored in the refrigerator under nitrogen atmosphere after covering container with aluminium foil to prevent UV degradation and air oxidation. Ortho-phenylenediamine (Sigma, USA) was used without additional purification and had white plate like fine crystals. 0.15 M of oPDA stock solution was prepared on deaerated distilled water and kept in the dark bottle under nitrogen atmosphere in the refrigerator. All solutions were prepared with Milli-Q water. β-D-glucose stock solution (0.5 M) prepared by dissolving 0.05 M phosphate buffer (pH 7) was stored in the refrigerator and was diluted when necessary to give required standard concentration. Phosphate (pH 7) and acetate (pH 5) buffers (0.05 M) were prepared by neutralising phosphoric and acetic acids, respectively, with sodium hydroxide.

Instrumentation

Electrochemical deposition of PPy and P-oPDA films was performed with a three electrode cell, comprising of a Ag/AgCl (3M KCl) reference electrode, a platinum gauze auxiliary electrode and a 1.0 or 1.5 mm platinum disc working electrode. A home-made potentiostat/galvanostat and Voltalab 40 voltammetry electrochemical laboratory (Radiometer Copenhagen) were employed for electropolymerisation of the films as well as for the potentiometric and amperometric measurements. Potentiometric measurements were performed in open circuit potential mode. BAS 100 B electrochemical analyser was used for electrochemical cleaning of Pt working electrodes by potentiodynamic cycling before the deposition of PPy or P-oPDA film. Amperometric measurements were carried out in three electrode electrochemical cell with the PPy-GOx/P-oPDA biosensor as a working electrode, platinum gauze and Ag/AgCl electrodes as auxiliary and reference respectively. The biosensor was polarised at constant potential (650 or 700 mV, potential of hydrogen peroxide oxidition) but resulting current density was measured with addition of increasing quantities of glucose to 0.05 M phosphate buffer solution during stirring of the solution, as well as from stagnant solution.

Photometric determination of $H_2O_2$ concentration in the solution as well as GOx activity was carried out on a Merck Nova 60 spectrophotometer at a wavelength of 500 nm in the "Kinetic" mode.

Electrode Preparation and Electropolymerisation

Platinum disc electrodes were polished with 0.3 µm alumina on a polishing pad, rinsed with distilled water, acetone, once again with water and ultrasonicated for 5 minutes in water. Following that 1.0 M $H_2SO_4$ was used to electrochemically clean the working Pt electrodes by cycling the electrode potential between −200 mV and 1450 mV versus Ag/AgCl at a sweep rate 50 mV/s for approximately 10 min, until a constant current-voltage relation was observed. Before electropolymerisation the 0.1 M pyrrole containing 70 U/mL GOx solution was purged with nitrogen for about 10 min to remove dissolved oxygen. Electropolymerisation of pyrrole was carried out galvanostatically at 0.1 mA/cm² in stagnant solutions in a three-electrode cell with Pt auxiliary and Ag/AgCl reference electrodes, and the charged passed was 30 mC/cm². Electropolymerisation of ortho-phenylenediamine was carried out in 0.05M oPDA solution in supporting electrolyte (0.05 M phosphate buffer pH 7 or 0.5 M KCl solution) after purging with nitrogen for 20 minutes, in potentiodynamic mode, at different scan rates and quantity of charge passed, from stagnant solution. After electropolymerisation, the electrodes were rinsed thoroughly with distilled water to remove any non polymerised substances (monomers) or loosely bound enzyme. Potentiometric and amperometric measurements were performed by placing the electrodes in a phosphate buffer solution. The resulting equilibrium potential or stationary current density were then measured for varying glucose concentration. After measurements sensors were rinsed with distilled water and stored in 0.05 M acetate buffer solution pH 5.1 in the refrigerator.

Photometric Determination of GOx Activity

GOx activity was measured photometrically according to Sigma assay procedure. 2.4 mL of 0.21 M o-dianisidine solution in 0.05 M acetate buffer (pH 5.1) was mixed with 0.5 mL 10% w/v glucose solution and 0.1 mL of peroxidase solution containing 60 purpurogalline units per ml. Different quantities of GOx solution (~0.5 U/mL) was added to this mixture and the absorbance (A) was measured at a wave length 500 nm in 1 cm silica photometric cell in "Kinetic" mode. The change of the absorbance with time (dA/dt) corresponds to GOx activity in the solution. GOx activity at different pH was measured according to the above procedure in 0.05 M acetate buffer (pH≤7) and 0.05 M phosphate buffer (pH≥7).

GOx activity in the PPy-GOx films was measured by placing the PPy-GOx electrode in 2 mL of 10% w/v glucose solution and stirred vigorously. A sample (~20 L) was taken at different times and analysed for the presence of hydrogen peroxide according to the above procedure with the only difference that $H_2O_2$ was produced in separate cell containing only glucose solution. From the slope (dA/dt) the activity of GOx in the sensor was determined and recalculated on the basis of surface area as $mU/cm^2$. It was assumed that the rate of hydrogen peroxide production is determined mainly by enzymatic reaction, but not by its diffusion from the film to the bulk of the solution.

Permeability of P-oPDA Layer to Ascorbic Acid and $H_2O_2$

The response of bare Pt and Pt covered with P-oPDA films of different thickness to the presence of hydrogen peroxide ($H_2O_2$) in the solution was investigated. It was evident that the films are highly permeable to $H_2O_2$ and the response was nearly instant as is the case for bare platinum. Furthermore, the response decreased with increase in film thickness, as evident for the films prepared with 50 and 100 $mC/cm^2$. However, it can be concluded that the product ($H_2O_2$) of glucose decomposition can permeate the P-oPDA film to the electrode and, hence, suggests that its use as an outer layer in a bilayer arrangement will enable adequate detection of glucose and other analyte for which hydrogen peroxide is a catalytic product.

The response of immobilised GOx electrodes to 0.5 mM of ascorbic acid in phosphate buffer solution was also investigated. Again, the bare platinum gave a very strong response for even small concentration of ascorbic acid. The response of the PPy-GOx electrode was similar, but less. This interference from ascorbic acid can be greatly reduced if the PPy-GOx electrode is covered with an outer layer of P-oPDA, as a bilayer arrangement of PPy-GOx/P-oPDA. This was accomplished by covering the inner PPy-GOx film with an electrodeposited P-oPDA film. The electrodeposition of the outer layer involved cycling of the Pt/PPy-GOx electrode potential from 0.0 to 0.8 V for 10-20 times at a scan rate of 20 mV/sec in 0.05 M phosphate buffer solution which contained 0.05M oPDA.

Also two other single layer films were prepared galvanostatically with a charge of 30 $mC/cm^2$ (~70 nm thick): (i) without polypyrrole as P-oPDA-GOx (formed with 0.1 M oPDA and 70 U/mL GOx) and (ii) with polypyrrole as PPy-P-oPDA-GOx (formed with 0.1 M PPy, 0.02 M oPDA and 70 U/mL). The first electrode gave low sensitivity (27 mV/dec) and long response time for potentiometric sensing of glucose. The second sensor, in spite of its comparatively high sensitivity to glucose (84 mV/dec), suffered from similar interference from ascorbic acid as the polypyrrole single layer electrodes. It appears that the structure of the film produced from the mixture of oPDA and Py is mainly determined by PPy, but the deposition of oPDA occurs along with electroconductive PPy.

Performance of PPy-GOx/P-oPDA Bilayer Glucose Sensors

Figure 10:
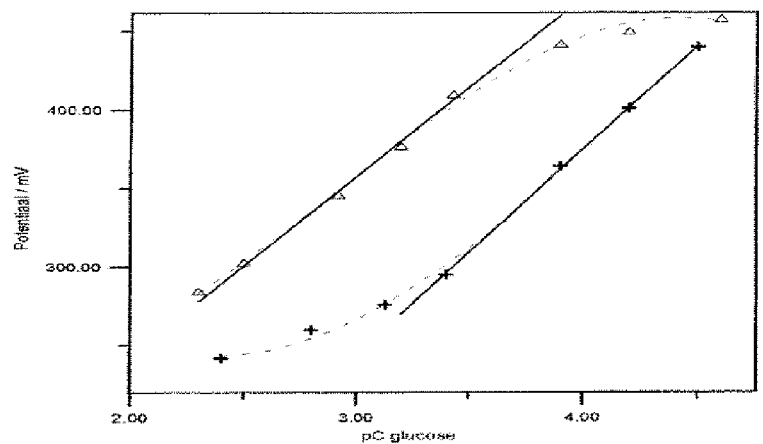
FIG. 10 is a graphical representation of the potentiometric responses of PPy-GOx/P-oPDA electrode to glucose in stirred (Δ) and stagnant (×) solutions.

The bilayer PPy-GOx/P-oPDA electrode gave a very sensitive potentiometric response to glucose (about 100 mV/dec). Furthermore, it experienced relatively low interference from ascorbic acid and was highly stable with time. As recently reported [Adeloju and Moline, Biosens. Bioelectronics, 16. (2001) 133], the potentiometric response of the PPy-GOx/PPy-Cl sensor is significantly influenced by hydrodynamic conditions (electrolyte stirring rate). FIG. 10 shows the potentiometric responses obtained with the bilayer sensor for glucose in stirred and stagnant solutions. In the case of stagnant solutions the electrode was inverted to enable a volume (200 μL) of the solution to be placed on the electrode surface. It can be seen that the responses obtained in the stirred solutions were more sensitive than in the stagnant solutions. If the potential of sensor is determined by the concentration of hydrogen peroxide generated on the electrode surface it is obvious that during stirring the surface concentration of $H_2O_2$ will be less than in stagnant solution. This indicates that the transport processes of glucose from the solution to the surface of sensor are not critical and glucose is always present in excess at the solution/film interface. The hydrogen peroxide produced on the electrode surface can be transported in one of two ways: (a) through the film to the surface of Pt electrode, and/or (b) to the bulk of the solution. Under stirring conditions the main flux of $H_2O_2$ will be transported to the solution and a higher bulk concentration of glucose is necessary to obtain the same surface concentration of $H_2O_2$ as in stagnant solution. Thus, if the main constraints to the diffusion of $H_2O_2$ are within the film it will be necessary to minimise diffusion processes from the film boundary to the solution (best sensitivity) in order to determine small concentrations of glucose. On the other hand, if the bulk concentration of glucose is comparatively high, convective diffusion of hydrogen peroxide from the surface of the film to the solution should be increased to avoid its "saturation" on the Pt surface. Owing to the observed differences between measurements made under stagnant and stirring conditions (FIG. 10) it is recommended that a constant stirring rate be maintained during electrode calibration and sample analysis to avoid error caused by variation of measurement conditions.

Furthermore, the potentiometric responses obtained with a bilayer P-oPDA/PPy-GOx glucose sensor prepared by first depositing a P-oPDA layer followed by the deposition of an outer PPy-GOx layer was much less sensitive than for the reversed PPy-GOx/P-oPDA bilayer arrangement. This may be related to the better retention of the enzyme in the latter than in the former. This may also be partly associated with the nature of the polymer closest to the sensing medium, with the conductive polymer giving better sensitivity than the insulating form of P-oPDA. It is also possible that the subsequent deposition of PPy-GOx film on an already formed P-oPDA may not be an effective approach for trapping and retaining the enzyme. Thus, the best potentiometric response for glucose was obtained with a PPy-GOx/P-oPDA bilayer arrangement. This sensor arrangement provides good response and sensitivity to glucose and minimum interference from ascorbic acid.

Figure 11:
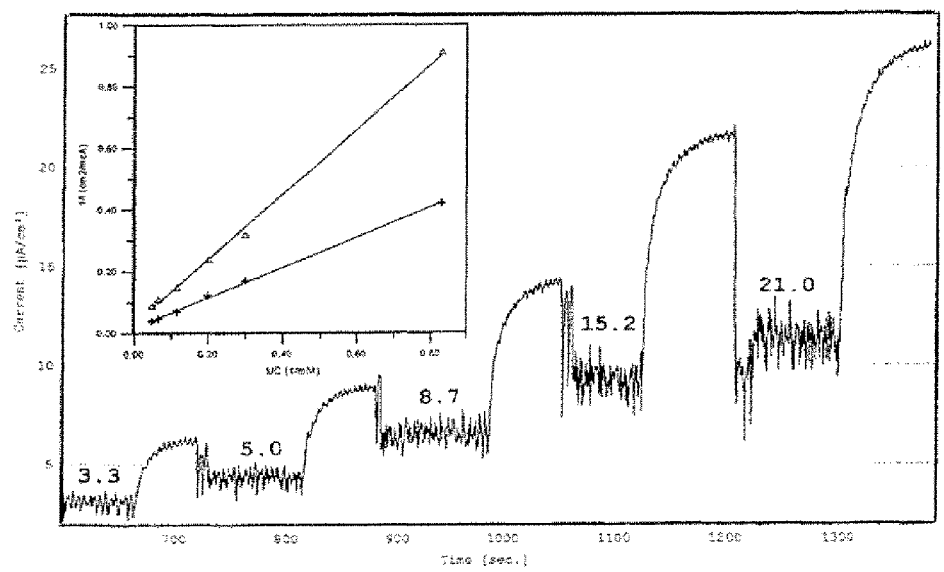
FIG. 11 is a graphical representation of the amperometric responses of PPy-GOx/P-oPDA electrode to glucose in stirred (Δ) and stagnant (×) solutions. Lineweaver-Burke plot shown in inset.

The use of the PPy-GOx/P-oPDA bilayer arrangement for amperometric sensing of glucose was also investigated. FIG. 11 shows the amperometric response obtained for glucose with the sensor. The magnitude of the current response depends on a number of consecutive processes such as: (a) convective diffusion of glucose from the bulk of the solution to the electrode/film surface, (b) transfer of the substrate from the solution to the film, (c) chemical decomposition of the substrate by enzyme (chemical reaction). (d) diffusion of the products of decomposition through the film to the surface of the electrode (as well as to the bulk of the solution), (e) electron transfer on the electrode surface (electrochemical stage) and (f) diffusion of the electrochemical reaction products out of the film. The results in FIG. 11 show that the amperometric response was less during stirring of the electrolyte than in stagnant solution. This further confirms the view that convectional diffusion of glucose to the surface of the film is not a limiting step of the electrode process, otherwise the current should increase in proportion to the stirring rate. There is no doubt that diffusion processes are slower in the polymeric film than in the solution. Thus increase in solution stirring increases transport of hydrogen peroxide from the film to the solution and, hence, its concentration is lower at the electrode surface, resulting in less current (stage d).

Similar processes were observed in the potentiometric measurements with the only exception that there is no consumption of hydrogen peroxide on the surface of the electrode (no current flows through the electrochemical system and stages (e) and (f) were absent).

According to the "Lineweaver-Burke" type equation [Kamin and Wilson, *Anal. Chem.*, 52, (1980) 1198]:

$$1/i = (K_m/i_{max})(1/C) + 1/i_{max}$$

plots of the amperometric results in the form: $1/i$ vs $1/C_{glucose}$ should give a straight line with the slope equal to $(K_m/i_{max})$ and intercept equal to $(1/i_{max})$. The dependence of $1/i$ on $1/C$ is illustrated in FIG. 11 for stirred and stagnant conditions. It can be seen that maximum current which can be achieved is higher for stagnant solution (56 µA/cm$^2$) than for stirred solution (33 µA/cm$^2$) which is consistent with the above discussion of associated transport processes. On the other hand, the Michaelis constant is less for stagnant solutions (27 mM) compared with stirred solutions (34 mM), and these were in both cases much higher than for non immobilised GOx (usually about 7 mM). This may be explained by the fact that the Lineweaver-Burke equation is true for the rate of catalytically controlled enzymatic reaction. In the case of stagnant solution the enzymatic reaction may be, at least partly mass transport controlled (mixed kinetics) and $K_m$ calculated from the slope should be considered as "effective", but not true. Nevertheless, these results are very close to that reported by other workers [Kamin and Wilson, *Anal. Chem.*, 52, (1980) 1198].

Figure 12:
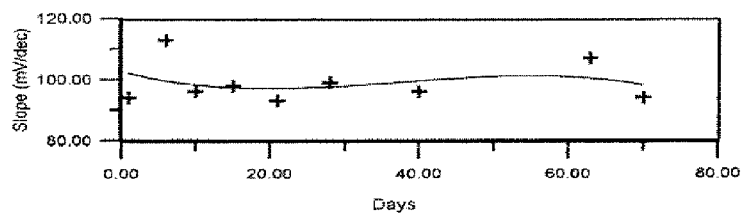
FIG. 12 is a graphical representation of the stability of a PPy-GOx/P-oPDA electrode over 70 days.

A lower glucose concentration can be detected with the PPy-GOx/P-oPDA bilayer arrangement by potentiometric sensing (~0.05 mM) compared with amperometric measurements (~1-2 mM). However, the amperometric sensing enable much wider linear range that is useful for the direct determination of glucose at higher concentrations. Hence, potentiometric and amperometric mode of sensing can be used complementarily to detect glucose within a wide concentration range. Furthermore, the PPy-GOx/P-oPDA electrode was successfully used for potentiometric and amperometric measurements over a two month period. Also the bilayer arrangement gave good response to glucose, experienced little or no interference and, as shown in FIG. 12, high stability over 70 days.

Example 5

Optimisation of Conditions for Amperometric Detection Using PPy-PNP—XOD Nanobiosensor The amperometric detection of phosphate with the PPy-PNP—XOD-Fe(CN)$_6^{4-}$ nanobiosensor was investigated initially by growing a nanolayer of PPy-PNP—XOD-Fe(CN)$_6^{4-}$ film on a platinum disk working electrode with a surface area of 0.022 cm$^{-2}$ as described in Example 1.

The optimisation of polymerisation period, redox mediator concentration and applied potential is shown in Table 3:

TABLE 3

Optimised conditions for amperometric detection of phosphate with PPy-XOD-PNP films

| Optimised parameter | Optimised value |
| --- | --- |
| applied potential | −200 mV |
| polymerisation period | 60 seconds |
| redox mediator concentration | 6 mM K$_4$Fe(CN)$_6$ |
| Barbitone buffer | 0.05 M |
| Inosine | 10 mM |
| NaCl | 0.25 M |

Figure 13:
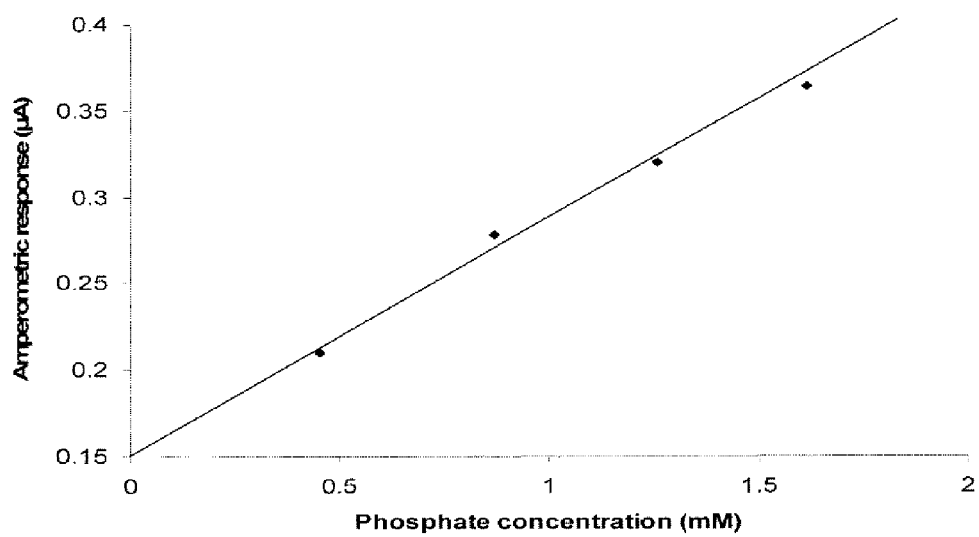
FIG. 13 is a graphical representation of a typical calibration curve obtained for phosphate with the PPy-XOD-PNP—Fe(CN)$_6^{4-}$ biosensor. Measurement solution contained 0.1 M barbitone buffer, 10 mM inosine and 0.25 M NaCl; applied potential was −200 mV. Polymerisation conditions were from a monomer solution/condition: 0.5M pyrrole, 10 mM K$_4$Fe(CN)$_6$, 48 U/ml PNP, 6 U/ml XOD, applied current density: 0.5 mA/cm$^2$, polymerisation period: 60 sec.

With the optimised measurement and polymerisation parameters, more resolved and more sensitive amperometric responses were obtained with the PPy-XOD-PNP—Fe(CN)$_6^{4-}$ biosensor. Increasing addition of phosphate to the measurement solution resulted in a corresponding increase in the phosphate response. FIG. 13 shows typical calibration curve obtained for phosphate measurement with the PPy-XOD-PNP—Fe(CN)$_6^{4-}$ biosensor. The response increased linearly with phosphate concentration between 0 and 2,000 µM.

Example 6

Amperometric Detection of Phosphate in Presence of Gold Nanoparticles (AuNPs)

The first step towards achieving improvement in the sensitivity of the phosphate response is the need to adequately incorporate nanoparticles without interfering with the co-entrapment of the enzymes and mediator. Galvanostatic immobilization was used to ensure that the co-entrapment of all required components can be achieved. The chronopotentiogram obtained during the formation of the PPy-XOD-PNP—Fe(CN)$_6^{4-}$ AuNPs film was very similar to that obtained in absence of AuNPs and thus confirms that the resulting film is conductive. However, only about 30% of surface coverage was achieved in the presence of the AuNPs.

Evidence of the incorporation of gold nanoparticles into the polypyrrole films was obtained with cyclic voltammetric measurements which showed changes in oxidation and reduction peaks with increasing concentration of gold nanoparticles added to the monomer solution. This suggests that the gold nanoparticles were incorporated into the polypyrrole film. Aqueous suspensions of 5 and 20 nm gold nanoparticles used for this study gave similar cyclic voltammetric behaviour.

The cause of the incomplete surface coverage in the presence of the AuNPs was further investigated by varying the number of components in monomer solution. The results in Table 4 show that 100% surface coverage was obtained when only K$_4$Fe(CN)$_6$ or both K$_4$Fe(CN)$_6$ and AuNPs were present. However, the addition of either XOD or PNP reduced the surface coverage to 70%. Further reduction to 30% was observed when both enzymes were added to the monomer solution. These observations suggest that the presence of AuNPs may not be compatible with the incorporation of XOD and PNP. Alternatively, the results may indicate that the presence of K$_4$Fe(CN)$_6$, XOD, PNP and AuNPs contribute synergistically in reducing the surface coverage. It is interesting to note from the data in Table 4 that the trend observed for the changes in surface film coverage were identical for both 5 and 20 nm AuNPs.

TABLE 4

Influence of monomer components on film coverage.

| No. | Components in monomer solution | % coverage of electrode | Film characteristics |
|---|---|---|---|
| | Gold nano-particles (20 nm) | | |
| 1. | Py + $K_4Fe(CN)_6$ | 100 | Violet dark film |
| 2. | Py + $K_4Fe(CN)_6$ + AuNPs | 100 | Violet dark film |
| 3. | Py + $K_4Fe(CN)_6$ + AuNPs + XOD | 70 | Black film |
| 4. | Py + $K_4Fe(CN)_6$ + AuNPs + PNP | 70 | Black film |
| 5. | Py + $K_4Fe(CN)_6$ + AuNPs + XOD + PNP | 30 | Black film |
| | Gold nano-particles (5 nm) | | |
| 1. | Py + $K_4Fe(CN)_6$ | 100 | Violet dark film |
| 2. | Py + $K_4Fe(CN)_6$ + AuNPs | 100 | Violet dark film |
| 3. | Py + $K_4Fe(CN)_6$ + AuNPs + XOD | 70 | Black film |
| 4. | Py + $K_4Fe(CN)_6$ + AuNPs + PNP | 70 | Black film |
| 5. | Py + $K_4Fe(CN)_6$ + AuNPs + XOD + PNP | 30 | Black film |

Polymerisation conditions:
[Py]: 0.5 M,
[$K_4Fe(CN)_6$]: 6 mM,
Au: 0.0005%,
[XOD]: 6 U/mL,
[PNP]: 48 U/mL,
polymerisation period: 120 s,
current density: 0.5 mA/cm$^{-2}$.

The influence of the presence of AuNPs in the PPy-XOD-PNP—Fe(CN)$_6^{4-}$—AuNPs film on the amperometric response obtained for phosphate was investigated by varying its concentration in the monomer solution. The amperometric response obtained for phosphate increased with increasing addition of AuNPs up to 0.0005%. Beyond this concentration, the phosphate response decreased considerably due to the increased AuNPs in the film and the corresponding increase in film thickness which increases the diffusion barrier. However, only a film coverage of 30% was observed with the addition of 0.0005 to 0.001% AuNPs to the monomer solution. Interestingly, 50% film coverage was observed with 0.00025% AuNPs and a 100% coverage was obtained when <0.00025% AuNPs was added, but with much reduced sensitivity for the phosphate response.

Figure 14:
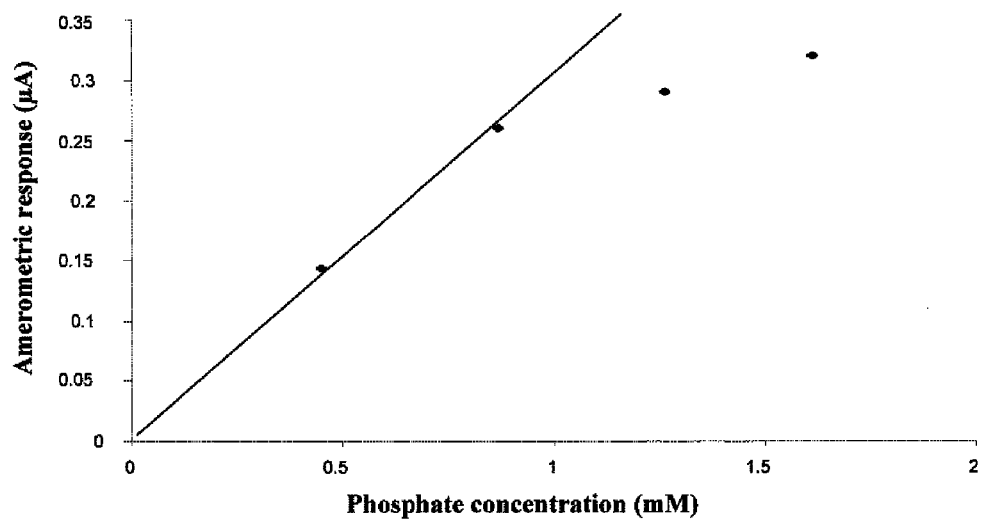
FIG. 14 is a graphical representation of a typical calibration curve of PPy-XOD-PNP—AuNPs biosensor for phosphate measurement. Amperometric measurements were performed in a measurement solution comprising 0.1 M barbitone buffer, 10 mM inosine and 0.25 M NaCl at an applied potential of −200 mV. Polymerisation conditions remained the same as expressed in FIG. 13.

FIG. 14 shows that the phosphate response increased with increasing phosphate concentration with the PPy-XOD-PNP—Fe(CN)$_6^{4-}$—AuNPs biosensor but the linear concentration range was rather limited. Increase in phosphate concentration beyond 1.26 mM gave a noisier response.

Example 7

Amperometric detection with a bilayer PPy-Fe(CN)$_6^{4-}$—AuNPs/PPy-XOD-PNP—Fe(CN)$_6^{4-}$ Electrode The possibility of using a bilayer arrangement was investigated as a means of overcoming the difficulty in achieving full surface coverage with the single layer electrode. From the results in Table 4, it was anticipated that full surface coverage would be achieved with an inner layer of PPy-Fe(CN)$_6^{4-}$—AuNPs. This should enable the formation of an outer layer of PPy-PNP—XOD-Fe(CN)$_6^{4-}$ on top. As expected complete coverage of the Pt electrode was achieved by the sequential formation of both layers. However, the phosphate response was much lower due to the increased film thickness and associated increase in diffusion barrier.

The variation of the enzyme concentrations and the polymerisation period did not improve the sensitivity of the phosphate response obtained with the PPy-Fe(CN)$_6^{4-}$—AuNPs/PPy-XOD-PNP—Fe(CN)$_6^{4-}$ biosensor. Instead the increase in the enzyme concentrations resulted in a significant reduction in the sensitivity of the phosphate response, possibly due to the increase film thickness which affects the diffusion of the products of the enzymatic reaction.

The investigation of the influence of the polymerisation period used for the growth of the inner AuNPs layer revealed that the phosphate response decreased considerably with the use of >60 s for the film formation. This was also due to the increasing film thickness with increasing polymerisation period.

The variation of pyrrole concentration used for the growth of the inner layer indicates that the use of Py concentration >0.4 M results in considerable reduction of phosphate response. This observation is due to the more rapid growth of PPy film, resulting in a rapid increase in film thickness and corresponding increase in diffusion barrier.

The investigation of the effect of the applied potential on the amperometric measurement with the PPy-AuNPs-Fe(CN)$_6^{-4}$/PPy-XOD-PNP bilayer biosensor revealed that two optimum responses were obtained at −200 and +400 mV. These potentials correspond to the oxidation of $H_2O_2$ (+400 mV) and reduction of $O_2$ (−200 mV). Evidently, the presence of the AuNPs shifted the optimum oxidation potential for $H_2O_2$ by 200 mV from +600 mV (in absence of AuNPs) to +400 mV. This observation indicates that the presence of AuNPs made it easier to oxidise $H_2O_2$, suggesting that the nanoparticles act to catalyse the oxidation.

In an attempt to improve the achievable sensitivity and detection limit for phosphate by amperometric measurements, further investigation of the performance of the PPy-Fe(CN)$_6^{4-}$—AuNPs/PPy-XOD-PNP—Fe(CN)$_6^{4-}$ bilayer arrangement was undertaken. The use of chemical and physical adsorption, instead of entrapment in PPy film, was considered for deposition of AuNPs in the inner layer, and the ability to form the outer layer on the deposited AuNPs by entrapment of XOD, PNP and —Fe(CN)$_6^{4-}$ in a PPy layer was investigated.

In order to increase the exposed surface area of the nanoparticles for subsequent entrapment of the enzymes and mediator, AuNPs were physically and chemically deposited on the surface of working electrodes. The physical adsorption involved direct deposition of an aliquot of the liquid suspension of AuNPs on the surface of platinum electrode, followed by drying to remove the liquid and this was repeated in some cases to increase AuNP concentration on the electrode surface. To promote chemical adsorption, 3.0 M NaOH was added to the AuNPs to form gold oxide which adheres onto the electrode surface. Subsequently, a second layer of PPy-XOD-PNP—Fe(CN)$_6^{4-}$ was grown on top of the deposited AuNPs by galvanostatic polymerisation. These approaches did not improve amperometric responses for phosphate over those obtained with the PPy-Fe(CN)$_6^{4-}$—AuNPs/PPy-XOD-PNP—Fe(CN)$_6^{4-}$ bilayer arrangement.

The possible improvement of the sensitivity of the chemically deposited AuNPs to phosphate was investigated by electroplatinising the nanoparticles in a chloroplatinic acid solution, followed by the entrapment of the enzymes and mediator in the outer layer, as PPy-XOD-PNP—Fe(CN)$_6^{4-}$. This strategy led to some reduction in the background noise in the phosphate response and the response appeared to increase with increasing phosphate concentration, but again did not improve beyond those obtained with the PPy-Fe(CN)$_6^{4-}$—AuNPs/PPy-XOD-PNP—Fe(CN)$_6^{4-}$ bilayer arrangement.

Example 8

Optimisation of Surface Coverage of PPy-XOD-PNP—Fe(CN)$_6^{4-}$—AuNPs Monolayer and Sensitivity of Response
i) Formation of PPy-Fe(CN)$_6^{4-}$ Films in the Presence of Varying K$_4$Fe(CN)$_6$ Concentration.

The activation potential for the growth of the film decreased with increasing K$_4$Fe(CN)$_6$ concentration and the activation period increased with mediator concentration. This observation suggested that the use of high K$_4$Fe(CN)$_6$ concentration may be responsible for the poor surface coverage, as the initial rate of film growth is considerably slower than in the presence of lower mediator concentration. It was therefore investigated whether increased surface coverage may be achieved by decreasing K$_4$Fe(CN)$_6$ concentration used for the formation of the PPy-XOD-PNP—Fe(CN)$_6^{4-}$—AuNPs single layer biosensor. The more rapid activation period achieved in the presence of lower redox mediator concentration provides more time for entrapment of the enzymes, redox mediator and AuNPs during galvanostatic polymerisation of pyrrole.

The results in Table 5 shows that film coverage increased with decreasing K$_4$Fe(CN)$_6$ concentration used for the formation of PPy-XOD-PNP—Fe(CN)$_6^{4-}$—AuNPs on the platinum electrode. Full coverage (100%) was achieved when the redox mediator concentration was decreased by 50-fold.

TABLE 5

Influence of K$_4$Fe(CN)$_6$ concentration used for formation of PPy-XOD-PNP-Fe(CN)$_6^{4-}$—AuNPs film on electrode surface coverage.

| No | [K$_4$Fe(CN)$_6$] (mM) | Electrode surface coverage (%) |
|---|---|---|
| 1 | 5.0 | 20 |
| 2 | 4.0 | 30 |
| 3 | 2.0 | 50 |
| 4 | 1.0 | 80 |
| 5 | 0.5 | 90 |
| 6 | 0.1 | 100 |

The phosphate amperometric response decreased with decreasing K$_4$Fe(CN)$_6$ concentration. However, the magnitude of the decrease in phosphate response with a 60-fold dilution of the redox mediator concentration from 6 mM to 0.1 mM K$_4$Fe(CN)$_6$ was only about 30%. which is a reasonable compromise for achieving full surface coverage. For this reason, a mediator concentration of 0.1 mM was used for all other investigations.

ii) Effect of AuNPs Concentration on Biosensor Response and Surface Coverage

The sensitivity of phosphate response obtained with the PPy-XOD-PNP—Fe(CN)$_6^{4-}$—AuNPs biosensor increased with increasing AuNP concentration added to the monomer solution. Optimum amperometric phosphate response was obtained in the presence of 0.0005% AuNPs. Beyond this AuNP concentration, the phosphate response decreased, possibly due to increased film thickness and associated problem with the diffusion barrier. Although the same AuNP concentration was found to be optimum in previous investigation, the sensitivity of the phosphate response obtained in this case is much higher due to the use of the lower redox mediator concentration. It is worth noting that full surface coverage was obtained in the presence of 0.1 mM K$_4$Fe(CN)$_6$ at the various AuNP concentrations. An AuNP concentration of 0.0005% was therefore used in all further investigations.

iii) Effect of Monomer Concentration on Biosensor Response

The phosphate amperometric response obtained with the PPy-XOD-PNP—Fe(CN)$_6^{4-}$—AuNPs biosensor decreased considerably with increasing pyrrole concentration used for the film formation. The film thickness increased more rapidly in the presence of AuNPs with increasing Py concencentration and increased the diffusion barrier, resulting in the rapid lowering of the phosphate response. A very thin PPy-XOD-PNP—Fe(CN)$_6^{4-}$—AuNPs layer was formed with 0.1 M pyrrole and this gave optimum amperometric response for phosphate.

Example 9

Comparison of Nanobiosensors in the Presence or Absence of AuNPs

Figure 15:
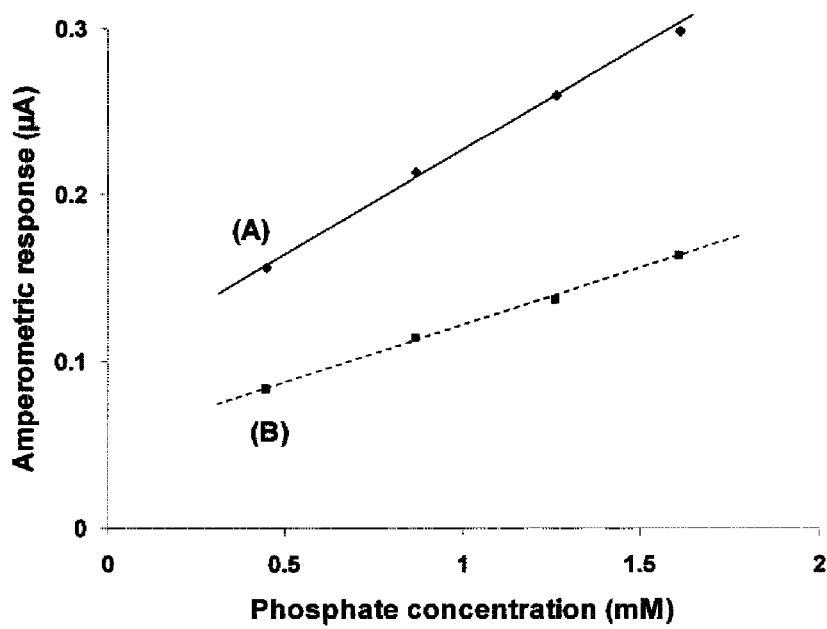
FIG. 15 is a graphical representation of calibration curves obtained with (A) PPy-XOD-PNP—Fe(CN)$_6^{4-}$—AuNPs and (B) PPy-XOD-PNP—Fe(CN)$_6^{4-}$ single layer biosensors. Other conditions include (a) 0.45, (b) 0.87. (c) 1.26 and (d) 1.61 mM phosphate. Applied potential −200 mV, measurement solution contained 0.05 M barbitone buffer, 10 mM inosine and 0.1 M NaCl. Monomer composition/conditions: 0.1 M Py, 0.0005% AuNPs (for A only), 48 U/ml PNP, 6 U/ml XOD, 0.1 mM K$_4$Fe(CN)$_6$, current density 0.5 mA/cm$^2$ and polymerisation period 120 seconds.

A comparison of the phosphate amperometric responses obtained with the films formed in the presence (PPy-XOD-PNP—Fe(CN)$_6^{4-}$—AuNPs) and absence of AuNPs (PPy-XOD-PNP-Fe(CN)$_6^{4-}$) was performed. In both cases the phosphate response increased with increasing phosphate concentration, but the film which contained AuNPs gave considerably higher sensitivity than in its absence. Also a considerable reduction in noise was observed for responses obtained with the PPy-XOD-PNP—Fe(CN)$_6^{4-}$—AuNPs biosensor. The differences in sensitivity is more clearly highlighted in FIG. 15, where the sensitivity obtained for phosphate with the PPy-XOD-PNP—Fe(CN)$_6^{4-}$—AuNPs biosensor was about twice as high as that obtained with the PPy-XOD-PNP—Fe(CN)$_6^{4-}$ biosensor.

Example 10

Further improvements in sensitivity of the PPy-XOD-PNP—Fe(CN)$_6^{4-}$—AuNP biosensor were investigated by varying polymerisation conditions such as XOD and PNP concentrations, polymerisation period and applied current density and measurement conditions such as NaCl, barbitone buffer and ionosine concentrations and applied potential.

i) Optimisation of Additional Polymerisation Conditions

The amperometric response obtained for phosphate with the PPy-XOD-PNP—Fe(CN)$_6^{4-}$—AuNPs biosensor increased with increasing XOD concentration in the monomer solution up to 6 UmL$^{-1}$. Further increase in the enzyme concentration resulted in gradual reduction in the sensitivity of the phosphate response due to the increased thickness of the PPy-XOD-PNP—Fe(CN)$_6^{4-}$—AuNPs film. A XOD concentration of 6 UmL$^{-1}$ was therefore used in all monomer solutions for preparation of the PPy-XOD-PNP—Fe(CN)$_6^{4-}$—AuNPs biosensor.

The ratio of XOD:PNP used in the monomer solution also has a significant effect on the response obtained for phosphate with the PPy-XOD-PNP—Fe(CN)$_6^{4-}$—AuNPs biosensor. The optimum phosphate response was obtained when an enzyme ratio of 1:8 (6 units of XOD and 48 units of PNP) was used. It is worth noting that the phosphate responses obtained at the optimum enzyme ratio were also more reproducible. The decrease in amperometric response observed with lower PNP concentration may be due to the presence of insufficient PNP, while those observed at the higher PNP concentrations may be due to insufficient XOD and/or increased film thickness. A XOD:PNP ratio of 1:8 was therefore used for all further investigation.

The phosphate response increased with an increase in the polymerisation period used for the growth of PPy-XOD-PNP—Fe(CN)$_6^{4-}$—AuNPs films up to 120 seconds. Further increase in polymerisation period increased the film thickness, resulting in an increased diffusion barrier and, hence, a reduction in phosphate response. A polymerisation of 120 seconds was therefore chosen for all further investigations.

The phosphate response obtained with the PPy-XOD-PNP—Fe(CN)$_6^{4-}$—AuNPs biosensor was also influenced by the choice of applied current density, with optimum response obtained with the use of 0.5 mA cm$^{-2}$. The lower responses obtained below this current density was due to the lower enzyme concentrations in the resulting films, while those obtained above this current density was due to the increased film thickness and higher diffusion barrier. Interestingly, an unexpected increase in phosphate response was observed with the use of an applied current density of 0.8 mA cm$^{-2}$. This may be due to a change in the porosity and/or conductivity of the film. An applied current density of 0.5 mA cm$^{-2}$ was used for other film growths.

ii) Optimisation of Measurement Parameters

The amperometric response obtained for phosphate with the PPy-XOD-PNP—Fe(CN)$_6^{4-}$—AuNPs biosensor decreased with increasing addition of NaCl concentration to the measurement solution from 0.05 to 0.75 M. This may be due to the increasing tendency for Cl$^-$ ions to exchange with the immobilized enzymes in the film as its concentration becomes higher. The phosphate response became less reproducible when the NaCl concentration exceeded 0.05 M. For this reason, 0.05 M NaCl was added to the measurement solution.

Similarly, the barbitone buffer concentration used in the measurement solution had significant influence on the phosphate response obtained with the PPy-XOD-PNP—Fe(CN)$_6^{4-}$—AuNPs biosensor. The optimum phosphate response was obtained in 0.05 M barbitone buffer solution which contained 0.05 M NaCl. Barbitone buffer concentration lower than 0.05 M may not be sufficient to maintain the required pH for the enzyme catalysed reactions, while higher buffer concentrations hinders the catalysis due to the presence of excessive ions. For this reason, 0.05 M barbitone buffer was used in the measurement solution.

In the reactions involved in the detection of phosphate with XOD and PNP, inosine plays a role and its absence can have a significant effect on the resulting phosphate response. The sensitivity of the phosphate response obtained with the PPy-XOD-PNP—Fe(CN)$_6^{4-}$—AuNPs biosensor increased with increasing inosine concentration up to 10 mM. Lower concentrations do not provide adequate stoichiometric amount for the production of xanthine and uric acid. This, in turn, lowers the production of $H_2O_2$ and results in lower phosphate response. Concentrations higher than 10 mM may result in excess amounts that may interfere with the electrode processes. An inosine concentration of 10 mM was therefore employed in all other investigations.

Figure 16:
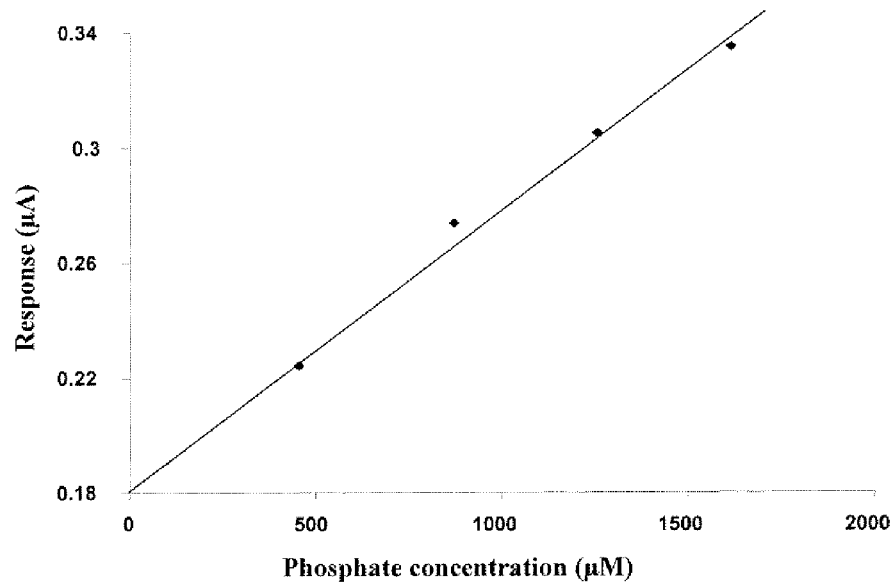
FIG. 16 is a graphical representation of a typical calibration curve obtained for phosphate with the single layer PPy-XOD-PNP—Fe(CN)$_6^{4-}$—AuNPs biosensor at high concentrations. Other conditions include (a) 455, (b) 871, (c) 1256 and (d) 1613 M phosphate; E$_{app}$-200 mV; measurement solution contained 0.05 M NaCl; 0.05 M barbitone buffer and 10 mM of inosine.

Under the optimised polymerisation and measurement conditions, it was found that the optimum phosphate response was again obtained with the PPy-XOD-PNP—Fe(CN)$_6^{4-}$—AuNPs biosensor at −200 mV. Notably, the amperometric responses obtained for phosphate with the optimised PPy-XOD-PNP—Fe(CN)$_6^{4-}$—AuNPs biosensor had much lower background noise at this applied potential. However, an increase in the background noise was observed when applied potentials lower than −200 mV was used, while the phosphate response obtained at higher applied potentials was not stable. An applied potential of −200 mV was therefore employed for all phosphate measurement with the PPy-XOD-PNP—Fe(CN)$_6^{4-}$—AuNPs biosensor.

iii) Analytical Performance of the Single Layer PPy-XOD-PNP—Fe(CN)$_6^{4-}$—AuNPs Biosensor The ability to detect high (higher micromolar to millimolar range) and low (sub-micromolar to lower micromolar range) concentrations of phosphate with the optimised single layer PPy-XOD-PNP—Fe(CN)$_6^{4-}$—AuNPs biosensor was investigated to determine the extent of the analytical performance of the biosensor. The amperometric response was obtained with the biosensor increased with increasing phosphate concentration between 400 μM and 1.6 mM. Furthermore, the phosphate responses obtained within this concentration range were much smoother due to the higher current range. FIG. 16 demonstrates that the responses obtained with the optimised PPy-XOD-PNP—Fe(CN)$_6^{4-}$—AuNPs single layer biosensor increased with increasing phosphate concentration within the measured range.

Figure 17:
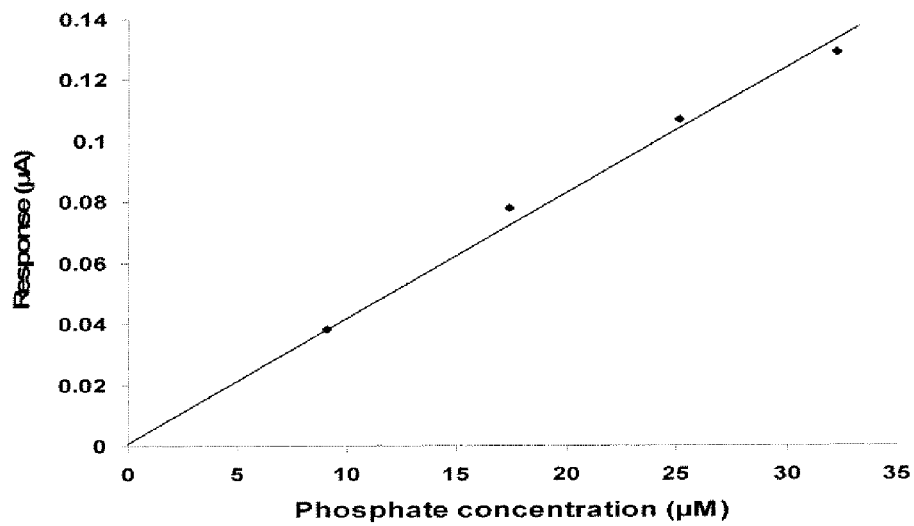
FIG. 17 is a graphical representation of a typical calibration curve obtained for phosphate with the single layer PPy-XOD-PNP—Fe(CN)$_6^{4-}$—AuNPs biosensor at low concentrations. Other conditions include (a) 9.1, (b) 17.4, (c) 25.1 and (d) 32.3 μM phosphate; E$_{app}$-200 mV; measurement solution contained 0.05 M NaCl; 0.05 M barbitone buffer and 10 mM of inosine.

Similarly the amperometric response obtained between 9 and 32 μM with the biosensor increased with increasing phosphate concentration. The higher background noise was due to the much lower current range measured. FIG. 17 demonstrates that the responses obtained at these lower concentrations with the optimised PPy-XOD-PNP—Fe(CN)$_6^{4-}$—AuNPs single layer biosensor increased with increasing phosphate concentration between 0 and 32 As little as 0.9 μM of phosphate can be detected amperometrically with the single layer PPy-XOD-PNP—Fe(CN)$_6^{4-}$—AuNPs biosensor.

Example 11

Formation and Utilization of PPy-XOD-PNP—Fe(CN)$_6^{4-}$—AuNPs/P-oPDA Bilayer Biosensor An outer poly-ortho-phenylene diamine (P-oPDA) layer was polymerised by cyclic voltammetry on top of an inner PPy-XOD-PNP—Fe(CN)$_6^{4-}$—AuNPs layer as prepared in Example 10. Various oPDA concentrations (25-100 mM) in 25-100 mM barbitone buffer (pH 7.8) which contained 0.1-1.0 M KCl were used, after purging with nitrogen for 10 minutes, for electropolymerisation of oPDA at various scanning rates and with a number of scans in a stagnant solution. The magnitude of the current in the cyclic voltammogram decreased with increasing scan due to the increasing thickness of P-oPDA layer, while film thickness decreased with increasing scan rate.

The influence of significant parameters, such as number of scans, scan rate, and concentrations of barbitone buffer, KCl and oPDA on the growth of P-oPDA outer layer and their effects on the resulting amperometric response obtained for phosphate with the bilayer biosensor were investigated and the optimum conditions were identified as discussed below.

The amperometric response obtained for phosphate with the PPy-XOD-PNP—Fe(CN)$_6^{4-}$—AuNPs/P-oPDA biosensor increased with increasing number of scans up to 5 scans and then decreased rapidly with further increase in number of scans. This is due to the increasing film thickness of P-oPDA outer layer with increasing number of scans during the potentiodynamic growth. The increased insulation of the outer layer after the 5$^{th}$ scan may be responsible for the observed decrease of the phosphate response. The use of 5 scans was therefore chosen for the growth of the P-oPDA outer layer for other investigations.

The phosphate response obtained with the bilayer biosensor also increased with the increasing scan rate used for the growth of P-oPDA outer layer. As the thickness of the P-oPDA layer increased with decreasing scan rate, it was evident that the increased film thickness was responsible for the relatively low sensitivity obtained for phosphate with the outer layer formed at low scan rates. The thicker outer P-oPDA layer increases the diffusion barrier and reduced the resulting amperometric signal.

The amperometric response obtained for phosphate with the PPy-XOD-PNP—Fe(CN)$_6^{4-}$—AuNPs/P-oPDA biosensor increased with increasing buffer concentration up to 75 mM. Beyond this concentration, the response decreased possibly due to increased buffering capacity and associated increase in film thickness due to the presence of increased counter anionic species. A buffer concentration of 75 mM was therefore employed for all other investigations.

The addition of KCl, up to 0.5M, into the polymerisation solution for the growth of P-oPDA outer layer resulted in an increasing phosphate response obtained with the PPy-XOD-PNP—Fe(CN)$_6^{4-}$—AuNPs/P-oPDA biosensor. Beyond this concentration, the phosphate response decreased possibly due to the increased tendency to form thicker films. A KCl concentration of 0.5 M was therefore used for other investigations.

The phosphate response obtained with the PPy-XOD-PNP—Fe(CN)$_6^{4-}$—AuNPs/P-oPDA biosensor also increased with increasing oPDA concentration used for the film growth up to 50 mM. Beyond this oPDA concentration, the phosphate response decreased, possibly due to increased film thickness.

Figure 18:
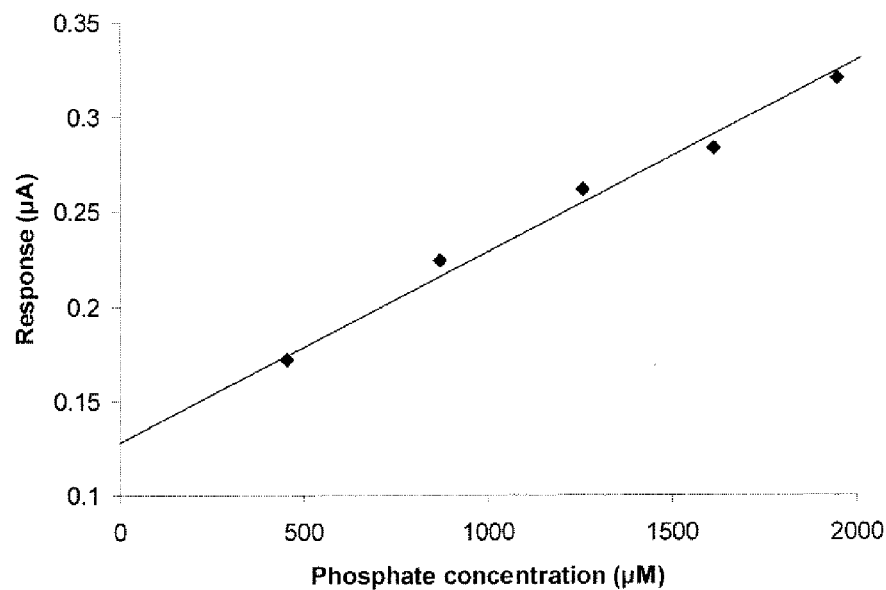
FIG. 18 is a graphical representation of a typical calibration curve obtained for phosphate with PPy-XOD-PNP—Fe(CN)$_6^{4-}$—AuNPs/P-oPDA bilayer biosensor. Applied potential −200 mV; measurement solution contained 0.05 M each of NaCl and barbitone buffer, and 10 mM of inosine.

The response of the optimised PPy-XOD-PNP—Fe(CN)$_6^{4-}$—AuNPs/P-oPDA biosensor to a range of phosphate concentrations was investigated to determine linear concentration range and minimum detectable concentration. An increase in phosphate response was obtained with the PPy-XOD-PNP—Fe(CN)$_6^{4-}$—AuNPs/P-oPDA biosensor with increasing addition of phosphate. A linear concentration range was also observed between 450-1950 µM, as illustrated in FIG. 18.

Figure 19:
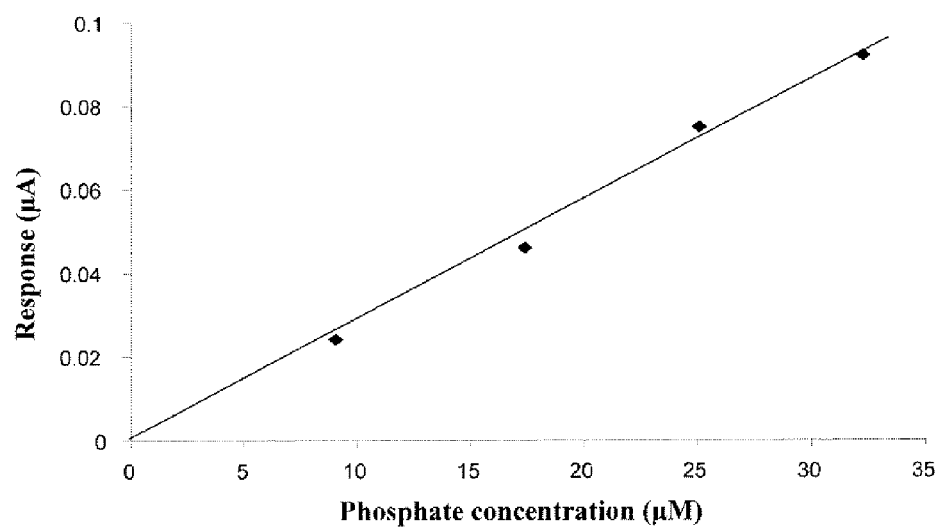
FIG. 19 is a graphical representation of a typical calibration curve obtained for low phosphate concentrations with PPy-XOD-PNP—Fe(CN)$_6^{4-}$—AuNPs/P-oPDA bilayer biosensor. Applied potential −200 mV; measurement solution contained 0.05 M each of NaCl and barbitone buffer, and 10 mM of inosine.

The PPy-XOD-PNP—Fe(CN)$_6^{4-}$—AuNPs/P-oPDA biosensor also gave sensitive responses to low phosphate concentrations. The minimum detectable phosphate concentration measured with the PPy-XOD-PNP—Fe(CN)$_6^{4-}$—AuNPs/P-oPDA biosensor was 0.91 µM. A linear calibration plot was also obtained at the low concentrations between 0 and 35 µM, as shown in FIG. 19.

Figure 20:
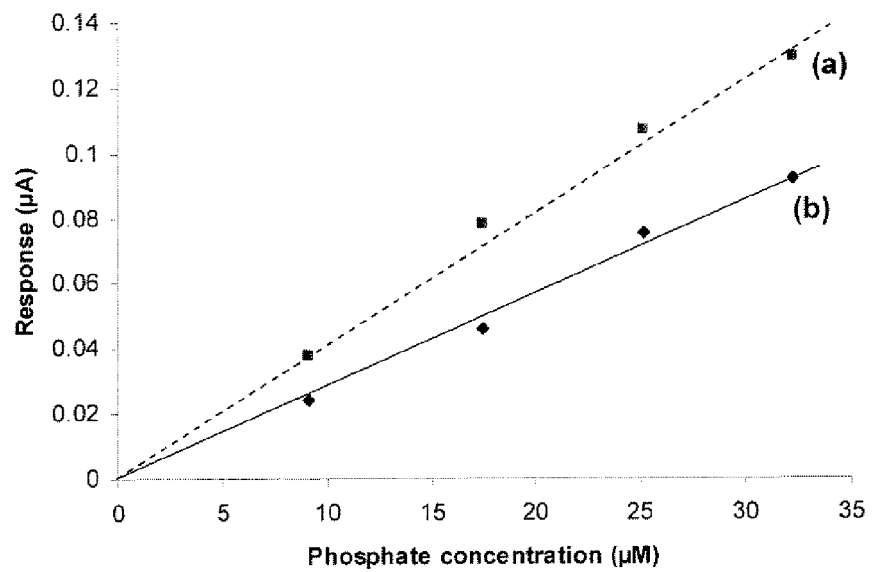
FIG. 20 is a graphical representation of a typical calibration curve obtained for phosphate with (A) PPy-XOD-PNP—Fe(CN)$_6^{4-}$—AuNPs single layer and (B) PPy-XOD-PNP—Fe(CN)$_6^{4-}$—AuNPs/P-oPDA bilayer biosensors. Applied potential −200 mV; measurement solution contained 0.05 M each of NaCl and barbitone buffer, and 10 mM of inosine.

A comparison of the amperometric responses obtained for phosphate with a single layer PPy-XOD-PNP—Fe(CN)$_6^{4-}$—AuNPs biosensor and a bilayer PPy-XOD-PNP—Fe(CN)$_6^{4-}$—AuNPs/P-oPDA biosensor was performed. The overall current magnitude was identical for both type of biosensor, but the bilayer biosensor exhibited reduced noise in the response signal. Linear calibration plots were obtained with the single layer and bilayer biosensors for phosphate between 0 and 35 µM, as shown in FIG. 20.

Example 12

Sulfite Biosensor
Electrode Process

Most of the reported electrochemical detection methods use the enzyme, sulfite oxidase (SOx), to catalyse the oxidation of sulfite to sulfate, and employ the resulting current or potential response for amperometric and potentiometric measurement of sulfite. Sulfite oxidase is a homodimer which contains two identical subunits with two domains, an N-terminal domain and a C-terminal domain, connected by ten amino acids to fowl a loop.

Within the N-terminal domain there is a heme cofactor which has 3 adjacent antiparallel beta sheets and 5 alpha helices, while within the C-terminal domain there is a molybdopterin co-factor surrounded by 13 beta sheets and 3 alpha helices. An important feature of the molybdopterin cofactor is that it has a Mo(VI) centre bonded to a sulfur from cysteine, an ene-dithiolate from pyranopterin, and two terminal oxygen atoms. The catalytic oxidation of sulfite to sulfate occurs at this molybdenum centre.

In aqueous solutions, the redox reaction between sulfite and oxygen proceed quantitatively according to the following equation:

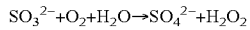

$$SO_3^{2-}+O_2+H_2O \rightarrow SO_4^{2-}+H_2O_2$$

As such measurement of sulfite can be achieved by monitoring either: (a) the oxygen consumption caused by the catalytic activity of sulfite oxidase; or (b) the liberation of hydrogen peroxide as a product of the catalytic reaction; or (c) by using an electron mediator to enhance the response.

Preparation of PPy-SOx Biosensor

The working electrode was a platinum electrode with a surface area of 0.02 cm$^2$. Prior to polypyrrole deposition, the electrode was polished using alumina and rinsed with Milli Q water. Sulfite oxidase was entrapped in the PPy film by electrochemical deposition of polypyrrole in the presence of sulfite oxidase. The solution in which the galvanostatic polymerisation was carried out contained pyrrole and sulfite oxidase in 0.05 M phosphate buffer (pH 7.4) and polymerisation was carried out by applying a current density of 0.2 mA cm$^{-2}$ for a period of 120 s. This electrode is denoted as PPy-SOx herein.

Preparation of PPy-SOx/P-oPDA Bilayer Electrode

PPy-SOx was prepared as described above and formation of the P-oPDA layer was obtained by cycling the potential of the PPy-SOx electrode in a solution of 50 mM oPDA between 0 and 0.8 V by cyclic voltammetry.

Electrochemical Measurement

The electrochemical cell (5 mL) consisted of a platinum counter electrode, a Ag/AgCl as the reference and a platinum working electrode. The working electrode was a platinum disk with a diameter of 1.6 mm (SA 0.02 cm$^2$). Prior to the formation of PPy films, the platinum working electrode was polished with 0.3 µm alumina for 3 min and ultrasonicated in Milli-Q purified water for 1 min to remove alumina. All electrochemical measurements were carried out in presence of oxygen. Amperometric measurements were made in a three-electrode cell consisting of a platinum working electrode coated with PPy film, Ag/AgCl (as a reference electrode) and a platinum wire as an auxiliary electrode.

Sulfite Measurement

The chronopotentiogram obtained during the formation of PPy-SOx film shows a potential trend after the commencement of polymerisation indicating that a conducting polymer was formed on the electrode.

The results obtained with successive addition of sulfite standard into a tris buffer solution. The increase in the anodic current after addition of sulfite is attributed to the oxidation of hydrogen peroxide produced by the enzyme-catalysed oxidation of sulfite at the electrode. This was confirmed with the addition of hydrogen peroxide to the solution and similar current response was observed with the applied potential. The fact that the sulfite response was obtained without optimisation confirmed that the immobilized SOx was active within the PPy film. Furthermore, the sulfite response obtained with an unoptimised PPy-SOx/P-oPDA bilayer biosensor increased with increasing sulfite concentration. However, the optimisation of the individual layer is required to obtain optimum responses for sulfite.

Sulfite Detection with PPy-SOx-Fe(CN)$_6^{4-}$ and PPy-SOx-Fe(CN))$_6^{4-}$—AuNPs Biosensors The possible extension of the conditions established for the fabrication of the PPy-PNP-XOD-AuNPs-Fe(CN)$_6^{4-}$ biosensor, to the amperometric detection of sulfite was investigated to give a preliminary indication of its adequacy for other enzyme systems. The co-immobilization of AuNPs. Fe(CN)$_6^{4-}$ and SOx into a PPy film was achieved simply by replacing XOD and PNP with SOx. The adequacy of the resulting PPy-SOx-AuNPs-Fe(CN)$_6^{4-}$ biosensor was then evaluated for amperometric detection of sulfite.

Formation of PPy-SOx-Fe(CN)$_6^{4-}$ and PPy-SOx-Fe(CN)$_6^{4-}$ AuNPs Biosensors The chronopotentiograms obtained during the formation of PPy-SOx-Fe(CN)$_6^{4-}$ and PPy-SOx-Fe(CN)$_6^{4-}$—AuNPs films on a platinum electrode by galvanostatic polymerisation shows that a more conducting film was formed in the presence of AuNPs under the same conditions established. However, further optimisation of the polymerisation conditions was still required to achieve optimum chronopotentiogram and adequate characteristics of the PPy-SOx-Fe(CN)$_6^{4-}$ and PPy-SOx-Fe(CN)$_6^{4-}$—AuNPs films for sulfite detection.

Nevertheless, as a preliminary investigation, these initial chronopotentiograms are sufficient to indicate that the AuNPs can also be adequately incorporated into PPy films concurrently with SOx and Fe(CN)$_6^{4-}$ for sulfite detection. It is also important to note that full surface coverage was obtained for both the PPy-SOx-Fe(CN)$_6^{4-}$ and PPy-SOx-Fe(CN)$_6^{4-}$—AuNPs films.

Figure 21:
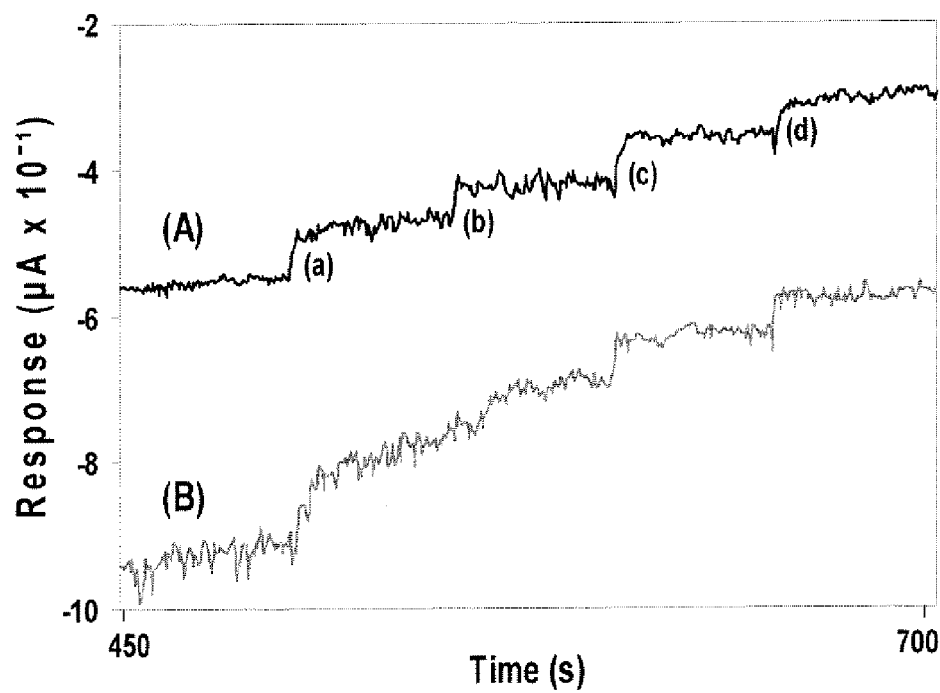
FIG. 21 provides amperometric responses obtained for sulfite with (A) PPy-SOx-Fe(CN)$_6^{4-}$ and (B) PPy PPy-SOx-Fe(CN)$_6^{4-}$—AuNPs biosensors. (a) 1.0, (b) 1.91, (c) 2.74 and (d) 3.51 μM sulfite. Applied potential −700 mV, measurement solution contained 0.05 M phosphate buffer and 0.1 M KCl. Monomer composition/conditions: 0.1M pyrrole, 5 U/ml SOx, 0.1 mM K$_4$Fe(CN)$_6$, 0.0005% AuNPs (for B only), current density 0.5 mA/cm$^2$ and polymerisation period 120 seconds, except that 0.0005% AuNPs was used in (B).

Sulfite Detection with PPy-SOx-Fe(CN)$_6^{4-}$ and PPy-SOx-Fe(CN)$_6^{4-}$—AuNPs Biosensors A comparison of the sulfite amperometric responses obtained with PPy-SOx-Fe(CN)$_6^{4-}$ (A) and PPy-SOx-Fe(CN)$_6^{4-}$—AuNPs (B) biosensors is presented in FIG. 21. In both cases, the sulfite response increased with increasing sulfite concentration. The PPy-SOx-Fe(CN)$_6^{4-}$—AuNPs biosensor gave higher amperometric responses for sulfite than with the PPy-SOx-Fe(CN)$_6^{4-}$ biosensor. However, as expected under the unoptimised conditions, an increase in the background noise of the response was observed with the incorporation of AuNPs into the PPy-SOx-Fe(CN)$_6^{4-}$ film. As these are only preliminary results, it is anticipated that the sulfite are response obtained with both the PPy-SOx-Fe(CN)$_6^{4-}$ (A) and PPy-SOx-Fe(CN)$_6^{4-}$—AuNPs (B) biosensors will improve considerably after optimisation of the polymerisation and measurement conditions.

Example 13

Nitrate Detection with PPy-NaR—NADH—Fe(CN)$_6^{4-}$ and PPy-NaR—NADH Biosensors

The co-immobilization of nitrate reductase (NaR) and NADH into PPy films in the presence and absence of Fe(CN)$_6^{4-}$ during the galvanostatic polymerisation of Py was investigated. The adequacy of the resulting PPy-NaR—NADH—Fe(CN)$_6^{4-}$ and PPy-NaR—NADH biosensors for amperometric detection of nitrate was then evaluated.

Amperometric Detection of Nitrate with PPy-NaR—NADH—Fe(CN)$_6^{4-}$ Biosensor

The chronopotentiogram obtained during the galvanostatic polymerisation of Py in presence of NaR, NADH and Fe(CN)$_6^{4-}$ indicates that a conducting PPy-NaR—NADH—Fe(CN)$_6^{4-}$ film was formed on the platinum electrode. A decrease in the polymerisation potential was observed within the first 25 seconds, indicating the formation of the conducting polymer film. The lowering of the electrode potential from 617 mV to 549 mV clearly indicates that the conductivity of the film increased with increasing film thickness.

The possibility of detection of nitrate with the PPy-NaR—NADH—Fe(CN)$_6^{4-}$ biosensor was investigated by varying the applied potential for amperometric measurement from −800 mV to +500 mV. No response was observed at all applied potentials, except at -600 mV where a somewhat noisy response which increased with increasing nitrate concentration was observed. The nitrate response was not reproducible. Also, no potentiometric response was obtained for nitrate with the PPy-NaR—NADH—Fe(CN)$_6^{4-}$ biosensor. Further investigation was conducted in the absence of the mediator to establish its effect on the amperometric response of nitrate.

Amperometric Detection of Nitrate with PPy-NaR—NADH Biosensor

The chronopotentiogram obtained during the galvanostatic polymerisation of Py in presence of NaR and NADH showed commencement of the formation of a conductive Py-NaR—NaDH layer on a platinum electrode occurred from the decrease in the polymerisation potential which occurred within the first 10 s. The increase in conductivity of the film and film thickness as well as the amount of NaR and NADH in the film, was also indicated by the lowering of the electrode potential from 678 mV to 605 mV.

The amperometric detection of nitrate with the PPy-NaR—NADH biosensor was investigated by varying the applied potential from −800 mV to +500 mV. The nitrate amperometric response was only observed at an applied potential between −375 mV and −25 mV. The optimum and most reproducible nitrate response was obtained with the PPy-NaR—NADH biosensor at an applied potential of −200 mV. This potential was therefore chosen for all other investigations, but further optimisation of the film formation and measurement conditions was necessary to improve the sensitivity of nitrate response obtained with the biosensor.

The increasing concentration of pyrrole used for the formation of the PPy-NaR—NADH film resulted in increasing nitrate amperometric response up to 0.4 M. The amperometric response decreased with further increase in Py concentration due to the increasing film thickness which increased the diffusion barrier, and, hence, reduced the ability of catalytic product to reach the electrode surface. A Py concentration of 0.4 M was therefore chosen for other investigations.

The amperometric response obtained for nitrate with the PPy-NaR—NADH electrode increased with increasing polymerisation period up to 120 s and gradually decreased with further increase in polymerisation period. The observed reduction of the nitrate response with the increasing polymerisation period was again due to the increased film thickness and associated limitation of the increased diffusion barrier. However, on the basis of reproducibility, the nitrate response obtained with PPy-NaR—NADH film formed for 180 s was found to be more superior than that obtained with a polymerisation period of 120 s. Hence, all further investigations were carried out with a PPy-NaR—NADH film formed with a polymerisation period of 180 s.

An increase in the applied current density used for the growth of the PPy-NaR—NADH film resulted in an increase in the nitrate response up to a current density of 0.7 mA/cm$^2$. The response decreased with further increase in the applied current density due to the more rapid polymerisation which increases the film thickness and may decrease the amount of enzyme incorporated in the film. An applied current density of 0.7 mA/cm$^2$ was therefore chosen for growing the PPy-NaR—NADH film for all further investigations.

The enzyme (NaR) concentration used for the formation of PPy-NaR—NADH film had a significant influence on the resulting amperometric response for nitrate. The nitrate response increased with increasing NaR concentration up to 1000 mU/mL. Further increase in NaR concentration resulted in slight decrease in amperometric response, possibly due to increased film thickness and associated effect of the increased diffusion barrier. A NaR concentration of 1000 mU/mL was therefore used for other investigations.

The growth of conducting PPy-NaR—NADH films was promoted with the addition of potassium chloride into the monomer as an electrolyte. An optimum amperometric response for nitrate was obtained when 0.2 M KCl was used for the film formation. Beyond this concentration, it appears that increased formation of PPy-Cl is promoted and the resulting increased film thickness contributes to the diffusion barrier and reduced the sensitivity of the nitrate response.

The two measurement conditions that can influence the sensitivity of the nitrate response are pH and buffer concentration. The amperometric response obtained for nitrate with the PPy-NaR—NADH biosensor varied with the pH of the phosphate buffer solutions used for the measurement. The optimum nitrate response was obtained at pH 7.30. A phosphate buffer solution of pH 7.3 was therefore used for all further work.

Similarly, the concentration of phosphate buffer solutions influenced the sensitivity of the nitrate response. The nitrate response increased with increasing buffer concentration up to 0.05 M. Further increase in the buffer concentration resulted in a decrease in the nitrate response. For this reason, all measurements were made in 0.05 M phosphate buffer solution.

Figure 22:
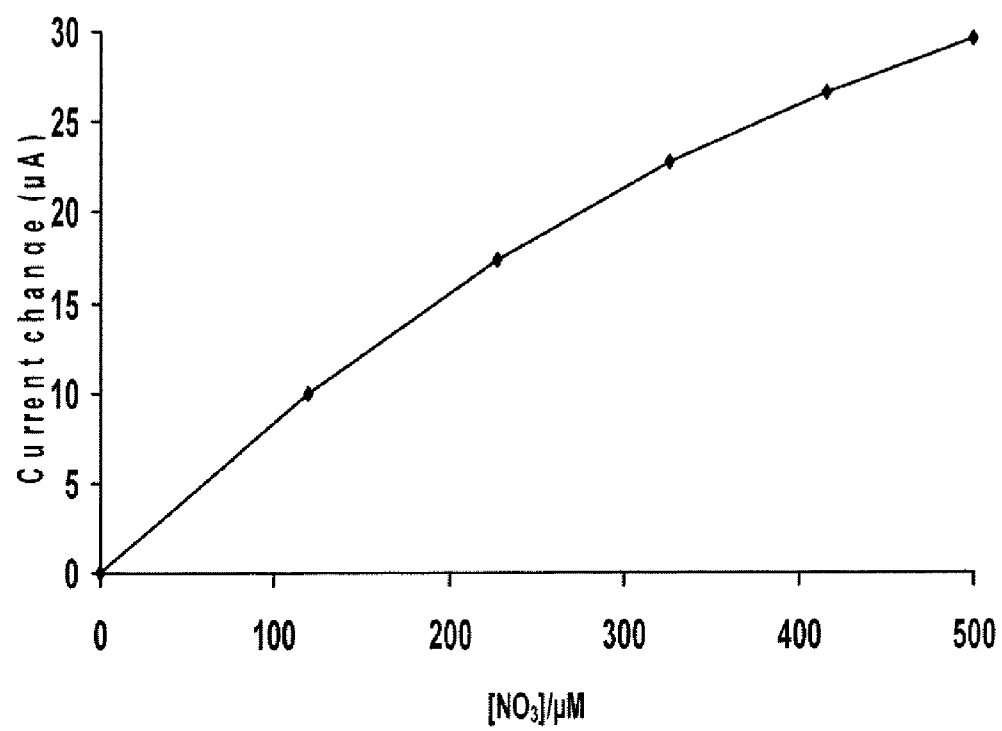
FIG. 22 is a graphical representation of a typical calibration plot for nitrate with the PPy-NaR—NaDH biosensor.

The optimised PPy-NaR—NADH biosensor gave amperometric responses which increased with nitrate concentration. A reasonably linear concentration range was obtained for nitrate from 0-500 µM, as illustrated in FIG. 22. The minimum detectable concentration of nitrate with the biosensor under the established conditions was 20 µM. No response was observed in absence of NaR, while the response was much reduced in the absence of NADH. This observation indicates that NADH plays a significant role in the observed amperometric response for nitrate. Further investigation of its role in the sensitivity of the nitrate response is therefore necessary.

Influence of NADH Concentration

The nitrate response obtained with the PPy-NaR—NADH biosensor increased with the increasing addition of β-NADH to the monomer solution up to 400 µM and gradually decreased beyond this concentration, possibly due to increased film thickness or lower enzyme concentration resulting from incorporation of higher concentration of NADH. A NADH concentration of 400 µM was therefore used for all further investigations. It is worth noting that the reproducibility of the nitrate response obtained at all NADH concentration was good. With the use of the optimum NADH concentration and other previously optimised conditions, the minimum detectable nitrate concentration with the PPy-NaR—NADH biosensor was 15 µM (1 ppm $NO_3$) and a linear concentration range of 50-500 µM was achieved. The achievable reproducibility within this concentration range was ±7.1%.

Example 14

Nitrate Biosensor with P-oPDA Outer Layer

A P-oPDA layer was formed on top of the inner PPy-NaR—NADH film by cyclic voltammetry carried out in a 0.5 M KCl/0.05 M phosphate buffer solution which contained 50 mM of oPDA from 0 to 600 mV. Irreversible oxidation processes are observed and oxidation is progressively hindered during prolonged cycling, as deduced from the anodic shift of the peak potential and the reduction in peak current.

Figure 23:
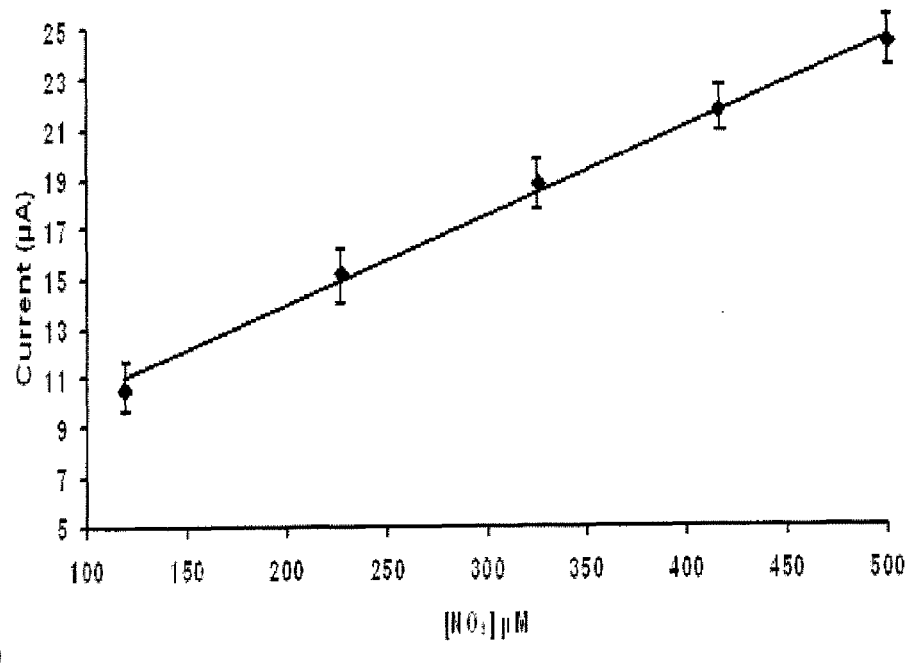
FIG. 23 is a comparison of calibration curves obtained with (a) optimised PPy-NaR—NADH and (b) PPy-NaR—NADH/P-oPDA biosensors.
Figure 23:
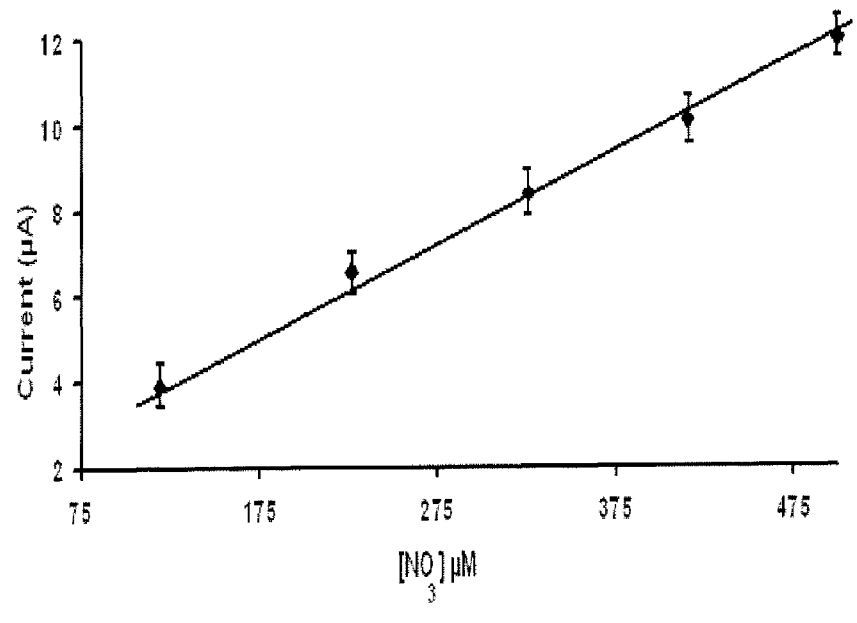

The nitrate response increased with increasing number of cycles up to 4 cycles and then decreased gradually due to increased P-oPDA layer thickness. The optimum nitrate response obtained with the P-oPDA outer layer produced with 4 cycles was only slightly less than that obtained without the P-oPDA layer, but the reproducibility was much improved at ±2.1%. This observation confirms that the inclusion of the P-oPDA outer layer did not have any significant effect on the amperometric response obtained for nitrate with the PPy-NaR—NADH biosensor. Furthermore, FIG. 23 shows that the nitrate response obtained with the biosensors with or without P-oPDA outer layer increased linearly with increasing nitrate concentration.

The nitrate response obtained with a film prepared from a composition containing 50 mM of oPDA, 0.5 M KCl and 0.05 M phosphate buffer was less than that obtained with barbitone buffer in polymerisation solution, but was significantly better than in the absence of buffer. This observation indicates that the presence of buffer in the oPDA polymerisation solution is necessary for retaining enzyme activity.

The addition of KCl to the oPDA polymerisation solution resulted in increasing nitrate response with up to 0.5 M KCl and beyond this concentration a slight decrease in nitrate response was observed. This KCl concentration was therefore used for all further investigations.

Example 15

Combined Electrode Designs

The use of combined electrode was investigated for the growth of the single layer (PPy-XOD-PNP—Fe(CN)$_6^{4-}$—AuNPs and PPy-NaR—NADH—AuNPs) and bilayer (PPy-XOD-PNP—Fe(CN)$_6^{4-}$—AuNPs/P-oPDA and PPy-NaR—NADH—AuNPs/P-oPDA) for detection of nitrate and phosphate. The various designs of combined electrode probe considered for this purpose and that can be used for fabrication of the bilayer biosensor are discussed below.

Combined Electrode-1

Figure 24:
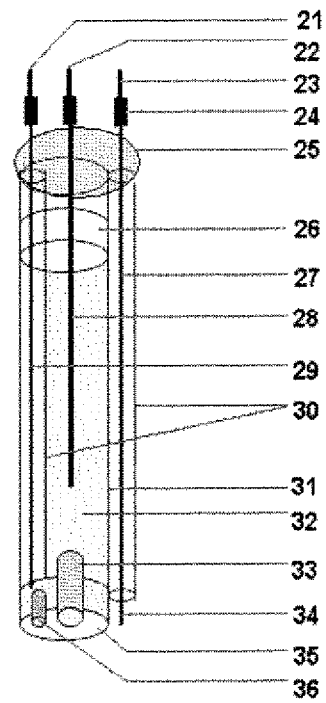
FIG. 24 provides a schematic diagram of combined electrode-1.

The combined electrode design-1 is shown in FIG. 24. A glass tube (31) was cut and ground and used as the main casing of the combined probe. The connecting wire (29) of working electrode (21) and the Pt-wire (27) (auxiliary electrode (23)) were sealed in glass capillaries (30). The auxiliary electrode (23) was kept outside the probe and had direct contact (34) with the measurement solution. The reference electrode (22) of Ag-wire (Ag/AgCl) (28) together with the working electrode (21) and auxiliary electrode were fixed in the glass tube (31) and capillary tube (30) by soft glue (25). The frit (33) and the platinum disc (36) of the working electrode (21) were mounted in epoxy glue (35). A soft plastic disc (25) was used at the top to fill the cell with KCl solution (32) using a syringe and needle. Copper connectors (24) were soldered on the top of the cell and connected to potentiostat with banana clips.

Combined Electrode-2

Figure 25:
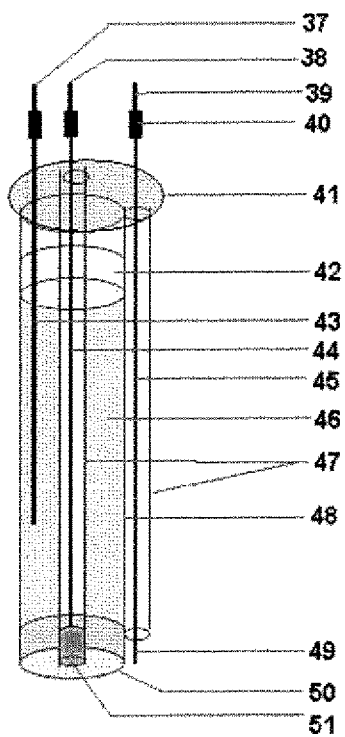
FIG. 25 provides a schematic diagram of combined electrode-2.

This design, as shown in FIG. 25, was the same as combined electrode-1 except that the working electrode (38) had its platinum disc (51) totally surrounded by a large frit (50). A glass tube (48) was cut and ground and used as the main casing of the combined probe. The connecting wire (44) of working electrode (38) and the Pt-wire (45) (auxiliary electrode (39)) were sealed in glass capillaries (47). The auxiliary electrode (39) was kept outside the probe and had direct contact (49) with the measurement solution. The reference electrode (37) of Ag-wire (Ag/AgCl) (43) together with the working electrode (38) and auxiliary electrode (39) were fixed in the glass tube (48) and capillary tube (47) by soft glue (41). A soft plastic disc (42) was used at the top to fill the cell with KCl solution (46) using a syringe and needle. Copper connectors (40) were soldered on the top of the cell and connected to potentiostat with banana clips.

Combined Electrode-3

Figure 26:
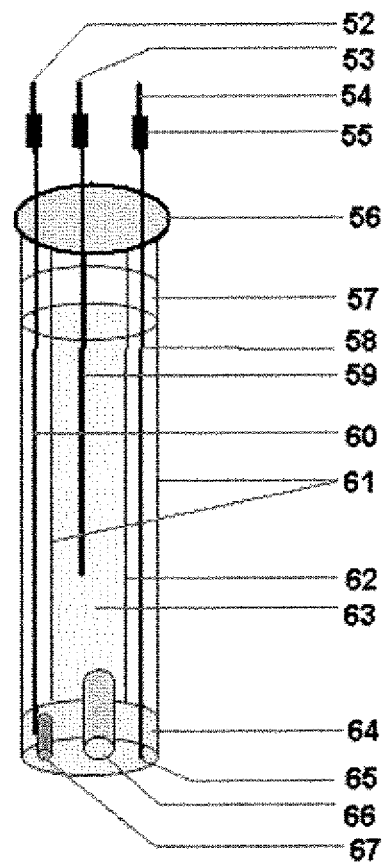
FIG. 26 provides a schematic diagram of combined electrode-3.

As seen in FIG. 26 the design of combined electrode-3 resembles the design of combined electrode-1 except that both glass capillaries (61) were present inside the probe and the auxiliary electrode (54) was also exposed to the surface through the epoxy glue (64). This design is useful especially for potentiometric measurements. A glass tube (62) was cut and ground and used as the main casing of the combined probe. The connecting wire (60) of working electrode (52) and the Pt-wire (58 and 65) (auxiliary electrode (54)) were sealed in glass capillaries (61). The reference electrode (53) of Ag-wire (Ag/AgCl) (59) together with the working electrode (52) and auxiliary electrode were fixed in the glass tube (62) and capillary tubes (61) by soft glue (56). The frit (66) and the platinum disc (67) of the working electrode (52) were mounted in epoxy glue (64). A soft plastic disc (57) was used at the top to fill the cell with KCl solution (63) using a syringe and needle. Copper connectors (55) were soldered on the top of the cell and connected to potentiostat with banana clips.

Combined Electrode-4

Figure 1:
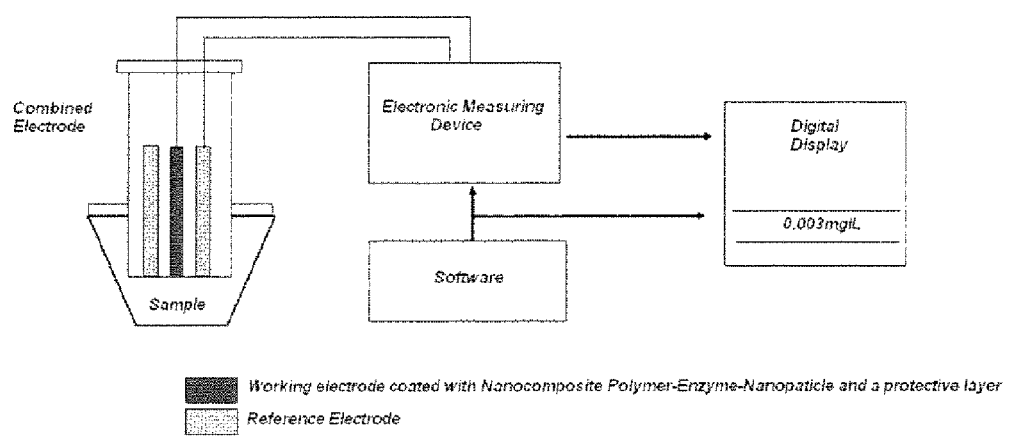
FIG. 1 is a schematic diagram of the electrochemical nanocomposite biosensor system.
Figure 2A:
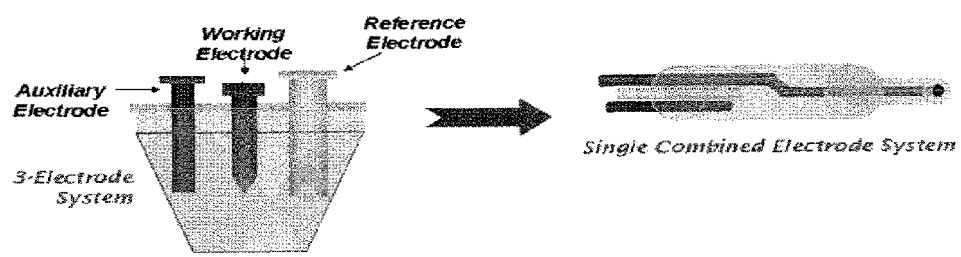
FIG. 2A is a schematic diagram showing the combination of three separate electrodes, a working electrode, a reference electrode and an auxiliary electrode into a combined 3-electrode system.
Figure 2B:
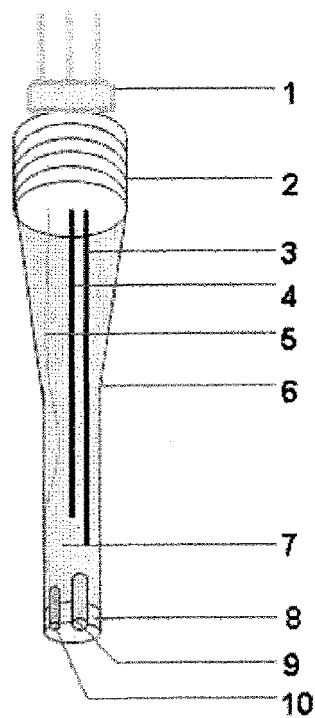
FIGS. 2B and 2C provide schematic diagrams showing examples of combined 3-electrode systems.

The combined electrode-4 is presented in FIG. 2B. In this design, a glass tube (6) with wider opening was used and a screw cap portion of plastic tube (2) was attached at this end. The screw cap was useful for cleaning auxiliary (3) and reference (4) wires and was convenient to fill or replace the KCl filling solution (7). A pin connector (1) was used for all three electrodes instead of long wires or connectors. Auxiliary (3) and reference (4) electrodes wires were located in the same solution inside the probe. A Pt-disc (10) was connected to the pin connector (1) by a thin plastic coated copper wire (5). This wire was long enough to remain intact while taking the Pt (3) and Ag/AgCl wires (4) out of the tube (nearly twice the length of Pt-wire). The frit (9) and the Pt disc (10) of the working electrode were mounted in epoxy glue (8).

Combined Electrode-5

Figure 2C:
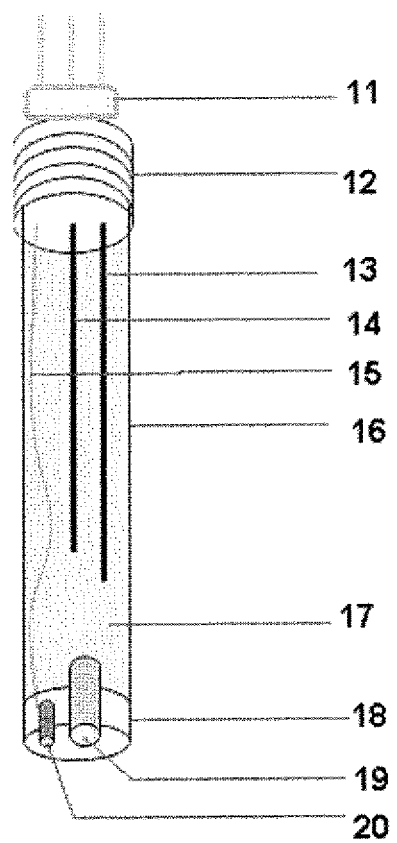
Figure 3A:
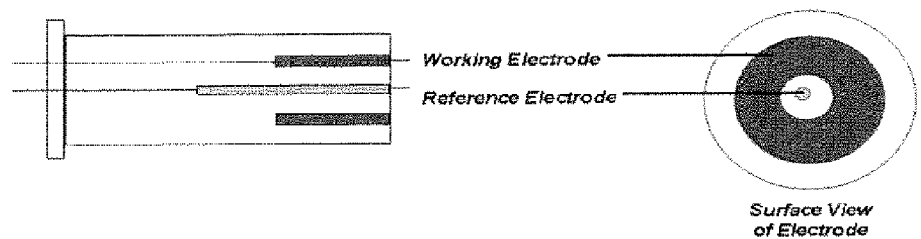
FIGS. 3A-3B are schematic diagrams showing different configurations of a combined electrode system comprising a working electrode and a reference electrode.
Figure 3B:
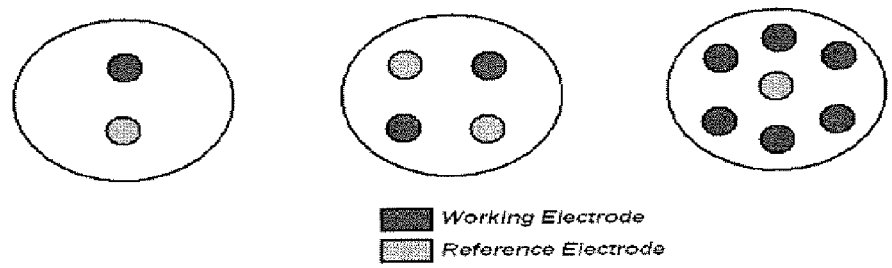

The design shown in FIG. 2C of combined electrode-5 is the same as for combined electrode-4 except that a glass tube of a wider and more uniform diameter was used to reduce the size of the combined probe. In this design, a glass tube (16) with wider opening was used and a screw cap portion of plastic tube (12) was attached at this end. The screw cap was useful for cleaning auxiliary (13) and reference (14) wires and was convenient to fill or replace the KCl filling solution (17). A pin connector (11) was used for all three electrodes instead of long wires or connectors. Auxiliary (13) and reference (14) electrodes wires were located in the same solution inside the probe. A Pt-disc (20) was connected to the pin connector (11) by a thin plastic coated copper wire (15). This wire was long enough to remain intact while taking the Pt (13) and Ag/AgCl wires (14) out of the tube (nearly twice the length of Pt-wire). The fit (19) and the Pt disc (20) of the working electrode were mounted in epoxy glue (18).

Combined Electrode-6

Figure 27:
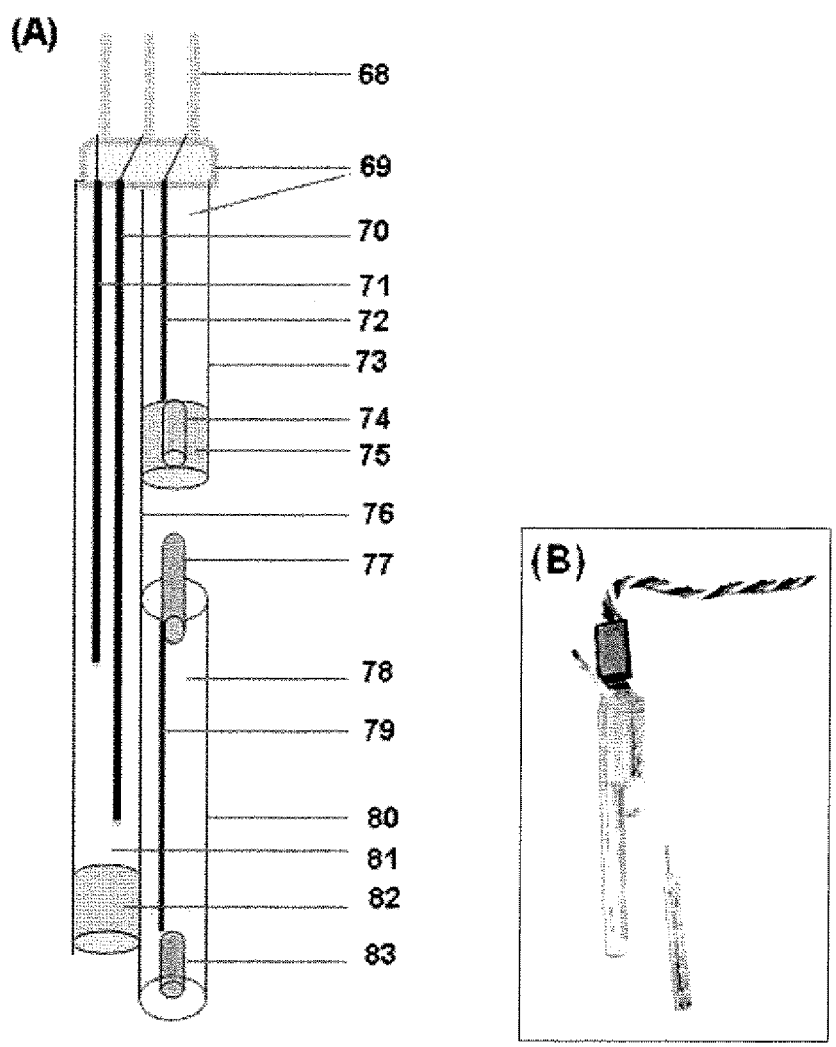
FIG. 27 provides (A) a schematic diagram of combined electrode probe-6 and (B) a fabricated combined electrode-6

The design of combined electrode-6 is shown in FIG. 27. This is a more refined form of previous combined electrode designs. The size of this probe is much smaller than previous designs and it has the advantage of permitting the working electrode to detach from the probe. The schematic diagram of combined electrode-6 is shown in FIG. 27A and an example of a fabricated probe is shown in FIG. 27B.

A glass tube (76) was used to house the working electrode silver wire (71) and the auxiliary electrode platinum wire (70). The glass tube (76) terminates with a frit (82) and is filled with electrolyte filling solution (81). The further glass tubes (73) and (80) house the working electrode and glass tube (80) is able to be detached or connected using a female connector (74) fitted in plastic (75) and a male connector (77). The working electrode platinum disc (83) is attached to the connector pin (68) for the working, auxiliary and reference electrodes by copper wires (72) and (79) fixed in place with epoxy glue (69) and (78).

The combined electrode-6 was the most preferred design in terms of size and ease of practical usage. This combined electrode was therefore investigated extensively for the growth of PPy-XOD-PNP—Fe(CN)$_6^{4-}$—AuNPs and PPy-XOD-PNP—Fe(CN)$_6^{4-}$—AuNPs/P-oPDA films for the detection of phosphate, as well as for the growth of PPy-NaR—NADH—AuNPs and PPy-NaR—NADH—AuNPs/P-oPDA films for the detection of nitrate.

Example 16

Amperometric Detection of Phosphate with Combined Electrodes
Combined Electrodes-4 and -5

Combined electrodes-4 and -5 were used to grow the PPy-XOD-PNP—Fe(CN)$_6^{4-}$—AuNPs films. These were subsequently optimised by considering some polymerisation parameter that can enhance phosphate response obtained with the PPy-XOD-PNP—Fe(CN)$_6^{4-}$—AuNPs biosensor.

Optimisation of Current Density

Figure 28:
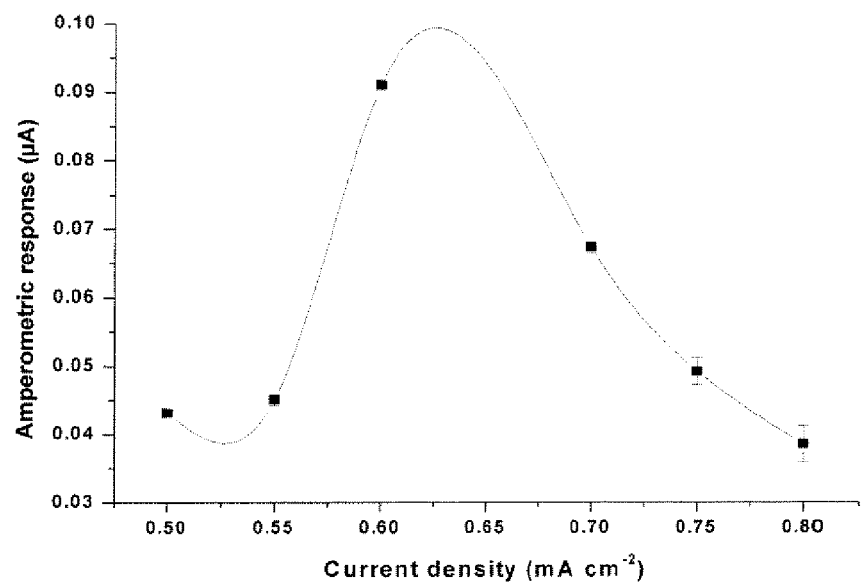
FIG. 28 is a graphical representation showing the effect of applied current density on the PPy-XOD-PNP—Fe(CN)$_6^{4-}$—AuNPs biosensor response using combined electrode-4. Monomer solution/condition: 0.1 M Py. 0.0005% AuNPs, 6 U/mL XOD, 48 U/mL XOD, 0.1 mM K$_4$Fe(CN)$_6$ and a polymerisation period of 120 seconds while various current densities were used for polymerisation of the PPy-XOD-PNP—Fe(CN)$_6^{4-}$—AuNPs films.

The optimum phosphate response of the PPy-XOD-PNP—Fe(CN)$_6^{4-}$—AuNPs film grown on modified combined electrode-4 was obtained with an applied current density of 0.6 mA cm$^{-2}$, as evident in FIG. 28. An initial increase in biosensor response was observed up to this optimum current density and a decrease in phosphate response was observed at higher current densities. Current densities higher than previously optimised PPy-XOD-PNP—Fe(CN)$_6^{4-}$—AuNPs biosensor were required for growth of the same films on combined electrodes-4 and -5.

Optimisation of Polymerisation Period

Figure 29:
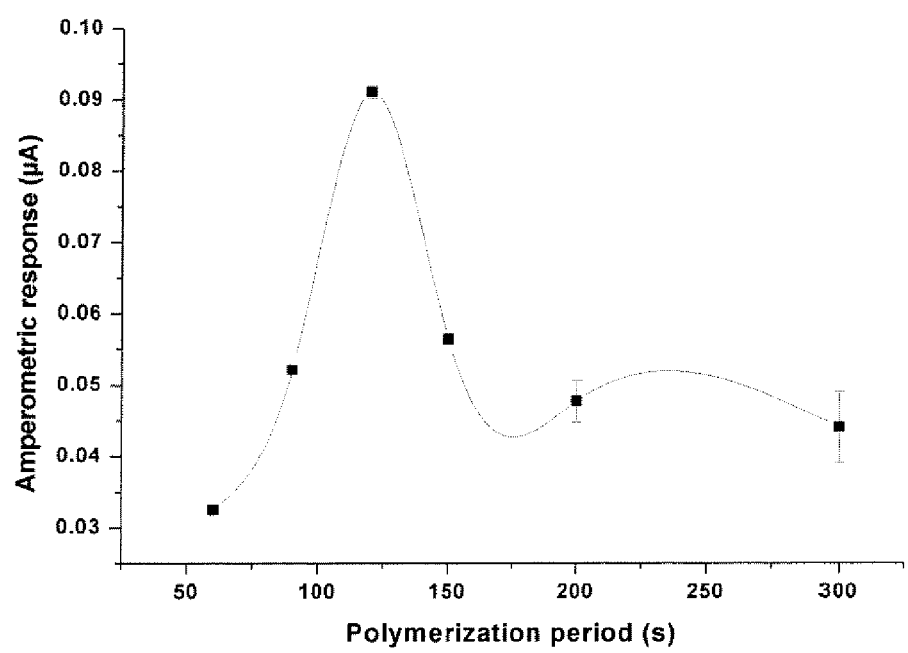
FIG. 29 is a graphical representation showing the effect of polymerization period on the PPy-XOD-PNP—Fe(CN)$_6^{4-}$—AuNPs biosensor response using combined electrode-4.

FIG. 29 shows variation of the PPy-XOD-PNP—Fe(CN)$_6^{4-}$—AuNPs biosensor response with increasing polymerisation period. The PPy-XOD-PNP—Fe(CN)$_6^{4-}$-AuNPs film was grown on the combined electrode-4. An increase in the polymerisation period used for the growth of PPy-XOD-PNP—Fe(CN)$_6^{4-}$—AuNPs films up to 120 seconds results in an increase in the sensitivity of the amperometric response and a further increase in polymerisation period increases the film thickness and, hence, decreased the phosphate response.

Optimisation of $K_4Fe(CN)_6$ Concentration

FIG. 30 shows the effect of increasing $K_4Fe(CN)_6$ concentration used for the growth of PPy-XOD-PNP—$Fe(CN)_6^{4-}$—AuNPs film on phosphate response. The use of 0.1 M $K_4Fe(CN)_6$ gave optimum phosphate response for PPy-XOD-PNP—$Fe(CN)_6^{4-}$—AuNPs biosensor.

Optimisation of AuNPs Concentration

The addition of 0.0005% of AuNPs to the monomer solution gave an optimum amperometric response for the PPy-XOD-PNP—$Fe(CN)_6^{4-}$—AuNPs biosensor on combined electrode-4 as shown in FIG. 31.

Analytical Performance

The optimised PPy-XOD-PNP—$Fe(CN)_6^{4-}$—AuNPs film biosensors grown on combined electrode-4 gave good response for phosphate. Typical amperograms are shown in FIG. 32A where 'a' represents an increase in response with an injection of 454.5 µM phosphate to the measurement solution. FIG. 32B shows a typical calibration plot for PPy-XOD-PNP—$Fe(CN)_6^{4-}$—AuNPs film biosensor grown on combined electrode-4.

Example 17

Combined Electrode 6

Combined electrodes-4 and -5 have been used to optimise current density, polymerisation period, AuNPs and ferrocyanide concentrations for amperometric detection of phosphate. In this section, further investigations were carried out using combined electrode-6 for fabrication of single layer PPy-XOD-PNP—$Fe(CN)_6^{4-}$—AuNPs and bilayer PPy-XOD-PNP—$Fe(CN)_6^{4-}$—AuNPs/P-o-PDA biosensors. The investigations carried out to optimise the use of these biosensors for amperometric detection of phosphate are described below.

Enzyme Concentrations

While maintaining the previously optimized XOD and PNP enzyme ratio 1:8, the influence of increasing enzyme concentrations on phosphate response is shown in FIG. 33. The phosphate response obtained with the single layer PPy-XOD-PNP—$Fe(CN)_6^{4-}$—AuNPs biosensor grown on combined electrode-6 was much higher than that obtained with combined electrodes-4 and -5. Interestingly, only half of the XOD and PNP concentrations was required with combined electrode-6.

Pyrrole Concentration

The variation of phosphate response with varying pyrrole concentrations used for the growth of PPy-XOD-PNP—$Fe(CN)_6^{4-}$—AuNPs biosensor on combined electrode-6 is shown in FIG. 34. A pyrrole concentration of 0.1 M gave optimum phosphate response for single layer PPy-XOD-PNP—$Fe(CN)_6^{4-}$—AuNPs biosensor.

Influence of Outer P-oPDA Layer

The fabrication of an outer layer of poly-ortho-phenylenediamine (P-oPDA) was achieved by cyclic voltammetry in a 50 mM solution of oPDA which contained barbitone buffer and KCl. The combined electrode-6 with the PPy-XOD-PNP—$Fe(CN)_6^{4-}$AuNPs film was cycled between 0 and 800 mV at varying scan rates and number of scans to grow the outer P-o-PDA layer.

Optimisation of Number of Scans

FIG. 35 shows the variation of the biosensor response with increasing number of scans used for the growth of P-oPDA layer over PPy-XOD-PNP—$Fe(CN)_6^{4-}$—AuNPs. The amperometric response increased with increasing scans for up to 7 scans and decreased with further increase in number of scans. Initial increase in number of scans increased the protective layer for the inner enzyme layer but this layer becomes more insulating for the inner PPy-XOD-PNP—$Fe(CN)_6^{4-}$—AuNPs layer when more more than 7 scans is used, resulting in decreased phosphate response.

Optimisation of Scan Rate

The influence of scan rates used to grow the outer layer on the amperometric response for phosphate with the PPy-XOD-PNP—$Fe(CN)_6^{4-}$—AuNPs/P-oPDA biosensor is illustrated in FIG. 36. The use of a scan rate of 125 mV/s gave optimum phosphate response. Increase in the thickness of the outer P-oPDA layer formed at the lower scan rates increased the diffusion barrier and, consequently, reduced the resulting amperometric response.

Optimisation of Barbitone Buffer Concentration

FIG. 37 shows that the phosphate response increased with increasing barbitone buffer concentration used for the growth of the outer P-oPDA layer. A buffer concentration of 75 mM gave optimum amperometric response for phosphate with the PPy-XOD-PNP—$Fe(CN)_6^{4-}$—AuNPs/P-oPDA biosensor. A decrease in response at higher concentrations may be due to variation in counter anionic species entrapped during the growth of P-oPDA layer or increased layer thickness.

Optimisation of KCl Concentration

FIG. 38 shows that the amperometric response obtained with the PPy-XOD-PNP—$Fe(CN)_6^{4-}$—AuNPs/P-oPDA biosensor increased with increasing KCl concentration used for the growth of the outer P-oPDA layer is shown in. The addition of 0.5 M of KCl to the polymerisation solution gave the best P-oPDA film thickness for obtaining optimum phosphate response.

Influence of oPDA Concentration

The influence of the oPDA concentration used for the growth of the outer layer on the phosphate response of bilayer biosensor is shown in FIG. 39. Optimum phosphate response was obtained with the use of an oPDA concentration of 50 mM.

Influence of Scanning Potential Range

The formation of the outer layer can be significantly influenced by the choice of scanning potential range. FIG. 40 shows that the optimum scanning potential range for the growth of the outer P-oPDA layer over PPy-XOD-PNP—$Fe(CN)_6^{4-}$—AuNPs was between 0 and 800 mV. Much lower amperometric responses were obtained for phosphate when scanning potential ranges of 0-200, 0-400, 0-600 and 0-1000 mV were used. This was due to increased film thickness when a scanning potential range of 0-1000 mV was used, whereas insufficient film thickness was an issue for other scanning potential ranges.

Analytical Performance

The PPy-XOD-PNP—$Fe(CN)_6^{4-}$—AuNPs/P-oPDA bilayer biosensor grown on combined electrode-6 gave good amperometric response for phosphate. This response increased with corresponding increase in phosphate concentration as shown in FIG. 41A. A typical calibration plot obtained for phosphate with the PPy-XOD-PNP—$Fe(CN)_6^{4-}$—AuNPs/P-oPDA bilayer biosensor grown on combined electrode-6 is shown in FIG. 41B.

FIG. 42A shows the photographic views of the combined electrode-6 from different angles. The schematic diagrams of the combined electrode-6, pin connector and teflon tubing are shown in FIGS. 42B, 42C and 42D respectively. The measurements were important for proper alignment of working electrode into the connector.

Example 18

Potentiometric Detection of Phosphate with Combined Electrode-6
Optimisation

The use of the combined electrode-6 for potentiometric detection of phosphate with single layer PPy-XOD-PNP—Fe(CN)$_6^{4-}$—AuNPs and bilayer PPy-XOD-PNP—Fe(CN)$_6^{4-}$—AuNPs/P-oPDA biosensor was also investigated. This required similar optimisation to those conducted for amperometric detection. Initially, it was thought that the optimisation of only a few parameters would be required. However, it was found that a complete optimisation was necessary to obtain optimum potentiometric response for phosphate. To avoid repetitive presentation of similar diagrams shown already for amperometric measurements, only the optimum parameters are summarised below:

Enzyme concentration: 2 U/mL XOD and 16 U/mL PNP;
Pyrrole concentration: 0.5 M;
AuNPs concentration: 0.00025%;
K$_4$Fe(CN)$_6$ concentration: 0.2 mM;
Applied current density: 0.8 mA cm$^{-2}$;
Polymerization period: 120 seconds;
oPDA concentration: 10 mM;
Barbitone buffer concentration: 75 mM;
KCl concentration: 0.5 M;
Number of scans: 6; and
Scanning potential range: 0-800 mV Influence of Choice of Buffer and pH Different types of buffer solutions were used to investigate the possibility of further increasing the potentiometric response of phosphate obtained with the bilayer PPy-XOD-PNP—Fe(CN)$_6^{4-}$—AuNPs/P-oPDA biosensor fabricated with combined electrode-6. FIG. 43 shows that the phosphate response obtained with barbitone buffer was much higher than those obtained with the other buffers and was chosen for this reason. However, the results also indicate that ammonium chloride-EDTA buffer (AmCEB) is an alternative buffer where there is concern about using barbitone buffer.

FIG. 44 shows that the optimum pH for potentiometric measurement of phosphate with the bilayer PPy-XOD-PNP—Fe(CN)$_6^{4-}$—AuNPs/P-oPDA biosensor was was 6.0. A higher or lower pH can cause changes in the conformational geometry and ionic interactions at the active sites and can result in a lower phosphate response.

Interference Study

Most natural waters and biological samples contain numerous electroactive species. These species can affect phosphate response during the determination of phosphate. The following common interferants did not affect phosphate potentiometric response for 500 to 870 μM phosphate on the combine electrode-6 coated with PPy-XOD-PNP—Fe(CN)$_6^{4-}$—AuNPs/P-oPDA bilayer:

Ascorbic acid up to 1 mM;
Sulfate up to 1.0 mM;
Acetate when present at ≤1 mM;
Nitrite up to 1.0 mM;
Carbonate concentrations ≤0.5 mM;
Chloride: up to 5.0 mM;
Mercury: up to 100 ppb;
Lead concentrations: up to 100 ppb;
Cadmium concentration: up to 5 ppb; and
Nickel concentration: up to 100 ppb.

Analytical Performance

The bilayer PPy-XOD-PNP—Fe(CN)$_6^{4-}$—AuNPs/P-oPDA bilayer biosensor grown on combined electrode-6 gave very good potentiometric response for phosphate. The minimum detectable phosphate concentration with the fully optimized bilayer PPy-XOD-PNP—Fe(CN)$_6^{4-}$—AuNPs/P-oPDA biosensor by potentiometric detection was 0.077 μM phosphate ions (0.0073 ppm or 0.0024 PO$_4^{3-}$—P). Phosphate potentiometric response is shown in FIGS. 45A and 45C and typical calibration curves are shown in FIGS. 45B and 45D.

Effect of Temperature

The variation of temperature had a significant effect on the phosphate response of the bilayer PPy-XOD-PNP—Fe(CN)$_6^{4-}$—AuNPs/P-oPDA biosensor. The data in Table 6 shows that the biosensor works very well within a temperature range of 20-50° C. In particular, an increased biosensor response was observed between 30 and 40° C. possibly due to enhanced enzyme activity within this temperature range. Evidently, the optimum phosphate response was obtained at 35° C. The decreased biosensor response above 50° C. may be due to reduced enzyme activity caused by denaturation of the enzyme at the higher temperature.

TABLE 6

Effect of temperature on potentiometric response

| Temperature (° C.) | Response (mV) | % Change in response |
|---|---|---|
| 20 ± 0.2 | 32.20 | 0 |
| 25 ± 0.2 | 32.15 | −0.16 |
| 30 ± 0.7 | 32.25 | +0.16 |
| 35 ± 0.4 | 38.30 | +18.9 |
| 40 ± 0.4 | 31.45 | −2.30 |
| 50 ± 0.6 | 31.30 | −2.80 |
| 60 ± 0.8 | 25.35 | −21.3 |

Application to Water Samples

Recovery study was carried out with tap water to determine the effectiveness of the bilayer PPy-XOD-PNP—Fe(CN)$_6^{4-}$—AuNPs/P-oPDA biosensor for detection of phosphate. 93-98 percent recovery was obtained for phosphate concentrations between 0.4 and 1.5 μM as shown in Table 7. The results clearly indicate that the bilayer biosensor can be reliably used for the determination of phosphate;

TABLE 7

Recovery of phosphate in tap water

| [PO$_4^{3-}$] added (μM) | [PO$_4^{3-}$] detected (μM) | RSD (%, n = 3) | % Recovery |
|---|---|---|---|
| 0 | 0.02 | 8 | — |
| 0.42 | 0.42 | 4.7 | 96 |
| 0.80 | 0.80 | 2.4 | 98 |
| 1.16 | 1.09 | 3.7 | 94 |
| 1.49 | 1.38 | 2.9 | 93 |

Phosphate concentrations in water samples collected from Mt Buller which include some near pristine waters and some treated wastewaters, were analysed with the bilayer PPy-XOD-PNP—Fe(CN)$_6^{4-}$—AuNPs/P-oPDA biosensor fabricated with the combined electrode-6. A brief description of the unknown samples and the phosphate concentrations obtained with biosensor and compared with results obtained by a NATA approved FRP ascorbic acid reduced phosphomolybdenum blue method are presented in Table 8. Frozen samples were left overnight at room temperature and filtered (pore size 0.45 μm) before analysis. Standard addition method was used to determine the phosphate concentration in unknown samples. The results in Table 8 show that there is generally good agreement between the concentration and trend of results obtained by both methods.

TABLE 8

Phosphate determination in unknown water samples

| Sample | Sample code | Colour | pH | $[PO_4^{3-}]$ (μM) | $[PO_4^{3-}]$ (ppm) | $[PO_4^{3-}\text{-P}]$ (ppm) | $[PO_4^{3-}\text{-P}]$ (ppm)* |
|---|---|---|---|---|---|---|---|
| A | 6265 | Colourless | 5-6 | 4.5 ± 0.14 | 0.427 ± 0.014 | 0.139 ± 0.004 | 0.16 |
| B | 5367 | Colourless | 6-7 | 0.235 ± 0.08 | 0.022 ± 0.007 | 0.0073 ± 0.0025 | 0.003 |
| C | 5375 | Colourless | 5-6 | 0.475 ± 0.04 | 0.045 ± 0.004 | 0.015 ± 0.0014 | 0.008 |
| D | 5377 | Colourless | 5-6 | 0.165 ± 0.02 | 0.0157 ± 0.002 | 0.005 ± 0.0008 | 0.002 |
| E | 6118 | Slightly yellow | 5-6 | 4.2 ± 0.09 | 0.399 ± 0.009 | 0.130 ± 0.028 | 0.18 |
| F | 6119 | Slightly yellow | 5-6 | 7.5 ± 0.12 | 0.713 ± 0.012 | 0.232 ± 0.004 | 0.44 |

*Obtained by NATA approved FRP ascorbic acid reduced phosphomolybdenum blue method Further analysis of phosphate concentrations in other natural water samples obtained by spectrophotometry and PPy-XOD-PNP—Fe(CN)$_6^{4-}$—AuNPs/P-oPDA biosensor methods also show a good agreement, as demonstrated by the data in Table 9.

TABLE 9

Phosphate determination in natural water samples

| Sample | Sample code | Colour | pH | $[PO_4^{3-}]$ (ppm) Spectrophotometric method | Biosensor method |
|---|---|---|---|---|---|
| Monash Gippsland Campus Lake | MGCL | Colourless | 7.0 | 0.437 ± 0.002 | 0.482 ± 0.02 |
| Lake Hyland | HL | Colourless | 6-7 | 0.114 ± 0.001 | 0.120 ± 0.02 |
| Eel Hole Creek | EHC | Slightly yellow | 6.0 | 0.104 ± 0.002 | 0.082 ± 0.01 |
| Hazelwood Pondage | HP | Colourless | 8.0 | 0.522 ± 0.001 | 0.583 ± 0.04 |
| Coalition Creek | CC | Colourless | 6.0 | 0.123 ± 0.002 | 0.136 ± 0.02 |
| Tidal River | TR | Slightly yellow | 6.0 | 0.019 ± 0.001 | 0.011 ± 0.006 |
| Tap Water | TW | Colourless | 7.0 | 0.171 ± 0.003 | 0.201 ± 0.04 |

Example 19

Amperometric Detection of Nitrate with Combined Electrode-6

Entrapment of NaR, AuNP, NADH

FIG. 46(a) shows that AuNP, NaR and NADH were successfully incorporated into a polypyrrole film on the combined electrode and similarly FIG. 46(b) shows the successful incorporation of NaR and NADH in polypyrrole film in the absence of AuNPs. A decrease in potential was observed in the first 10 s indicating the commencement of film formation. Higher potential (897 mV) was reached prior to commencement of polymerisation in the monomer solution which contained AuNP, NaR, NADH compared to that of a monomer solution in which AuNPs were absent (839 mV). This indicates that the incorporation of AuNPs, as well as NaR and NADH in the PPy film required extra effort. However, the potential for the growth of the PPy-AuNP—NaR—NADH film (FIG. 46(a)) decreased to a much lower value than for the PPy-NaR—NADH film (FIG. 46(b)), indicating that the former is more conductive. This is expected as the incorporation of the AuNPs should result in an increase in conductivity.

Effect of Applied Potential

The effect of applied potential on the amperometric response of combined PPy-AuNP—NaR—NADH electrode was similar to that observed in the absence of AuNPs (combined PPy-NaR—NADH electrode). However, as shown in FIG. 47, optimum response was obtained at −175 mV. The inclusion of nanoparticles shifted the optimum voltage for nitrate response from −200mV to −175 mV. This observation was identical to that observed for the uncombined electrode PPy-NaR—NADH and PPy-AuNP—NaR—NADH nitrate biosenors. An applied potential of −175 mV was therefore chosen for future amperometric investigations with the combined PPy-AuNP—NaR—NADH nitrate biosensor.

AuNP Concentration

FIG. 48 shows that the optimum response for nitrate was obtained when 0.0005% AuNPs was used in the polymerisation solution. Further increase in AuNP concentration resulted in a decrease in the amperometric response for nitrate, possibly due to increased film thickness. Therefore, 0.0005% AuNPs was used in all further investigations.

Influence of Pyrrole Concentration, Polymerization Period and Current Density

FIG. 49 shows that optimum amperometric response was observed when a pyrrole concentration of 0.5 M was used for formation of PPy-AuNP—NaR—NADH film. Further increase in pyrrole concentration resulted in a slight decrease in the amperometric response due to the increased film thickness which increases the diffusion barrier. The reproducibility of the nitrate response also increased with increasing pyrrole concentration.

The effect of variation of the polymerisation period on the amperometric response of nitrate is shown in FIG. 50. The response increased with increasing polymerisation period up to 180 s and then decreased slowly with further increase in polymerisation time. Decrease in the nitrate response with the increasing polymerisation period was again due to increase in film thickness. Hence, a polymerization period of 180 s was chosen all further investigations.

The potassium chloride concentration used as an electrolyte for the growth of conducting PPy-AuNP—NaR—NADH films was also optimised. In the absence of KCl, a very high potential (2000 mV) was reached during film growth and as this may lead to denaturation of the enzyme it was necessary to use supporting electrolyte to promote polymerisation at lower potential. Thus, possible influence of the addition of KCl on film growth and ultimately on the amperometric response for nitrate was investigated. As shown in FIG. 51, optimum amperometric response for nitrate was observed when 0.2 M KCl was added. Thus for all investigations, 0.2 M KCl was used to improve conductivity of monomer solution and to ease the commencement of film formation.

Influence of Applied Current Density

FIG. 52 shows that the optimum amperometric response for nitrate was obtained when a current density of 0.5 mA/cm$^2$ was employed for film growth. Further increase in the applied current density decreased the response due to the more rapid polymerisation which may decrease the amount of enzyme and AuNPs incorporated in the film. This may also result in increased film thickness and diffusion barrier. An applied current density of 0.5 mA/cm$^2$ was therefore chosen for growing the PPy-AuNP—NaR—NADH film on the combined electrode in all further investigations.

Influence of NADH and NaR Concentrations

The influence of NADH concentration, in the polymer film, on the amperometric response for nitrate, was investigated. The NADH concentration was varied from 100-600 μM. As shown in FIG. 53 the optimum amperometric response for nitrate was obtained when 400 μM of NADH were used in polymerisation solution. Even the presence of a very small amount of NADH (100 μM) increased the amperometric nitrate response considerably, indicating that only a small amount of NADH is required for NaR to be catalytically effective. However when NADH concentration was increased beyond 400 μM the nitrate response started to decrease, possibly due to increased film thickness. Thus, 400 μM of NADH was chosen as optimum NADH concentration.

The enzyme (NaR) concentration used for the formation of PPy-NaR—NADH film was varied from 250 to 2000 mU/mL. FIG. 54 shows that the nitrate response increased with increasing NaR concentration used in the monomer solution. The optimum nitrate response was obtained with 500 mU/mL of NaR in the monomer solution. Further increase in enzyme concentration resulted in slight decrease in amperometric response for nitrate. It is interesting to note that the amount of NaR required for optimum nitrate response with the combined PPy-AuNP—NaR—NADH electrode was half of that required in the absence of AuNPs (combined PPy-NaR—NADH electrode). This suggests that the presence presence of Au-nanoparticles improves the incorporation of the enzyme in the PPy film.

Fabrication of Bilayer PPy-ANP—NaR—NADH/P-oPDA Biosensor

The growth of the outer P-oPDA layer was evident from cyclic voltammogram shown in FIG. 55. The polymerisation of oPDA was observed from an anodic peak at about 400-500 mV. Oxidation is progressively hindered on the surface of working electrode during prolonged cycling as shown by the anodic shift of the peak potential and decrease in peak current with increasing number of cycle. It was observed that with the addition of the P-oPDA outer layer the sensitivity of the nitrate response increased significantly.

Optimization of o-PDA Concentration

FIG. 56 shows that the optimum nitrate response (±2%) was obtained when 50 mM of oPDA was used with four cycles. An increase in the oPDA concentration resulted in a decrease in the amperometric nitrate response due to increase in film thickness at higher o-PDA concentrations. 50 mM of oPDA was therefore used for in all further investigations.

Influence of KCl Concentration

KCl was used as an electrolyte to promote polymerisation of oPDA. FIG. 57 shows that the amperometric response for nitrate decreased when KCl concentration was increased beyond 0.4 M possibly due to increasing P-oPDA film thickness. Consequently, 0.3 M KCl was used in all future investigations.

Influence of Number of CV Cycles

The influence of number of cycles to grow P-oPDA film on the amperometric response for nitrate was investigated. FIG. 58 shows that an increase in the number of cycles beyond four reduced the sensitivity of the nitrate response started to decrease. Increase in P-oPDA film thickness with increase in number of CV is responsible for the decreased nitrate response.

Effect of Buffer Concentration

FIG. 59 shows that the increasing buffer concentration affected the sensitivity of the amperometric response of PPy-AuNP—NaR—NADH/P-oPDA nitrate biosensor. Evidently the nitrate response was suppressed when phosphate buffer concentrations (pH 7.3) are increased. The increase in buffer concentration from 0.05 M to 0.5 M results in 45% decrease in nitrate response. The magnitude of the response obtained in 0.2 M buffer concentration was 12-15% less than that of 0.1 M phosphate buffer. However, the effect of interferents decreased substantially at higher buffer concentrations. Thus, the use of higher concentration of buffer solution enabled better tolerance of higher concentrations of interferents.

Analytical Performance

As shown in FIG. 60 the nitrate response obtained with the PPy-AuNP—NaR—NADH/P-oPDA electrode increased with increasing nitrate concentration. Although, in the case of PPy-NaR—NADH/P-oPDA electrode the nitrate response obtained with the addition of the same amount of nitrate is slightly less than that of PPy-AuNP—NaR—NADH electrode, the amperometric response for nitrate with PPy-NaR—NADH/P-oPDA gave much less noise and less percentage error (~2%, n=3). As shown in FIG. 61 a linear concentration range of 1-1000 μM nitrate and a minimum detectable concentration of 0.1 μM were achieved with the combined bilayer PPy-AuNP—NaR—NADH/P-oPDA electrode.

FIG. 62 shows the comparison of all the amperometric biosensors fabricated to date. The amount of current generated for the same quantity of nitrate with all the combined electrodes is higher than that with segregated electrodes. The nitrate response increased considerably with the inclusion of Au-nanoparticles in the polymer film. As shown in Table 10 the combined PPy-AuNp-NaR—NADH and combined PPy-AuNP—NaR—NADH/P-oPDA electrodes have the better linear concentration range and minimum detectable concentration limit.

TABLE 10

Comparison of the performance of the different configuration of nitrate biosensors fabricated with the combined electrode and individual (uncombined) electrode arrangement

| Biosensor | Current density for 500 μM NO$_3$ | Linear Conc range (μM) | MDC (μM) |
| --- | --- | --- | --- |
| PPy-NaR-NADH | 29.6 | 100-500 | 15 |
| PPy-NaR-NADH/P-oPDA | 22.4 | 100-500 | 15 |
| PPy-AuNP-NaR-NADH | 38 | 10-500 | 0.2 |
| PPy-AuNP-NaR-NADH/P-oPDA | 32 | 10-500 | 0.2 |
| Comb PPy-NaR-NADH | 36 | 100-800 | 5 |
| Comb PPy-AuNP-NaR-NADH | 67 | 1-1000 | 0.1 |
| Comb PPy-AuNP-NaR-NADH/P-oPDA | 61 | 1-1000 | 0.1 |

Interference Study

When measuring real samples the amperometric nitrate response of PPy-AuNp—NaR—NADH/P-oPDA biosensor can be affected by the presence of other ions of the same charge sign i.e; negatively charged ions. The use of the bilayer biosensor fabricated on the combined electrode-6 design for measurement of 500 μM nitrate was not affected by the following:

Phosphate: up to 600 μM;
Acetate: up to 500 μM;

Sulphate: up to 400 µM;

Carbonate: up to 200 µM;

Hydroxide: up to 400 µM;

Chloride: up to 200 µM;

Influence of Temperature

FIG. 63 shows that the nitrate response increased with increasing measurement solution temperature up to 45° C. Beyond this temperature, the response of the PPy-AuNP—NaR—NADH/P-oPDA biosensor decreased rapidly, indicating that the optimum temperature for the biosensor is 45° C.

Application to Water Samples

Recovery study was conducted for the determination of nitrate with the bilayer PPy-AuNP—NaR—NADH/P-oPDA amperometric biosensor fabricated with the combined electrode-6 design. The data in Table 11 shows that 94-97% recovery with a RSD of 2.1-3.6% was obtained for 10-500 µM of nitrate. These results confirmed that the bilayer PPy-AuNP—NaR—NADH/P-oPDA amperometric biosensor can be used reliably for determination of nitrate in water.

TABLE 11

Recovery of nitrate in water with the bilayer PPy-AuNP-NaR-NADH/P-oPDA amperometric biosensor

| Added amount of $NO_3^-$ (µM) | Found amount of $NO_3^-$ (µM) | RSD (%, n = 3) | Recovery (%) |
|---|---|---|---|
| 0 | 68 (4.2 ppm*) | 2.1 | |
| 10 | 73.8 | 3.6 | 94.6 |
| 100 | 160.2 | 2.6 | 97.2 |
| 200 | 251.5 | 2.4 | 93.8 |
| 500 | 540.5 | 3.2 | 95.1 |

*1 ppm $NO_3^-$ = 16.12 µM

The use of the bilayer PPy-AuNP—NaR—NADH/P-oPDA nitrate biosensor for reliable determination of nitrate in water samples was also investigated by use of standard additions method. The results in Table 12 show that there is generally good agreement between the results obtained with the biosensor and a spectrophotometric method.

TABLE 12

Comparison of nitrate concentrations obtained in water samples with the PPy-AuNP-NaR-NADH/P-oPDA amperometric biosensor and a spectrophotometric method

| Sample | PPy-AuNP-NaR-NADH/P-oPDA Biosensor (ppm) | Spectrophotometric method (ppm) |
|---|---|---|
| Tap water | 4.2 ± 0.4 | 1.4 |
| Hyland lake | 10.5 ± 1.5 | 12 |
| Latorbe River | 4.5 ± 0.5 | 1.3 |
| Hazelwood Pondage | 8.5 ± 1.4 | 7.7 |
| Inverloch sea | 15.1 ± 1.9 | 17 |
| Coaltion creek | 1.5 ± 0.3 | 0.5 |
| Tidal river | 10.6 ± 1.6 | 11.4 |
| Eel hole creek | 7.4 ± 1.2 | 8.6 |
| Golf course lake (Monash gippsland) | 11.2 ± 1.9 | 13.1 |

The application of the biosensor to the determination of nitrate concentration in water samples collected from Mt Buller which includes some near pristine waters and some treated wastewaters was also successful, as demonstrated in Table 13.

TABLE 13

Nitrate concentrations found in water samples collected from Mt Buller

| Sample | $NO_3^-$—N (ppm) | $NO_3^-$—N (ppm)* |
|---|---|---|
| 5375 | 4.6 ± 0.2 | 4.7 |
| 6265a | 0.95 ± 0.10 | 0.82 |
| 6118 | 0.21 ± 0.08 | 0.33 |
| 6119 | 0.16 ± 0.05 | 0.18 |
| 5377 | <0.008 | 0.005 |
| 5367 | <0.008 | 0.005 |

*NATA approved Cd-reduction/Griess reaction for NOx

The claims defining the invention are as follows:

1. An electrode for use in an electrochemical sensor, comprising
    i) a conducting substrate;
    ii) a conducting polymeric film disposed on the conducting substrate, and in which at least one biocatalyst or other bioreceptor has been immobilised, and wherein the conducting polymeric film comprises metallic nanoparticles, the thickness of the polymeric film being in the range of 20 nm to 170 nm; and
    iii) a porous coating disposed on at least a portion of the polymeric film.

2. An electrode according to claim 1 wherein the conducting substrate is platinum, gold, silver, copper, aluminium, iridium, palladium, rhodium, silicon, zinc, iron, steel, brass and carbon.

3. An electrode according to claim 1 wherein the conducting polymeric film is selected from polypyrrole, polyaniline and polythiophene.

4. An electrode according to claim 1 wherein the biocatalyst or bioreceptor is selected from glucose oxidase, purine nucleoside phosphorylase and xanthine oxidase, sulfite oxidase and nitrate reductase.

5. An electrode according to claim 1 wherein the conducting polymeric film further comprises a co-factor.

6. An electrode according to claim 1 wherein the conducting polymeric film further comprises a redox mediator.

7. An electrode according to claim 1 wherein the metallic nanoparticles are gold, silver, platinum, alumina, zinc oxide or silica nanoparticles.

8. An electrode according to claim 1 wherein the porous coating is non-conducting.

9. An electrode according to claim 1 wherein the porous coating is poly-ortho-phenylenediamine or is formed from a mixture of bovine serum albumin and glutaraldehyde.

10. An electrochemical sensor comprising an electrode according to claim 1, a reference electrode, and a measurement device.

11. An electrochemical sensor according to claim 10 further comprising an auxiliary electrode.

12. An electrochemical sensor according to claim 10 in the form of a combined biosensor where all electrodes are contained in one device.

13. A method for preparing an electrode according to claim 1 comprising
    i) depositing a conducting polymeric film comprising metallic nanoparticles and in which at least one biocatalyst or other bioreceptor is immobilised on a conducting substrate by electropolymerisation of a composition comprising at least one monomer capable of forming the conducting polymeric film, the at least one biocatalyst or other bioreceptor and metallic nanoparticles; and
    ii) depositing a porous coating on the conducting polymeric film.

14. A method according to claim 13 wherein the conducting polymeric film is deposited by galvanostatic, potentiostatic or potentiodynamic electrochemical polymerisation.

15. A method according to claim 13 wherein the non-conducting porous coating is deposited by dip-coating, spin coating, electrochemical deposition and electrochemical polymerisation.

16. A method for detecting an analyte in a sample comprising exposing the sample to an electrochemical sensor, the electrochemical sensor comprising an electrode comprising
   i) a conducting substrate;
   ii) a conducting polymeric film disposed on the conducting substrate, and in which at least one biocatalyst or other bioreceptor has been immobilised, and wherein the conducting polymeric film comprises metallic nanoparticles, the thickness of the polymeric film being in the range of 20 nm to 170 nm; and
   iii) a porous coating disposed on at least a portion of the polymeric film,
and observing the presence or absence of the analyte in the sample.

17. A method according to claim 16 wherein the sample is a biological sample, an environmental sample, a food or beverage sample, a soil sample or a sediment sample.

18. A method according to claim 16 wherein the analyte detected is selected from phosphate, nitrate and sulfate.

* * * * *